United States Patent
Nagy et al.

(10) Patent No.: US 11,154,550 B2
(45) Date of Patent: Oct. 26, 2021

(54) TREATMENT FOR NEURODEGENERATION

(71) Applicant: The University of Birmingham, Birmingham (GB)

(72) Inventors: Zsuzsanna Nagy, Birmingham (GB); Timothy Barrett, Birmingham (GB)

(73) Assignee: The University of Birmingham, Birmingham (GB)

( * ) Notice: Subject to any disclaimer, the term of this patent is extended or adjusted under 35 U.S.C. 154(b) by 357 days.

(21) Appl. No.: 14/431,534

(22) PCT Filed: Sep. 27, 2013

(86) PCT No.: PCT/GB2013/052523
§ 371 (c)(1),
(2) Date: Mar. 26, 2015

(87) PCT Pub. No.: WO2014/049366
PCT Pub. Date: Apr. 3, 2014

(65) Prior Publication Data
US 2015/0246037 A1    Sep. 3, 2015

(30) Foreign Application Priority Data
Sep. 27, 2012 (GB) .................... 1217296

(51) Int. Cl.
*A61K 31/496* (2006.01)
*A61K 31/145* (2006.01)
*A61K 31/19* (2006.01)
*A61K 31/436* (2006.01)
*A61K 31/192* (2006.01)
*A61K 31/4439* (2006.01)
*A61K 31/451* (2006.01)
*A61K 31/4706* (2006.01)
*A61K 31/575* (2006.01)
*A61K 31/4412* (2006.01)
*A61K 31/4418* (2006.01)
*G01N 33/50* (2006.01)

(52) U.S. Cl.
CPC .......... *A61K 31/496* (2013.01); *A61K 31/145* (2013.01); *A61K 31/19* (2013.01); *A61K 31/192* (2013.01); *A61K 31/436* (2013.01); *A61K 31/4412* (2013.01); *A61K 31/4418* (2013.01); *A61K 31/4439* (2013.01); *A61K 31/451* (2013.01); *A61K 31/4706* (2013.01); *A61K 31/575* (2013.01); *G01N 33/5058* (2013.01)

(58) Field of Classification Search
CPC .................................................. A61K 31/496
See application file for complete search history.

(56) References Cited

U.S. PATENT DOCUMENTS

| | | |
|---|---|---|
| 2007/0162989 A1 | 7/2007 | Kottmann |
| 2009/0249501 A1 | 10/2009 | Tsai et al. |
| 2011/0142799 A1* | 6/2011 | Glimcher ........... G01N 33/5008 424/85.5 |

FOREIGN PATENT DOCUMENTS

| | | |
|---|---|---|
| WO | 2005034737 A2 | 4/2005 |
| WO | 2009089011 A2 | 7/2009 |
| WO | WO 2009/137795 | 11/2009 |
| WO | WO 2013/055834 A2 * | 4/2013 |
| WO | WO 2013/112602 | 8/2013 |

OTHER PUBLICATIONS

Kakiuchi et al. ("Valproate, a Mood Stabilizer, Induces WFS1 Expression and Modulates Its Interaction with ER Stress Protein GRP94" PLoS One, 2009, vol. 4, issue 1).*
British Search Report dated Jan. 25, 2013 issued in connection with related British Application No. GB1217296.1.
PCT Search Report dated Jan. 30, 2014 issued in connection with parent PCT Application No. PCT/GB2013/052523.
Akiyama, M., et al., "Increased insulin demand promotes while pioglitazone prevents pancreatic beta cell apoptosis in Wfs1 knockout mice," Diabetologia, 52: 653-663 (2009).
Gharanei, S., et al., "Vacuolar-type H+—ATPase V1A subunit is a molecular partner of Wolfram syndrome 1 (WFS1) protein, which regulates its expression and stability," Human Molecular Genetics, 22(2): 203-217 (2013).
Terasmaa, A., et al., "Wfs1 mutation makes mice sensitive to insulin-like effect of acute valproic acid and resistant to streptozocin," J. Physiol. Biochem., 67: 381-390 (2011).
Yamada, T., et al., "WFS1-deficiency increases endoplasmic reticulum stress, impairs cell cycle progression and triggers the apoptotic pathway specifically in pancreatic β-cells," Human Molecular Genetics, 15(10): 1600-1609 (2006).

* cited by examiner

*Primary Examiner* — Yong S. Chong
(74) *Attorney, Agent, or Firm* — Hoxie & Associates LLC

(57) ABSTRACT

Provided is a method of treating and/or preventing Wolfram Syndrome (WS)-related neurodegeneration (i.e. of Wolfram Syndrome-Associated Neuronal Degeneration), by increasing the expression and/or functional activity of p21. A method of screening for pharmacological agents useful in treating and/or preventing such conditions is also provided.

7 Claims, 43 Drawing Sheets

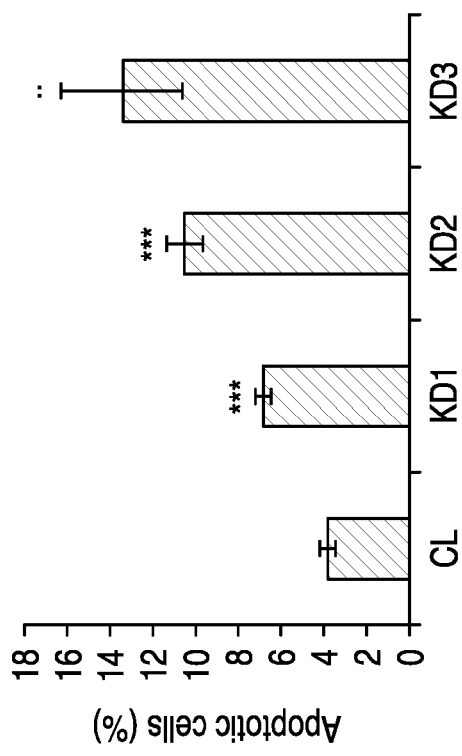

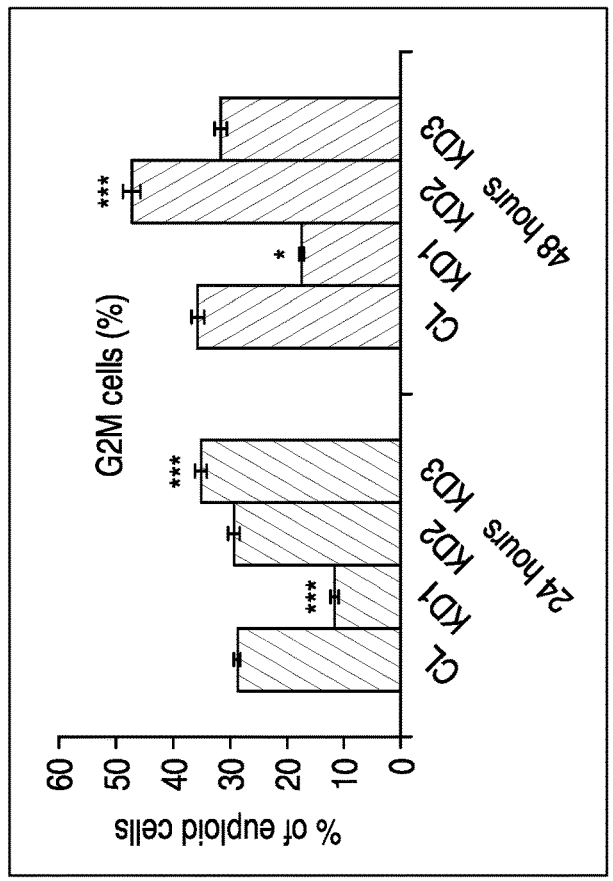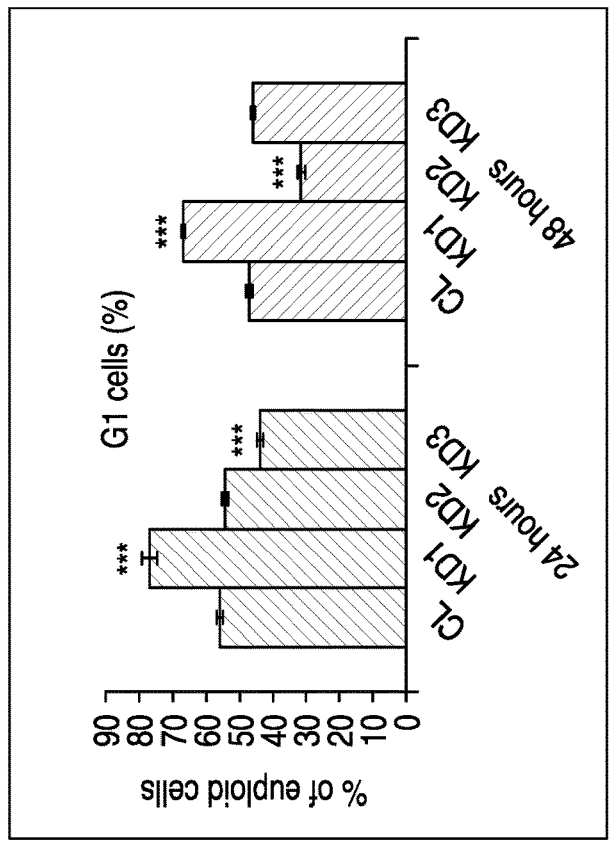
Figure 4 (cont'd)
Figure 4B

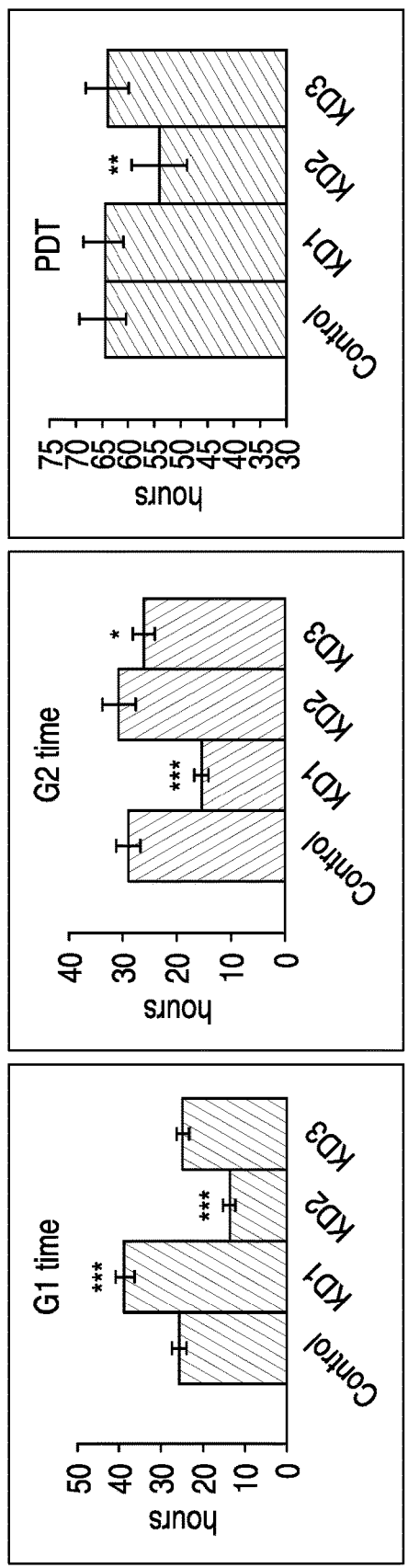
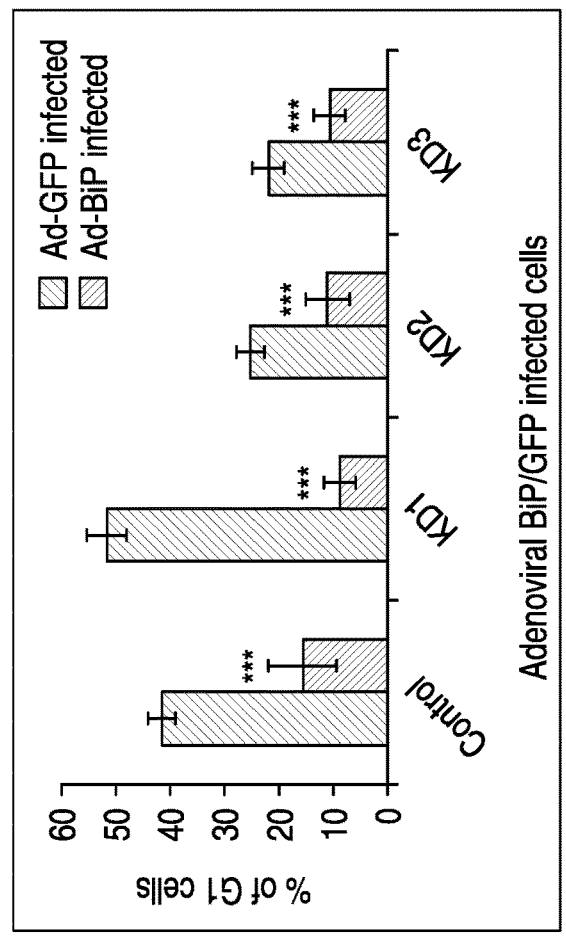
Figure 4 (cont'd)
Figure 4C
Figure 4D

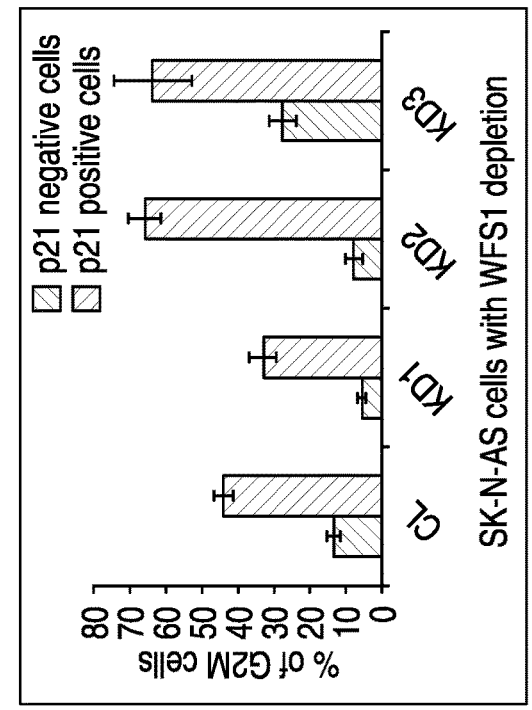
Figure 4F
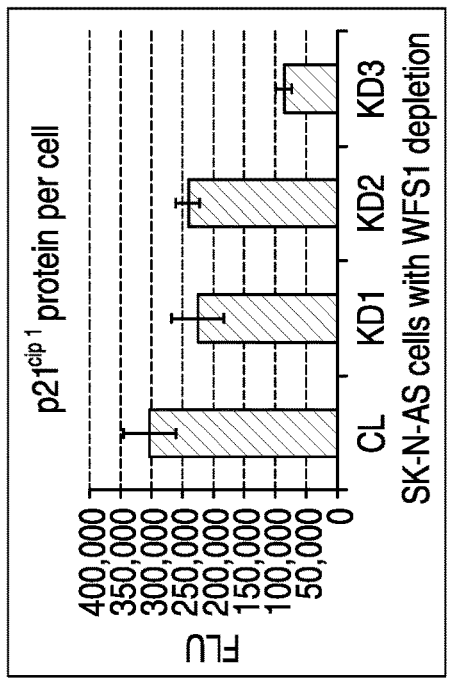
Figure 4E
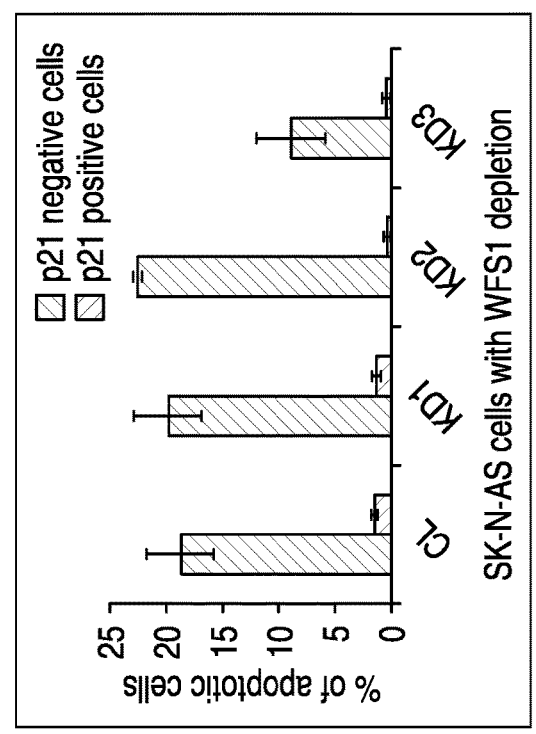
Figure 4G
Figure 4 (cont'd)

Figure 5A (above)

Figure 5B (above)

Figure 5C (above)

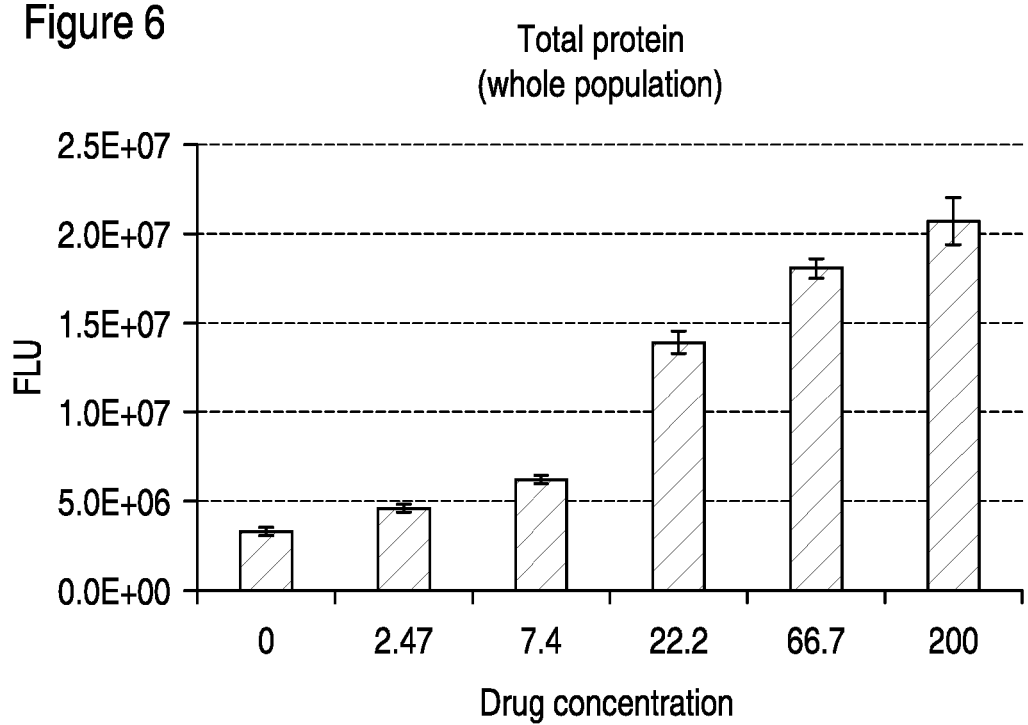
Figure 6A (above)

Figure 6B (above)

Figure 6C (above)

Figure 7A (above)

Figure 7B (above)

Figure 7C (above)

Pioglitazone

Ciclopirox Olamine

Dapsone

Rifampicin

Loperamide hydrochloride

TREATMENT FOR NEURODEGENERATION

The present invention relates to a method of treating and/or preventing Wolfram Syndrome (WS)-related neurodegeneration (i.e. of Wolfram Syndrome-Associated Neuronal Degeneration).

INTRODUCTION

Wolfram Syndrome (WS), also called DIDMOAD (Diabetes Insipidus, Diabetes Mellitus, Optic Atrophy, and Deafness), is a rare autosomal recessive disorder characterised by neurodegeneration and diabetes mellitus. The gene responsible for the syndrome (WFS1) encodes an endoplasmic reticulum (ER) resident transmembrane protein that also localises to secretory granules in pancreatic beta cells. Although its precise functions are unknown, WFS1 protein deficiency affects the unfolded protein response, intracellular ion homeostasis, cell cycle progression, and granular acidification. There are more than 100 WFS1 mutations that cause Wolfram syndrome. Some of these delete or insert DNA from the WFS1 gene and, as a result, little or no wolframin is present in cells. Other mutations lead to the replacement of one amino acid in the protein. These mutations appear to reduce wolframin activity dramatically. Although the mechanisms of neurodegeneration related to WS are not entirely elucidated, it is clear that the reduction of WFS1 amount or activity leads to neuronal death. There are no known methods at present to treat or prevent the neurodegeneration associated with WS. Indeed, it is believed that there are currently no drugs in the pipeline to treat this debilitating disease.

p21 (CIP1/WAF1, CDKN1A, OMIM reference: 116899, Cytogenetic location: 6p21.2) is a protein that in humans is encoded by the CDKN1A gene located on chromosome 6 (6p21.2). p21 is primarily known from investigations into its role in cell cycle regulation. Its clinical importance is associated mainly with cancer and resistance against HIV infection. The p21 protein has been reported to be specifically cleaved by CASP3-like caspases. p21 may inhibit the apoptosis induced by cell cycle arrest and p53 expression. Two alternatively spliced variants, which encode an identical protein, have been reported.

Surprisingly, we have found that in WFS1 depleted neuronal cells increased levels of p21(CIP1/WAF1) is able to prevent neuronal apoptosis and reverse the cell cycle disturbance caused by the WFS1 depletion (Gharanei et al., *Human Molecular Genetics*, 2013, Vol. 22, No. 2, pages 201-217). We conclude that increasing the levels of p21 (CIP1/WAF1, CDKN1A) can treat and/or prevent WS-related neurodegeneration.

US2009/249501 relates to an animal model of WS and its use in the identification of therapies to treat WS type. In particular, the document describes a Cisd2 knockout mouse. WS type 2 has been linked with a mutation in the Cisd2 gene, the function of which is unknown. This document makes no mention of p21.

WO2005/034737 describes a method of measuring endoplasmic reticulum (ER) stress in a cell or biological sample, and use of the method to identify compounds for the treatment of WS. This document makes no mention of p21. Takahiro et al., (*Human Molecular Genetics*, 2006, Vol. 15, pages 1600-1609) teach that ER stress leads to elevated p21 expression, and that overexpression of p21 is associated with cell death. This is contrary to the findings presented herein.

WO2009/089011 relates to the formulation of resveratrol for human therapeutic application. It describes administration of the formulation for treating of diseases or disorders that would benefit from increased mitochondrial activity. WS is included in a list of such disorders. However, no mention is made of p21.

SUMMARY OF THE INVENTION

Thus, p21 is a target for treating and/or preventing Wolfram Syndrome (WS)-related neurodegeneration.

Accordingly, in a first aspect, the present invention provides a compound capable of increasing the expression and/or functional activity of p21 for use in a method of treating and/or preventing Wolfram Syndrome (WS)-related neurodegeneration.

We have found that decreased Wolfram protein, WFS1, expression leads to apoptosis, presumably mediated by irresolvable ER stress. We then evaluated whether the cell cycle effects of WFS1 were due to alterations in $p21^{cip}$ levels. We found that significant $p21^{cip}$ downregulation was present in all three WFS1 depleted cell lines. However, when present, the expression of $p21^{cip}$ was associated with the inhibition of progression through the G2 phase of the cell cycle and inhibition of apoptosis in all cell lines: see FIG. 4 and the discussion thereon.

Overall, we found significant $p21^{cip}$ downregulation in WFS1 depleted cells in comparison to controls. Additionally, we have discovered that WFS1 depleted cells that retain their p21 expression are protected against cell death (apoptosis). Thus, p21 alone is sufficient to prevent cell death in Wolfram protein-depleted cells.

The compounds listed in Table 4 are amongst those known that have an effect on p21 expression and/or functional activity. We believe that any, or a combination of any, of these drugs may, by inducing or activating p21, provide a treatment for and/or a prevention of neurodegeneration associated with WS. Accordingly, any one of these compounds, or any combination of two or three, or four or more of these compounds, is preferred.

The compound may be a considered to be a drug or may be further defined as a small molecule, a polynucleotide such RNA, or an antibody, for instance. A non-exhaustive list of examples of suitable compounds is provided herein (Table 4). The compound acts to reduce cell death in Wolfram protein-depleted cells. This may be by either inducing p21 expression and/or help its translocation to the active site (nucleus).

Increased (or up-regulated) expression of p21 may preferably encompass one or a combination of any of:
  (i) increased transcription of p21; and/or
  (ii) reduced degradation of p21 RNA and/or peptide and/or protein. Increased functional activity of p21 may preferably encompass one or both of:
  (iii) enhanced activation of p21;
  (iv) enhanced nuclear translocation of p21.

In simplistic terms, therefore, the present compound will act to either increase the amount of p21 protein available and/or will act to ensure that any p21 protein is fully active (i.e. activated) and in the correct localisation within the cell (i.e. it has been delivered to the nucleus, where it acts), or at least maximise these, so the overall effectiveness of p21 is improved.

The compound may act to simply increase expression, and this is preferred. However, in an alternative, and preferred, embodiment the compound may act to merely increase p21 activation (without an increase in p21 expression). Increased activation also includes reduced deactivation of p21, for instance by caspases.

The modes of action of the compound are as follows. The list in Table 4 shows compounds that are all known to have one or more of the following effects: that they increase Expression, increase Binding, increase Activation, increase Accumulation and/or increase Induction of p21 (including any combination thereof).

It will be appreciated that the effect of these compounds in terms of p21 expression and/or activation can be shown to reduce neuronal cell death in vitro models or in animal models of WS. The methods to measure increased p21 expression (in the tissue, whole cell or nuclear extracts) in the treated cells or in the nervous tissue of animal models may include, but are not restricted to, western blotting, fluorescent immunocytochemistry followed by image analysis and cytometry, and ELISA. The methods to measure increased p21 activity (in the tissue, whole cell or nuclear extracts) in the treated cells or in the nervous tissue of animal models may include, but are not restricted to, cell cycle analysis, activity of target cyclin dependent kinases (enzyme activity assays), binding to target cyclin dependent kinases (immuno precipitation and western blotting).

One or more of the preferred compounds may be used together, especially if they increase the levels of expression and/or functional activity of p21 in different ways. For instance, the compounds have been classed herein by reference to their mode of action, so one form each class may preferably be used.

It will be appreciated that the patient is preferably a human. Administration of the compound to the patient may be referred to as administration to a patient in need thereof. Administration will need to be by means appropriate to each compound, but may include oral ingestion, subcutaneous administration, intradermal administration or administration via a mucous membrane.

Wolfram Syndrome (WS)-related neurodegeneration may be considered to be neuronal death (apoptosis of the affected neurones) caused by or linked to depletion of the Wolfram protein.

In general, it will be appreciated that the compound achieves relief of symptoms, or halts the progression of the disease, or results in an improvement in overall CNS function. Prevention or delay of cell death is intended.

In general it will also be appreciated that since p21 expression or activity cannot be directly measured in the neurones of a live patient (using methods known in the present state of art) the effectiveness of the therapy will be accepted if:
  i). The patient's symptoms are reduced over time
  ii). The patient's symptoms do not worsen over time at the rate expected in WS patients
  iii). Imaging signs of neuronal atrophy or functional loss (using techniques such as, but not restricted to, MRI, MRI Spectroscopy) are diminished over time
  iv). Imaging signs of neuronal atrophy or functional loss (using techniques such as, but not restricted to, MRI, MRI Spectroscopy) do not worsen over time at the rate expected in WS patients.

In some embodiments, the compound is known in literature to affect p21 expression and activation.

In some embodiments, the compound is Rapamycin.
In some embodiments, the compound is Flurbiprofen.
In some embodiments, the compound is Dexrazoxane.
In some embodiments, combinations of all three of the above can be provided. In some embodiments, a combination of Rapamycin with Flurbiprofen is provided. In some embodiments, a combination of Flurbiprofen and Dexrazoxane is provided. In some embodiments, a combination of Rapamycin with Dexrazoxane is provided.

In some embodiments, the compound is Valproic acid or a salt thereof. In particular, the compound may be Sodium Valproate.

In some embodiments, the compound is Chloroquine diphosphate.

In some embodiments, the compound is Pioglitazone.

In some embodiments, the compound is 4-phenylbutyric acid (4-PBA), or a salt thereof.

In particular, the compound may be Sodium 4-phenylbutyrate.

In some embodiments, the compound is Fusidic acid.

In some embodiments, the compound is Ciclopirox Olamine (CPX).

In some embodiments, the compound is Dapsone (4-Aminophenyl sulfone).

In some embodiments, the compound is Rifampicin.

In some embodiments, the compound is Loperamide or a derivative thereof, such as Loperamide hydrochloride.

It will be appreciated that any of the compounds listed above can be used in combination with one or more of the other compounds.

Preferred doses of the compound will be readily apparent to the skilled person and can be easily determined, but it is particularly preferred that doses are as small as the smallest therapeutically-effective dose. These are all compounds used in a clinic, so dosage ranges will be well-known.

In a second aspect, the present invention also provides a method of treating and/or preventing Wolfram Syndrome (WS)-related neurodegeneration, comprising administering the present compound to a patient.

The target, p21, is polymorphic in the human population and the polymorphisms affect the activity of p21, so the present use and methods may additionally also comprise a screen to detect the polymorphic form of p21 displayed by the patient. This may provide a degree of personalisation to the treatment, and as such this may influence the choice of compounds that a medical practitioner, for instance, prescribes.

In a third aspect, the invention provides a method of screening for pharmacological agents useful in treating and/or preventing Wolfram Syndrome (WS)-related neurodegeneration in a particular patient. The screening method comprises:
  (i) contacting a cell of the patient, with a test agent;
  (ii) measuring the expression and/or functional activity of p21;
  (iii) measuring the expression and/or functional activity of p21 in a control cell not exposed to the agent; and
  (iv) comparing the measurements taken in steps (ii) and (iii).

A difference in the measurements taken in steps (ii) and (iii) indicates that the agent is suitable for use in a method of treating and/or preventing Wolfram Syndrome (WS)-related neurodegeneration in the patient.

BRIEF DESCRIPTION OF THE FIGURES

The invention will now be described with reference to the Figures.

FIG. 1: WFS1 depletion in stable neuroblastoma clones results in activation of ER stress response markers and increase in apoptosis markers. CL=control, KD1, KD2, KD3=WFS1 depleted stable clones. *$p<0.05$, $p<0.01$, and *$p<0.001$.

FIG. 1E: Increase in the percentage of early apoptotic cells in the WFS1 depleted stable clones in comparison to the control—High Content Cytometry. T-test vs controls: $p<10^{-5}$ for KD1 and KD2, $p<0.01$ for KD3 versus control, n=5 (n=number of technical replicates (independent cultures of stable clones)).

After 24 hours of growing the cells were infected with either ad.BiP or ad.GFP at MOI=8.5, 16 hours later harvested for either RNA or protein analysis. CL=control, KD1, KD2 and KD3 stably WFS1 depleted clones. *$p<0.05$, $p<0.01$, and *$p<0.001$.

Figure 1A:
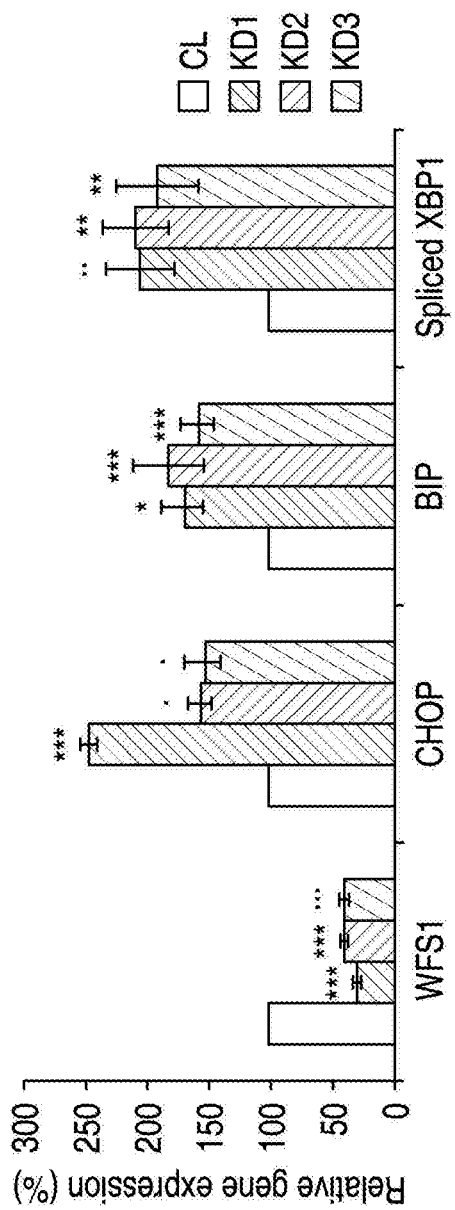
FIG. 1A: QPCR analysis of WFS1 and ER stress markers. T-test: WFS1 expression vs controls: $p<10^{-5}$ for KD1-3 respectively, n=6. CHOP: $p<10^{-5}$ for KD1 and $p<0.05$ for KD2 and KD3, n=3. BiP: $p<0.05$ for KD1 and $p<0.001$ for KD2 and KD3, n=5. Spliced XBP1: $p<0.01$ for KD1-KD3, n=7 (n=number of independent runs using at least 3 RNA preparations from independently cultured stable clones).
Figure 1B:
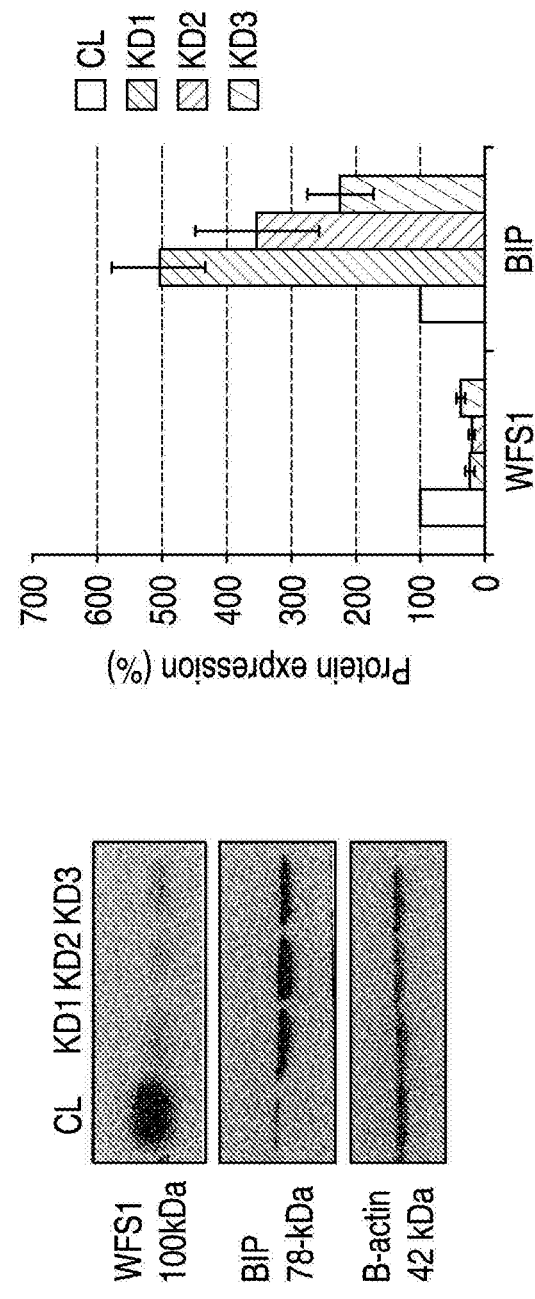
FIG. 1B: Western blot analysis with antibodies to WFS1, and BiP—representative experiment (Beta actin=reference). Double bands may correspond to splice variants (at least two of approximately 68 kDa and 64 kDa are known). Bar chart—quantification of Western Blot, T-test vs controls: WFS1: $p<0.001$ for KD1 and KD2, $p<0.05$ for KD3, n=6. BIP: $p<0.01$ for KD1 and $p<0.05$ for KD2 and KD3, n=6. (n=number of independent runs using at least 3 independently prepared protein extracts).
Figure 1C:
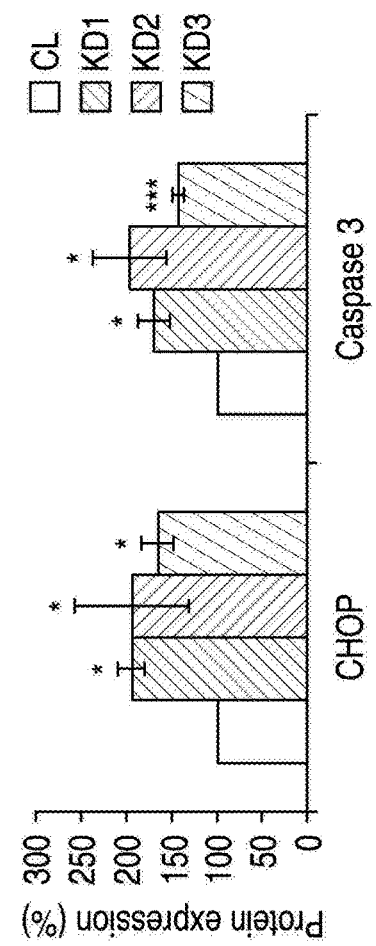
FIG. 1C: Western blot analysis with antibodies to HRD1 and ATF6—representative immunoblot (Beta actin= reference). Bar chart-quantification of Western Blot: T-test vs controls: HRD1: $p<0.01$ for KD1 and KD2, n=4. ATF6: $p<0.05$ for KD1 and KD2 respectively, n=4 (n=number of independent runs using 3 independently prepared protein extracts).
Figure 1C:
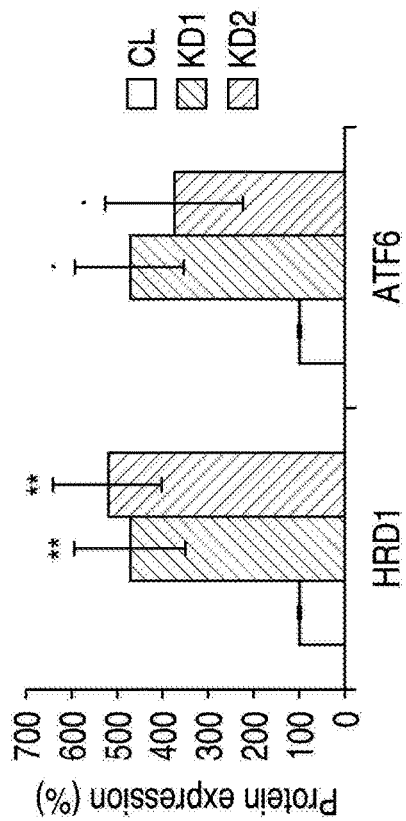
Figure 1D:
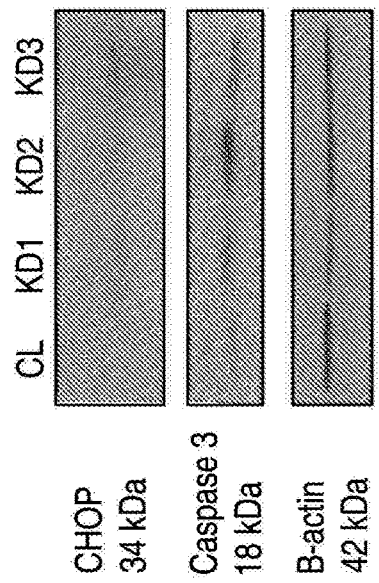
FIG. 1D: Western blot with antibodies to CHOP and cleaved caspase-3—representative immunoblot (Beta-actin=reference). Bar chart-quantification of western blot, T-test vs controls: CHOP: $p<0.05$ for KD1, KD2 and KD3, n=3. Caspase-3 $p<0.05$ for KD1 and KD2, $p<0.001$ for KD3, n=5 (n=number of independent runs using 4 independently prepared protein extracts).
Figure 1D:
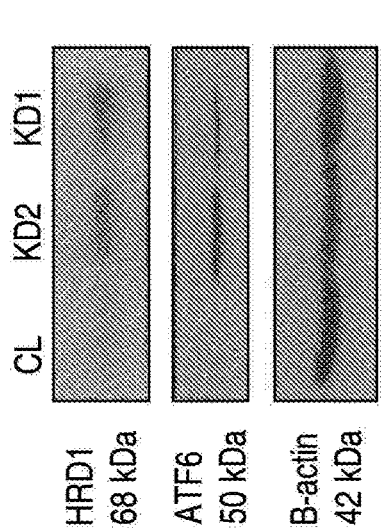
Figure 2A:
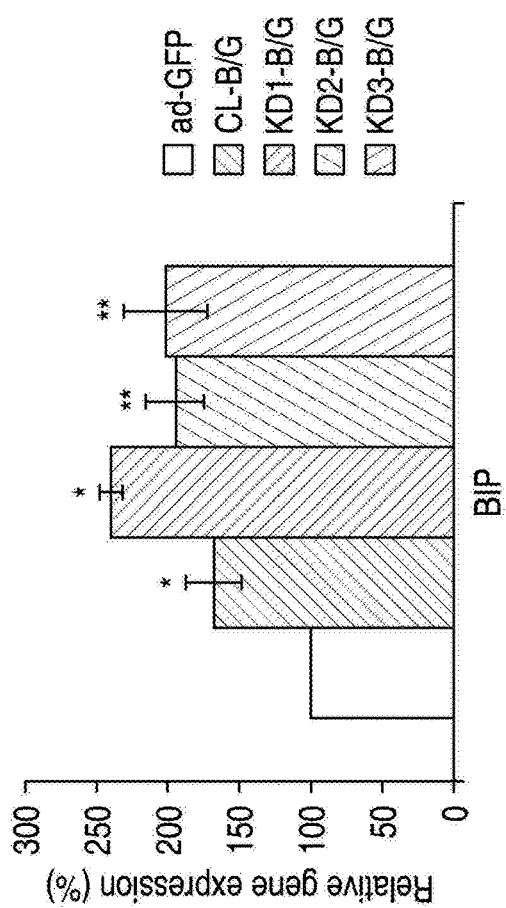
FIG. 2: Adenoviral over-expression of GRP78/BiP in WFS1 stably depleted neuroblastoma cells.

FIG. 2A: Over-expression of BiP mRNA in stably depleted clones infected with ad.BiP in comparison to corresponding controls infected with ad.GFP. The expression of BiP was assumed equal to 100% for each ad.GFP infected clones (CL and KD1-3) and is illustrated by one white bar on the chart. QPCR analysis, T-test: ad.BiP CL/ad.GFP CL and ad.Bip KD1/ad.GFP KD1 $p<0.05$; ad.BiP KD2/ad.GFP KD2 and ad.BiP KD3/ad.GFP KD3 $p<0.01$ (n=3).

Figure 2B:
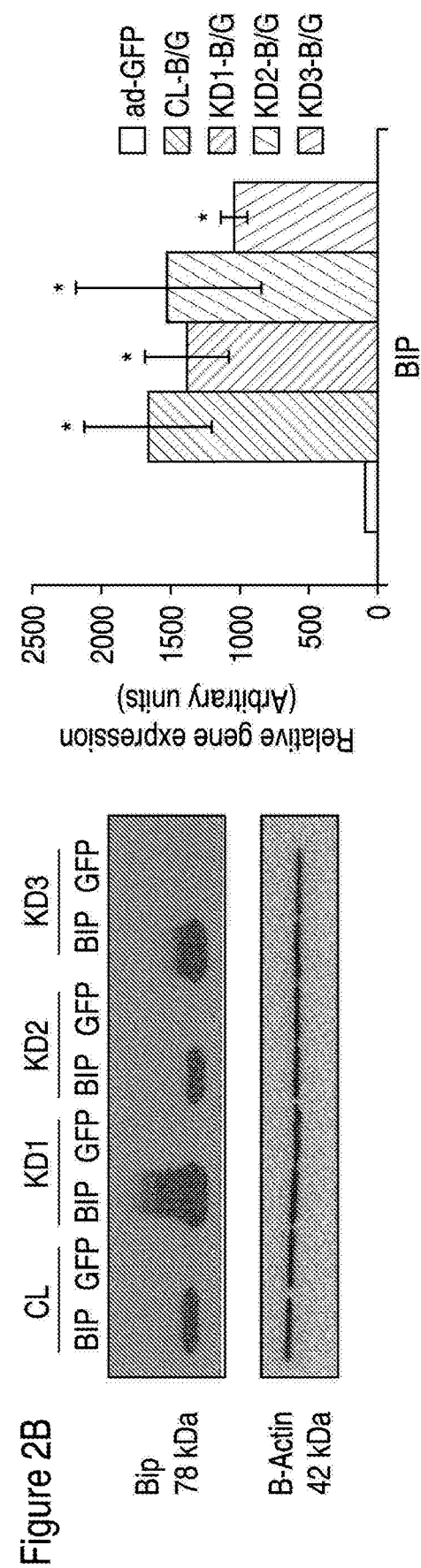

FIG. 2B: Over-expression of BiP protein—representative immunoblot with antibody to BiP and beta-actin. Bar chart—immunoblot quantification: the expression of BiP was assumed equal to 100 arbitrary units for each ad.GFP infected clone (CI and KD1-3) and is illustrated by one white bar on the chart. T-test ad.BiP/ad.GFP for all clones was $p<0.05$. The expression of BiP is presented in arbitrary units. Ad.GFP infected clones (CL and KD1-3) are illustrated by one white bar on the chart.

Figure 2C:
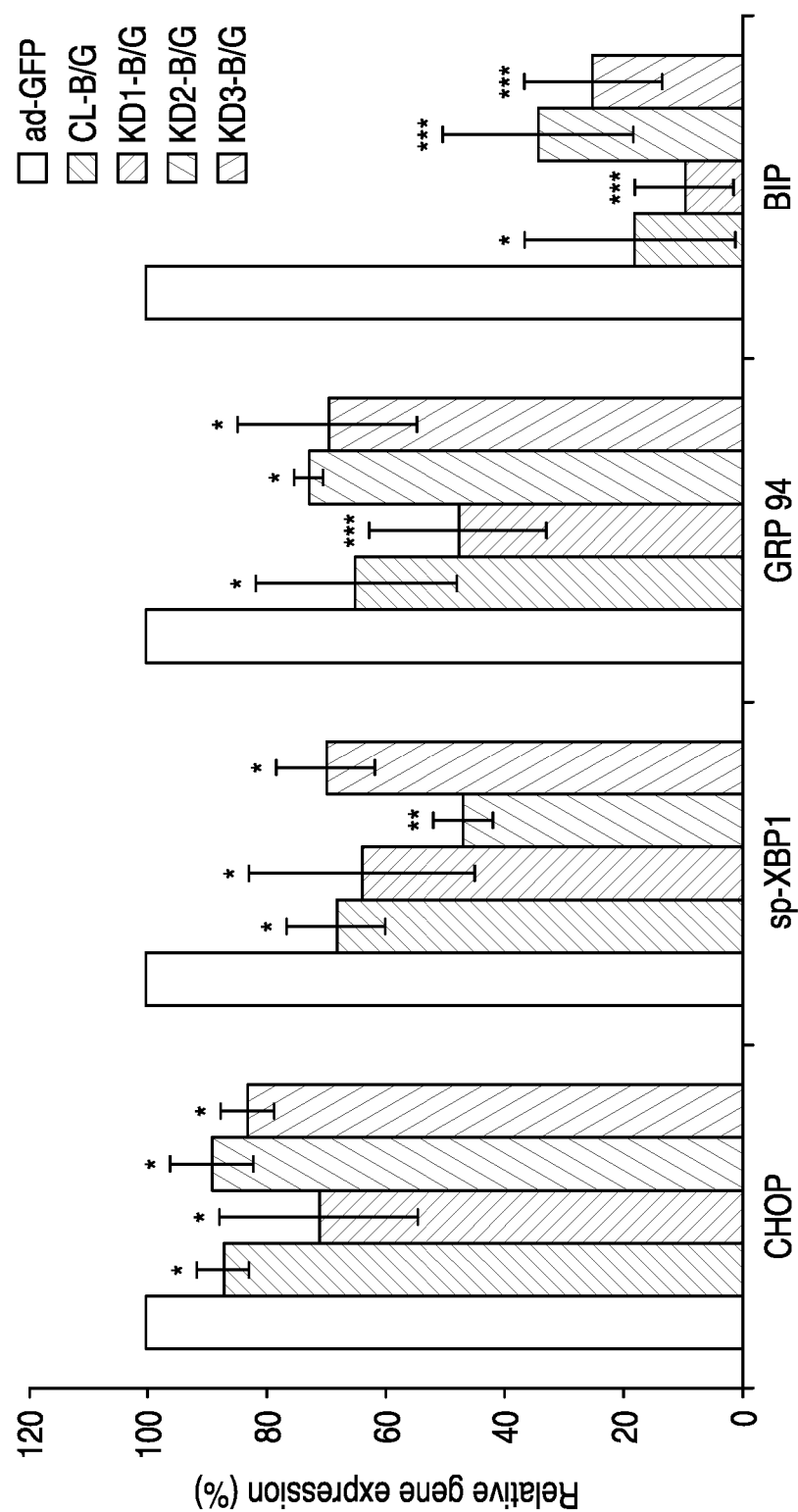

FIG. 2C. QPCR analysis of the expression of ER stress markers in stably depleted clones infected with ad.BiP in comparison to corresponding controls infected with ad.GFP. The expression of each marker was assumed equal to 100% for each ad.GFP infected clone (CL, KD1-3) and is illustrated by one white bar on the chart. T-test: CHOP ad.Bip/ad.GFP for the control and depleted cell lines was $p<0.05$. Spliced XBP1: $p<0.05$ for ad.Bip CL/ad.GFP CL, ad.Bip KD1/ad.GFP KD1, and ad.BiP KD3/ad.GFP KD3. For ad.BiP KD2/ad.GFP KD2 $p<0.01$, GRP94: $p<0.05$ for ad.BiP CL/ad.GFP CL, ad.BiP KD2/ad.GFP KD2 and ad.BiP KD3/ad.GFP KD3, $p<0.001$ for ad.BiP KD1/ad.GFP KD1. Endogenous BiP: $p<0.05$ for ad.BiP CL/ad.GFP CL, $p<10^{-5}$ for ad.BiP KD1/ad.GFP KD1 and ad.BiP KD3/ad.GFP KD3, $p<0.001$ for ad.BiP KD2/ad.GFP KD2. (n=3 in all experiments).

Figure 2D:
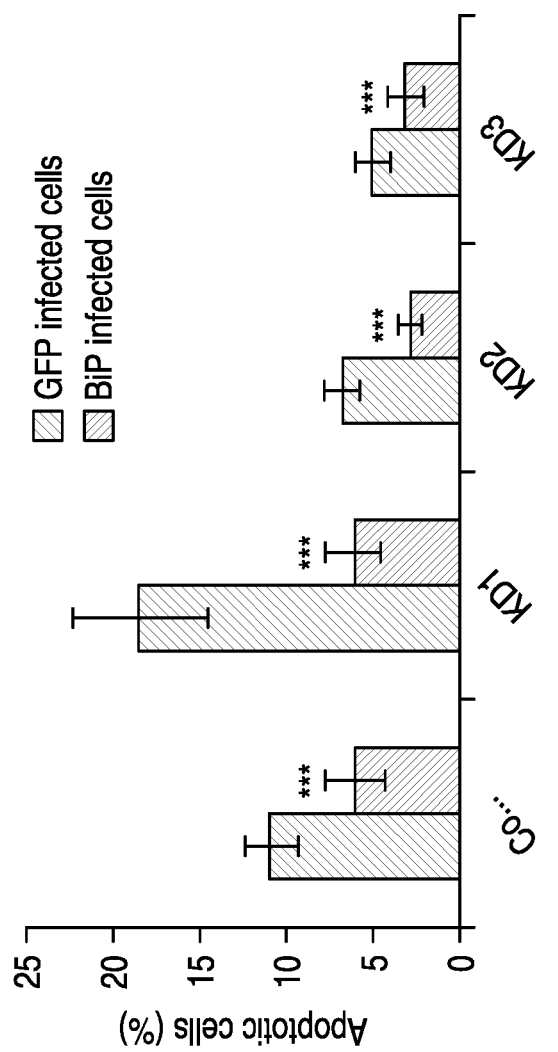

FIG. 2D: Reduction in number of apoptotic cells in WFS1 depleted stable clones after adenoviral transduction of BiP in comparison to cells transduced with ad.GFP ($p<0.01$). GFP infected, BiP infected (CL=11±1.6, 6±1.7), KD1 (19±3.9, 6±1.6), KD2 (7±1, 3±1), KD3 (5±1, 3±1).

FIG. 3: Characterisation of transiently WFS1 depleted neuroblastoma SK-N-AS and neuronal NT2 cells. CL=control; KDA, KDB: transiently depleted neuroblastoma cells. KDC and KDD: transiently depleted neuronal NT2 cells. *$p<0.05$, $p<0.01$, and *$p<0.001$.

Figure 3A:
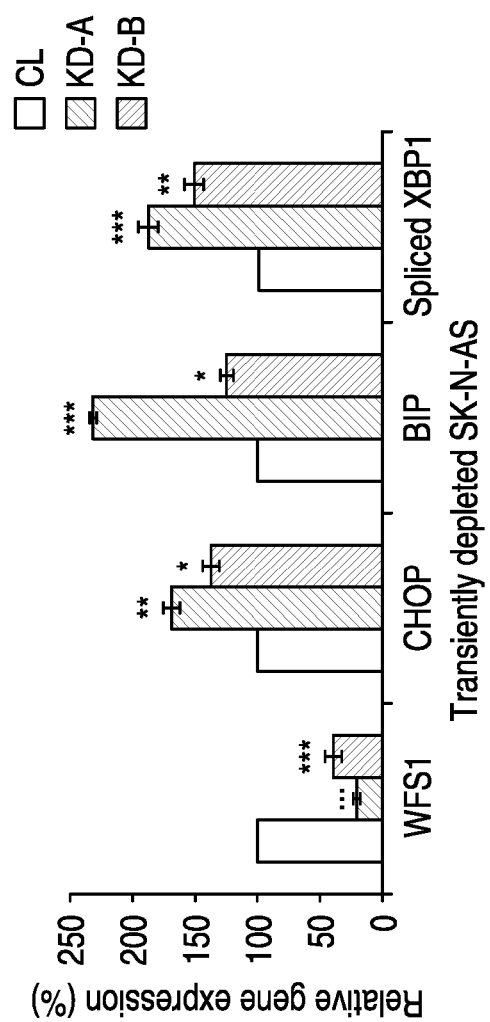

FIG. 3A: QPCR analysis of WFS1 and ER stress markers BIP, CHOP and spliced XBP1 expression in transiently depleted SK-N-AS cells. T-test WFS1 vs controls: $p<10^{-5}$ for KDA and KDB, n=6. CHOP $p<0.01$ and $p<0.05$ for KDA and KDB respectively n=3, BIP $p<10^{-5}$ and $p<0.05$ respectively, n=3; spliced XBP1 $p<0.001$ and $p<0.01$, n=3 (n=number of independent runs using at least 3 RNA preparations from independently silenced neuroblastoma cell lines).

Figure 3B:
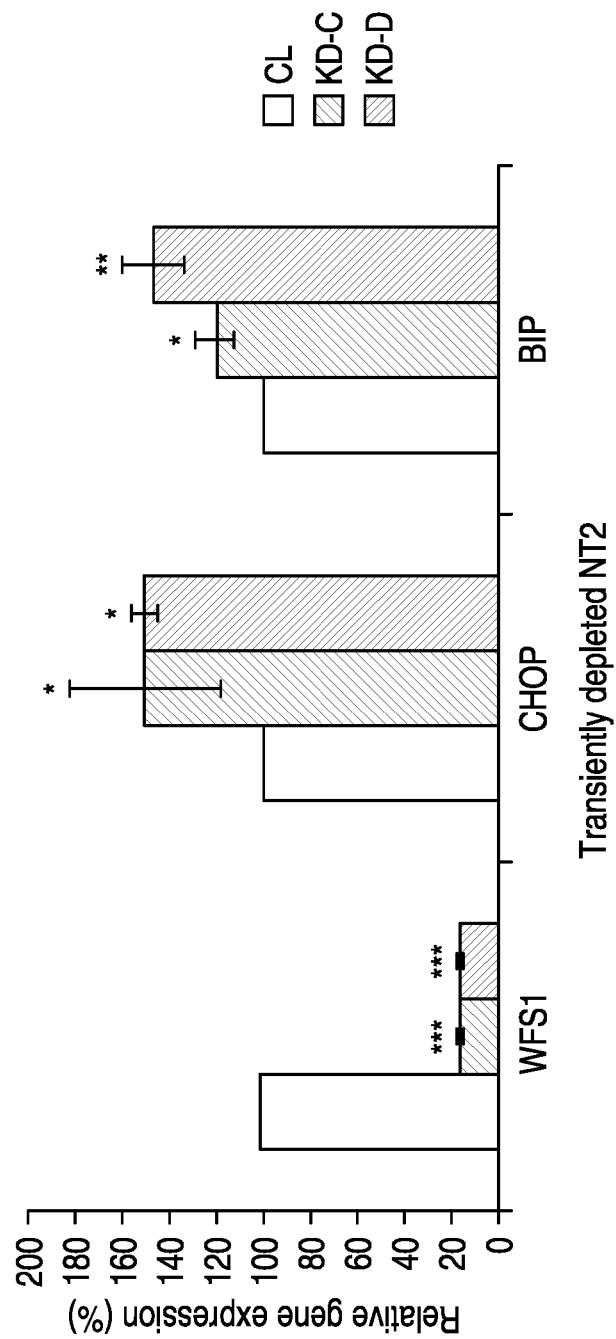

FIG. 3B: QPCR analysis of WFS1 and ER stress markers BiP and CHOP expression in NT2 human neuronal cell line with transient WFS1 depletion. T-test WFS1 depletion vs controls: $p<10^{-5}$ for KDC and KDD respectively, n=5. CHOP $p<0.05$ for KDC and KDD, n=3. BIP: $p<0.05$ and $p<0.01$ for KDC and KDD respectively, n=3 (n=number of independent runs using at least 3 RNA preparations from independently silenced NT2 cell lines).

FIG. 4: Role of WFS1 in cell cycle regulation

Figure 4A:
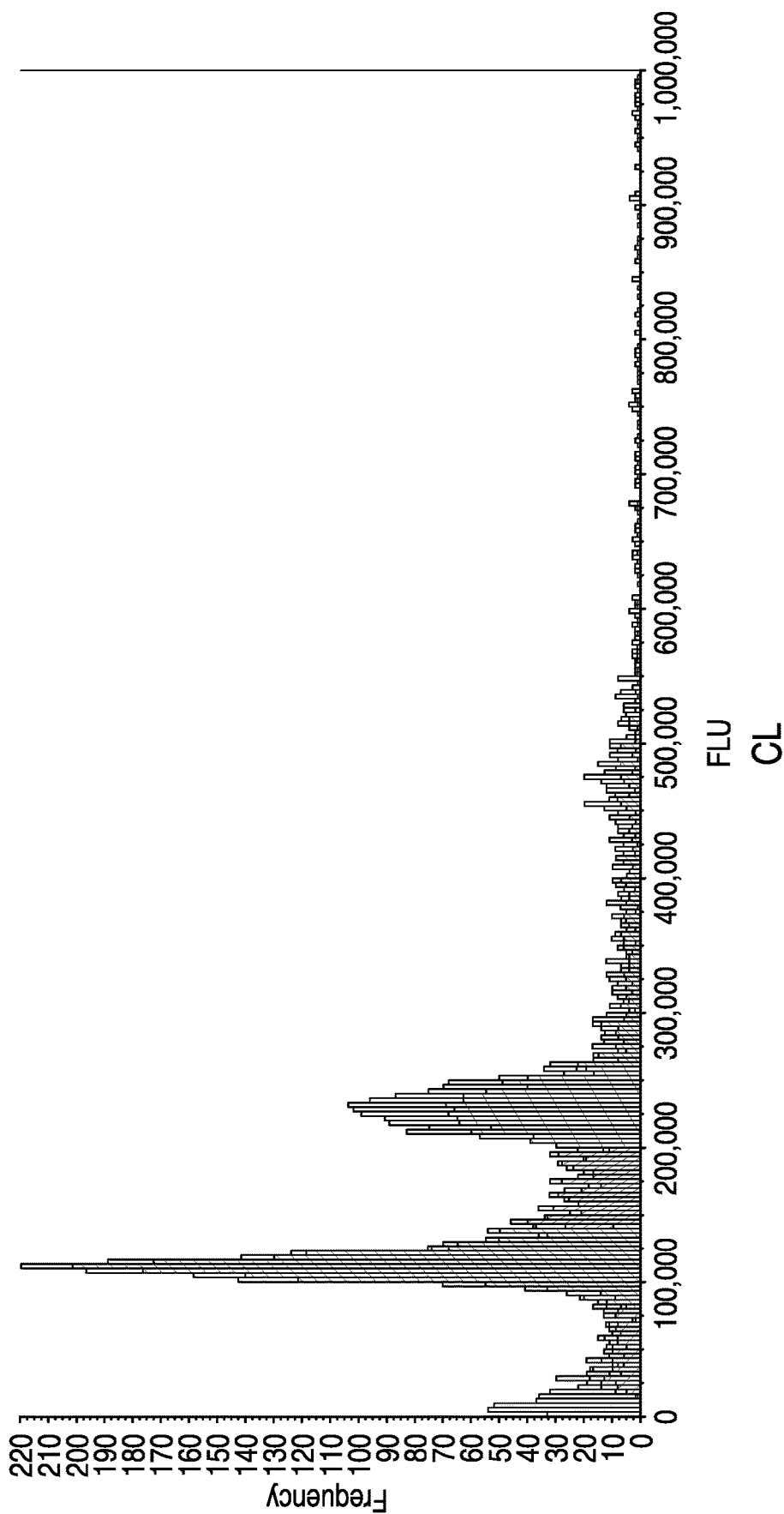
Figure 4A:
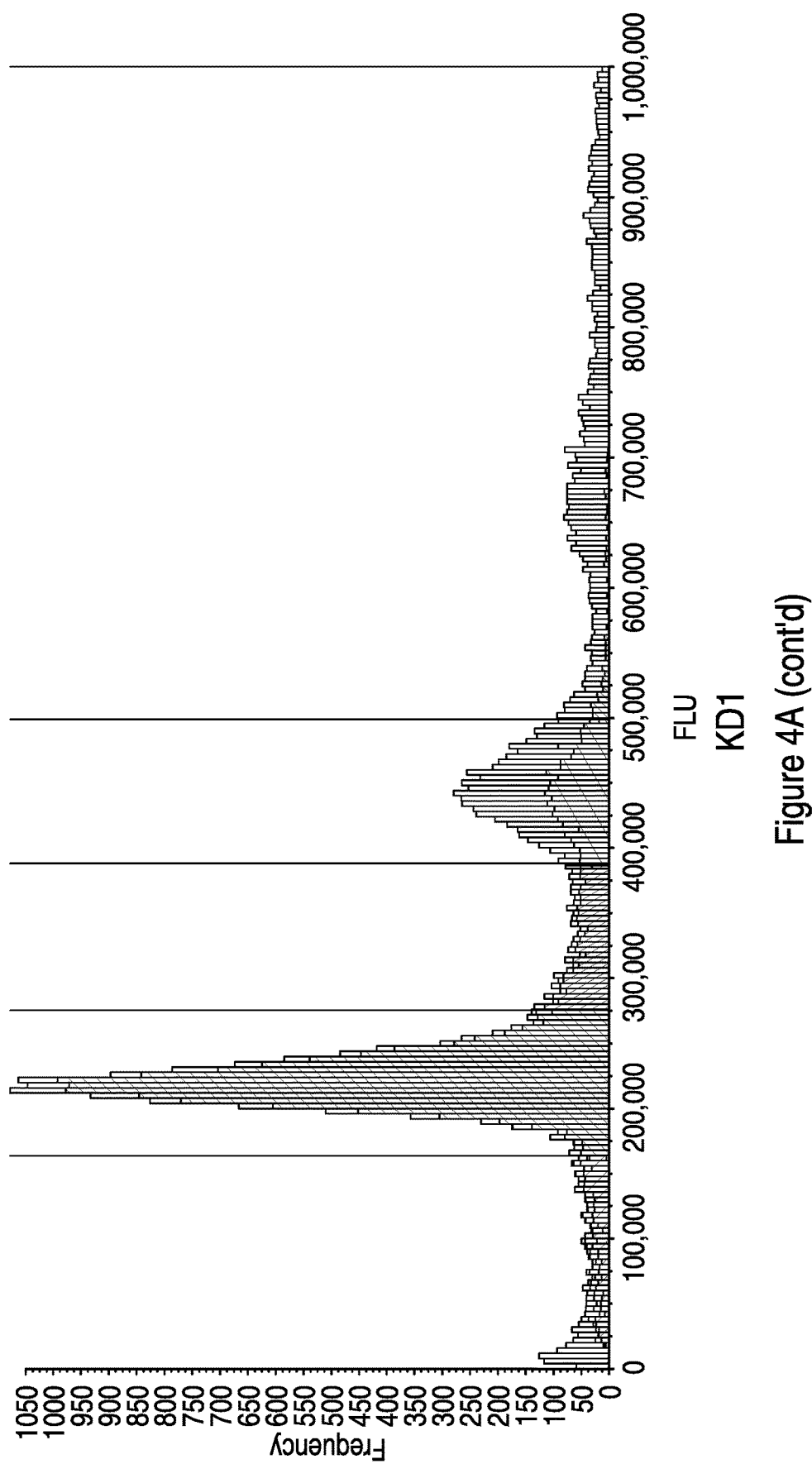
Figure 4A:
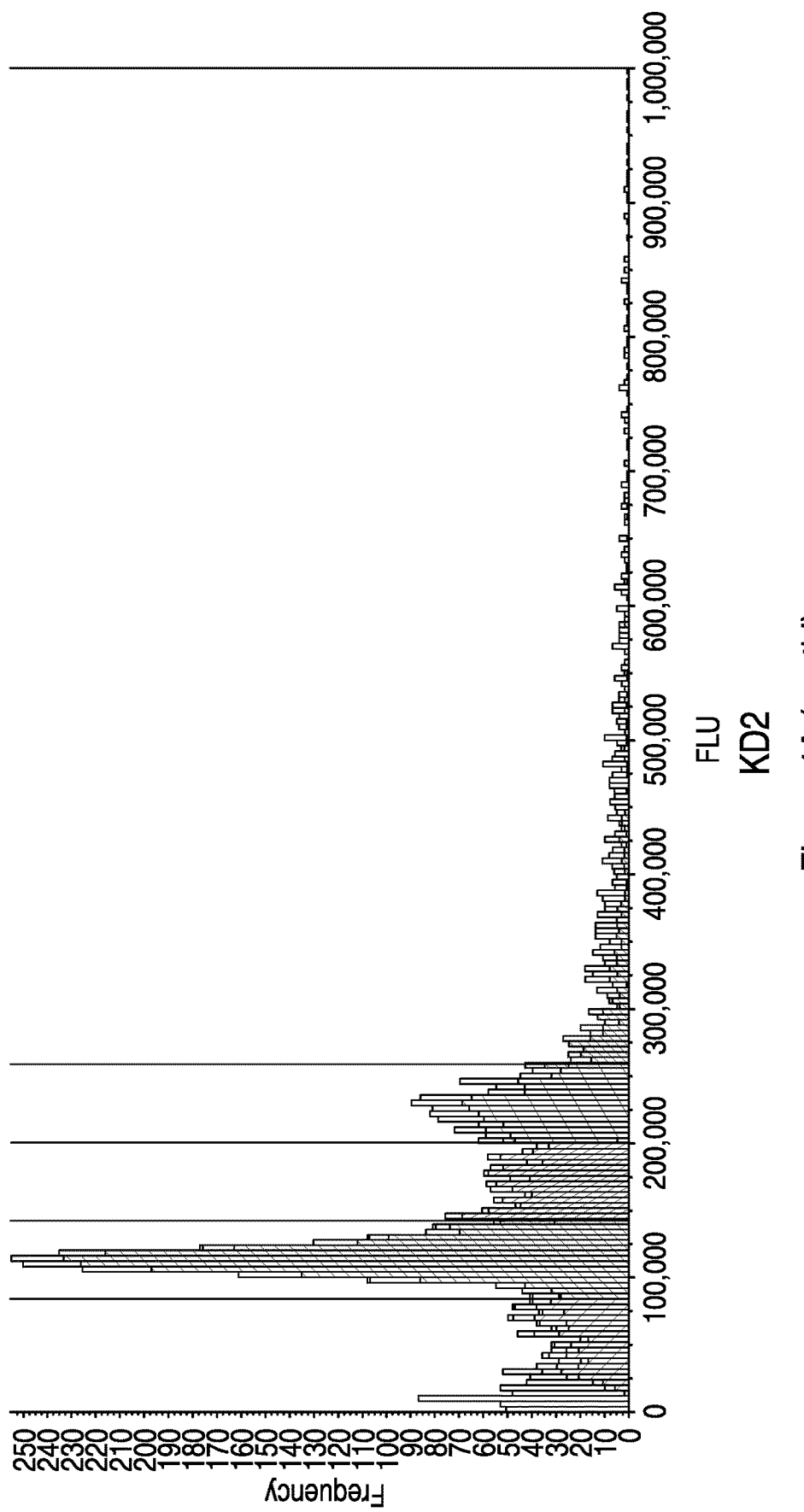
Figure 4A:
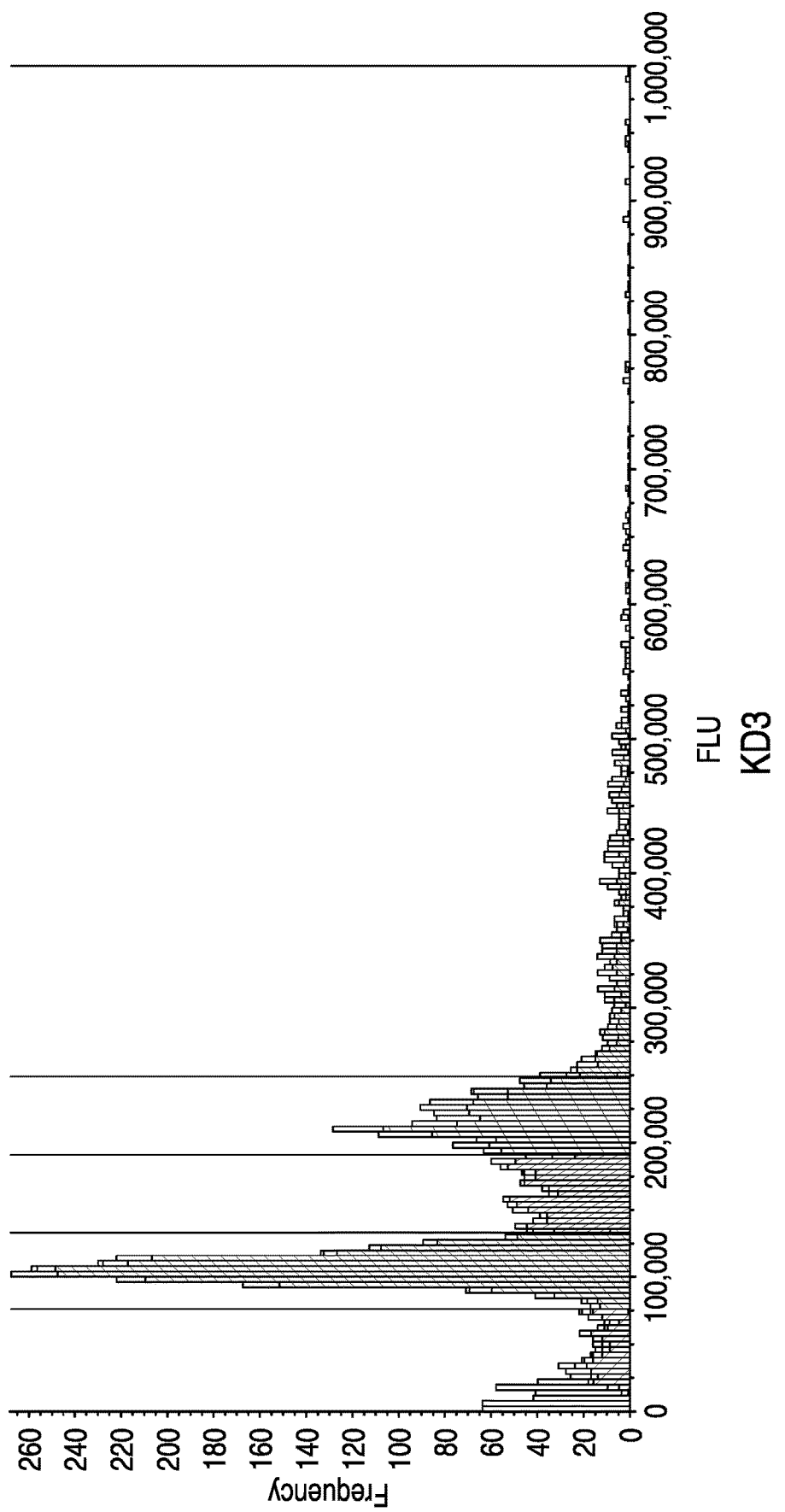

FIG. 4A: Cytometric histogram showing the number of cells (y axis) with different DNA content (x axis). The KD1 line is clearly tetraploid, showing a shift in the DNA content.

FIG. 4B: percentage of cells in G1 and G2 phases of the cell cycle after 24 and 48 hour cell growth. P values calculated by Stat Calc using the comparison of means between independent groups (different cell lines versus control); after 24 hours cell growth the p-values for G1 and G2 (KD1 v CI: $p<0.001$, KD2 v CI: p=NS, KD3 v CI: $p<0.001$). Similarly after 48 hours cell growth (KD1 v CI: $p<0.05$, KD2 v CI: $p<0.001$, KD3 v CI: p=NS).

FIG. 4C: Length of the G1 phase; p-value (KD1 v CI and KD2 v CI: $p<0.001$, KD3 v CI: p=NS). Length of the G2-phase: p-value (KD1 v CI: $p<0.001$, KD2 v CI: p=NS, KD3 v CI: $p<0.05$), Population Doubling Time (PDT): p value (KD1 v CI and KD3 v CI: p=NS, KD2 v CI: $p<0.01$).

FIG. 4D: Normalisation of cell cycle kinetics by adenoviral over-expression of GRP78/BiP. The percentage of cells in G1 was significantly decreased in ad.BiP infected cells in comparison to ad.GFP infection ($p<10^{-5}$).

FIG. 4E. Expression of $p21^{cip}$ protein per cell, measured as fluorescence units. The expression of $p21^{cip}$ is significantly reduced in all WFS1-depleted cell lines compared with control cells.

FIG. 4F. The percentages of cells in G2 phase in each cell line, by $p21^{cip}$ expression.

FIG. 4G. The percentages of cells showing apoptosis in each cell line, by $p21^{cip}$ expression.

Figure 5:
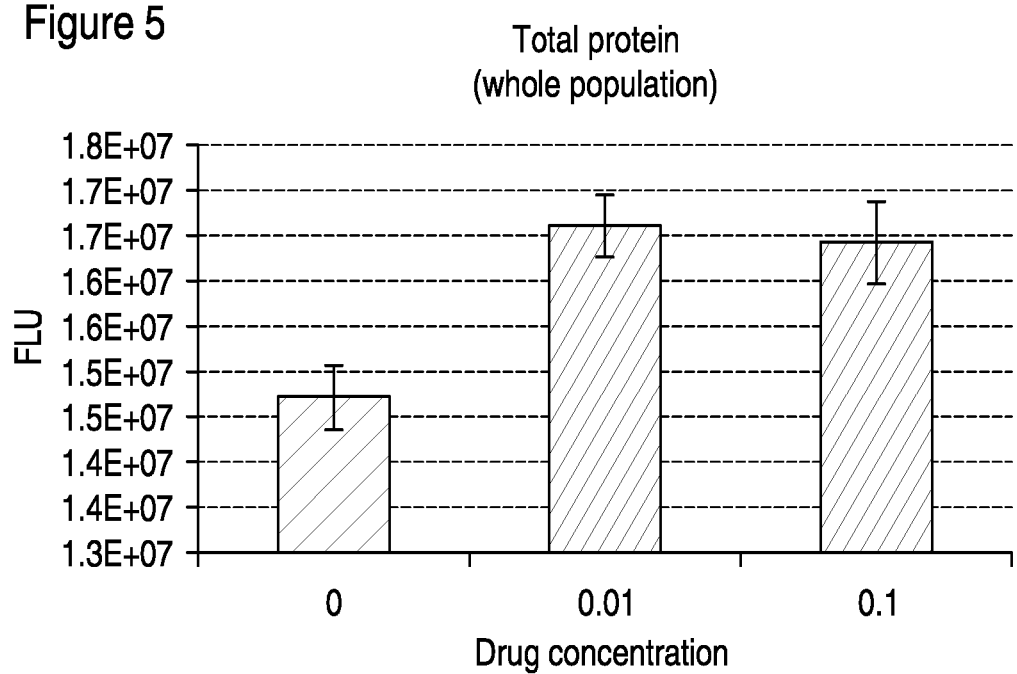
Figure 5:
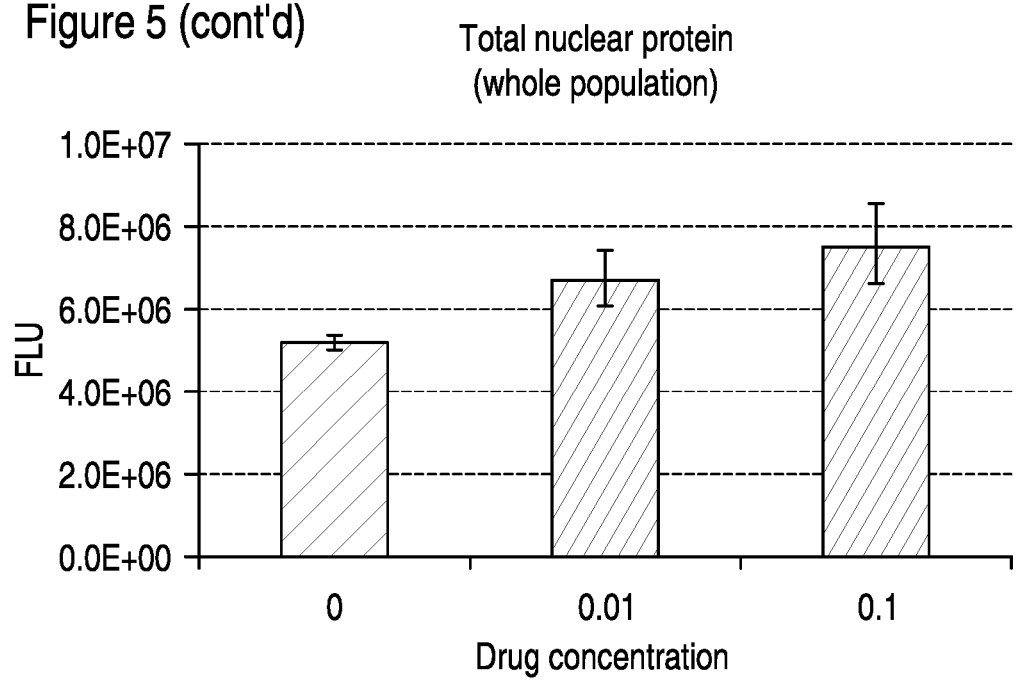
Figure 5:
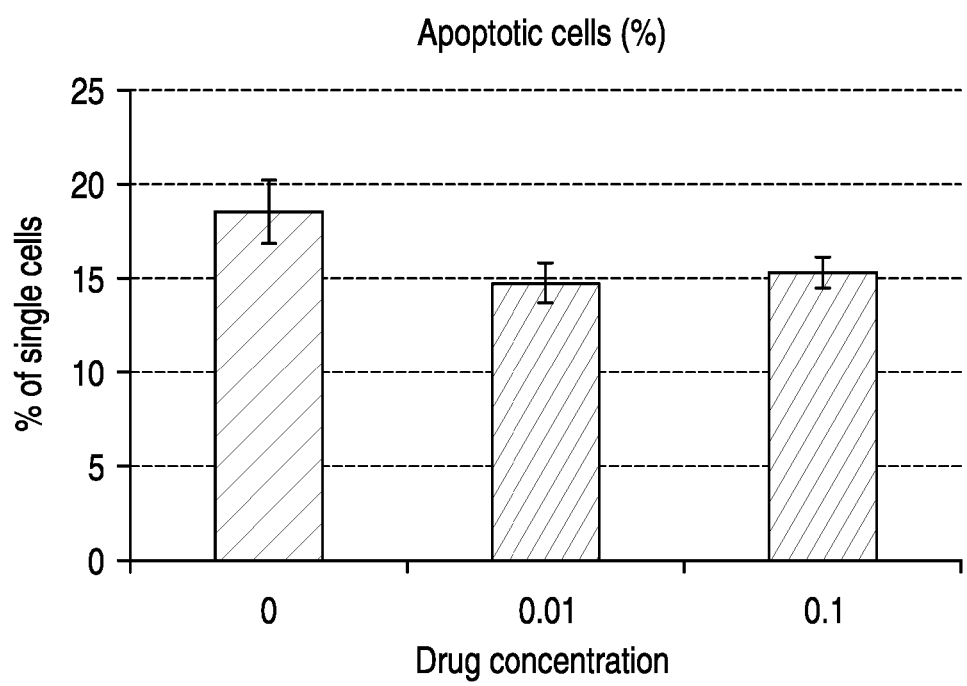

FIG. 5. The effect of Flurbiprofen on p21 expression and nuclear translocation.

FIG. 5A: P21 expression induced by Flurbiprofen as measured by fluorescent immunocytochemistry, followed by cytometry. The data below indicate that even small doses (0.01 and 0.1 microM) of Flurbiprofen applied for 24 hours can significantly increase p21 expression in neuroblastoma cells.

FIG. 5B: The increase in p21 expression (illustrated above) is parallel to the increase of p21 in the nuclear compartment (active site). The data below indicate that even small doses (0.01 and 0.1 microM) of Flurbiprofen applied for 24 hours can significantly increase p21 expression in the nuclear compartment in neuroblastoma cells.

FIG. 5C: The increased expression and nuclear translocation of p21 induced by Flurbiprofen is associated with a significant decrease in apoptotic cell death. The data below indicate that even small doses (0.01 and 0.1 microM) of Flurbiprofen applied for 24 hours can significantly reduce apoptotic cell death in neuroblastoma cells.

Figure 6:
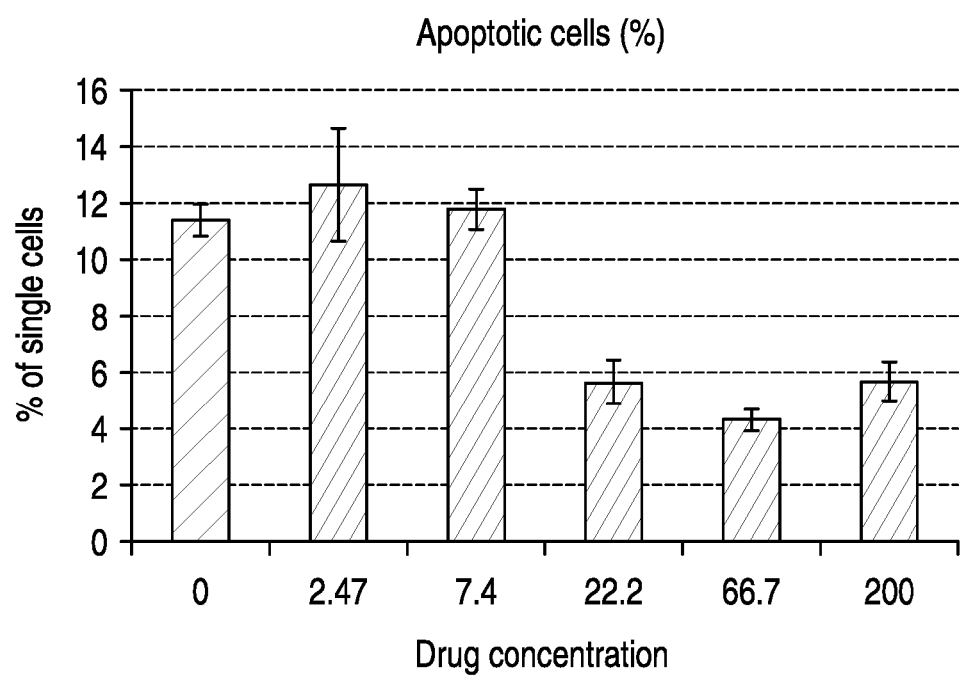
Figure 6:
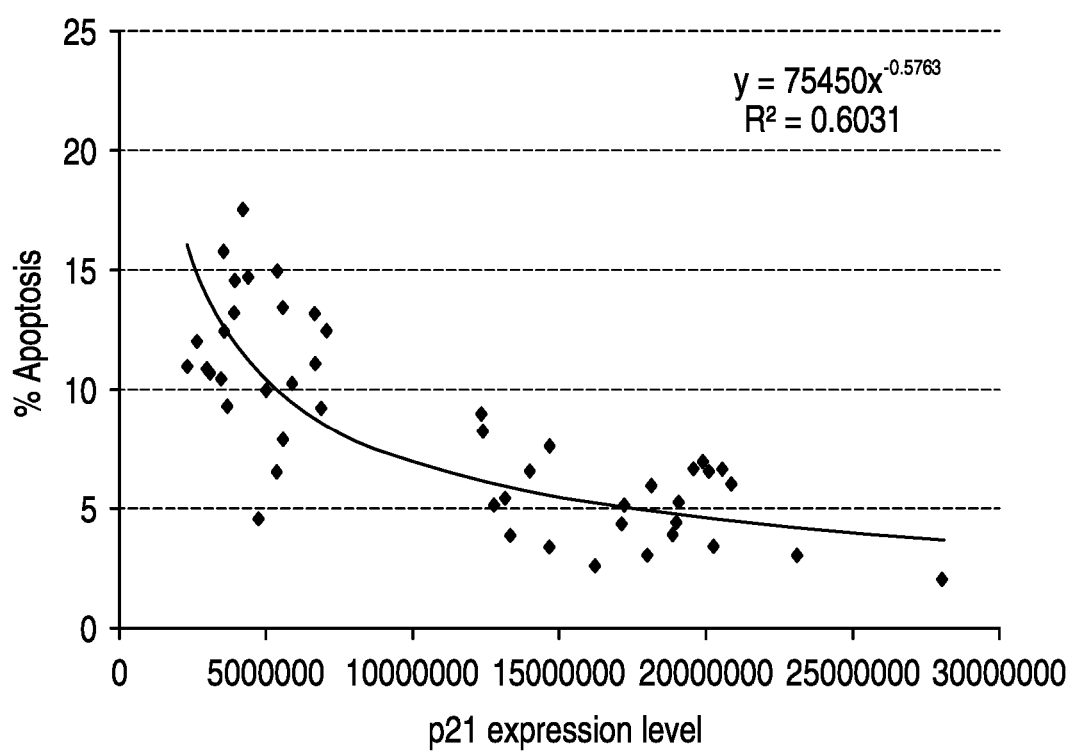

FIG. 6. The effect of Dexrazoxane on p21 expression and apoptosis.

FIG. 6A: P21 expression induced by Dexrazoxane as measured by fluorescent immunocytochemistry, followed by cytometry. The data below indicate that even small doses (up to 200 microM) of Dexrazoxane applied for 24 hours can significantly increase p21 expression in neuroblastoma cells.

FIG. 6B: P21 expression induced by Dexrazoxane is associated with significantly reduced cell death in neuroblastoma cells.

FIG. 6C: Inverse relationship between P21 expression induced by Dexrazoxane and cell death in neuroblastoma cells. The figure shows that the expression of p21 is strongly associated with a decrease in cell death.

Figure 7:
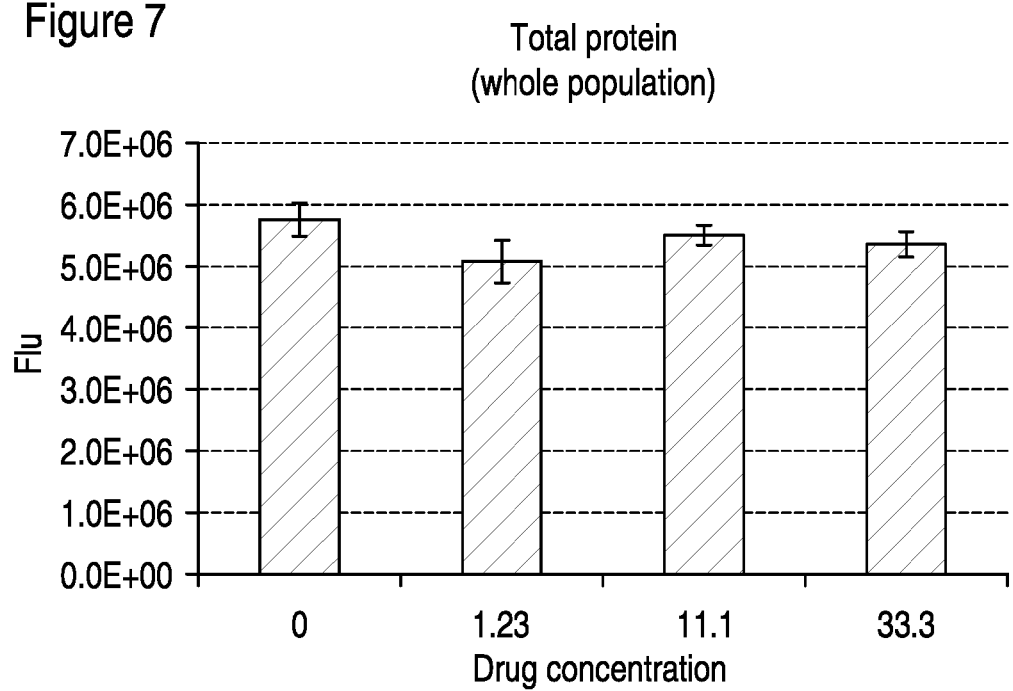
Figure 7:
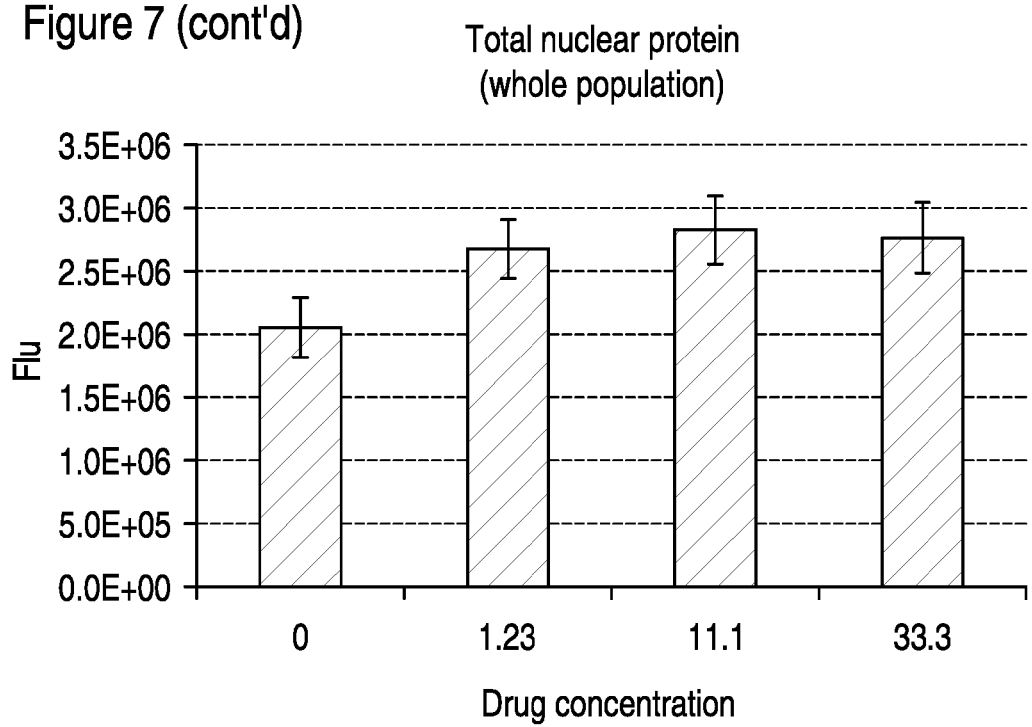
Figure 7:
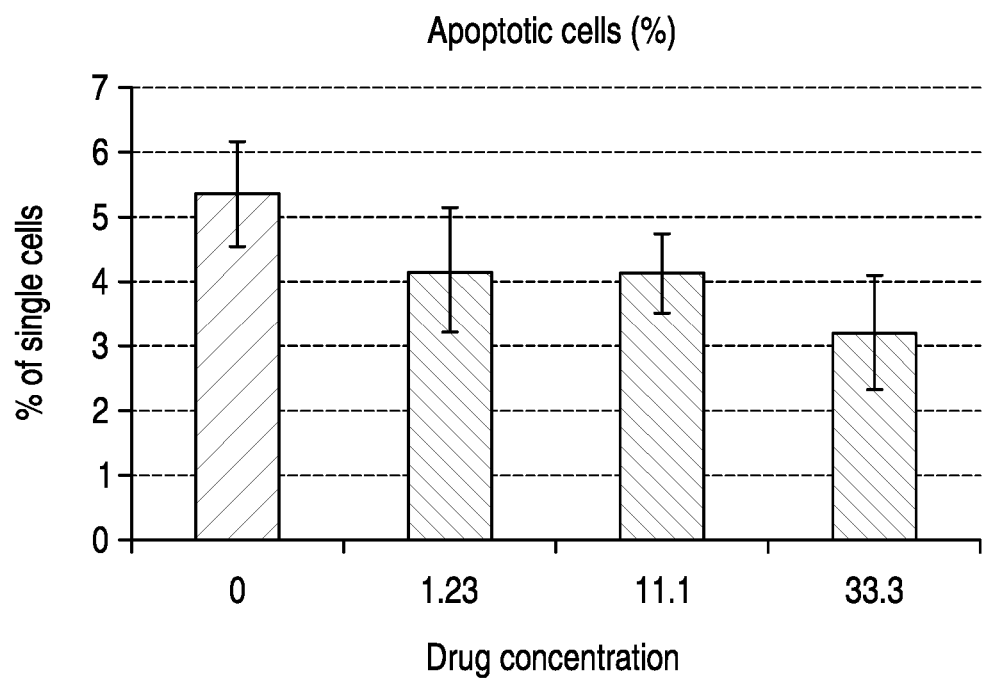

FIG. 7. The effect of Rapamycin on p21 expression and apoptosis.

FIG. 7A: P21 expression induced by rapamycin as measured by fluorescent immunocytochemistry, followed by cytometry. The data below indicate that small doses (up to 33 microM) of rapamycin applied for 24 hours do not affect p21 expression in neuroblastoma cells.

FIG. 7B: P21 expression induced by Rapamycin as measured by fluorescent immunocytochemistry, followed by cytometry. The data below indicate that although small doses (up to 33 microM) of rapamycin applied for 24 hours do not affect p21 expression in neuroblastoma cells the drug induces the increased translocation of p21 in the nucleus in neuroblastoma cells.

FIG. 7C: The increased nuclear translocation of p21 induced by Rapamycin (as above) is sufficient to induce the reduction of apoptotic cell death even in the absence of increase in P21 expression.

FIG. 8. The effect of Sodium Valproate (SV)

Figure 8A:
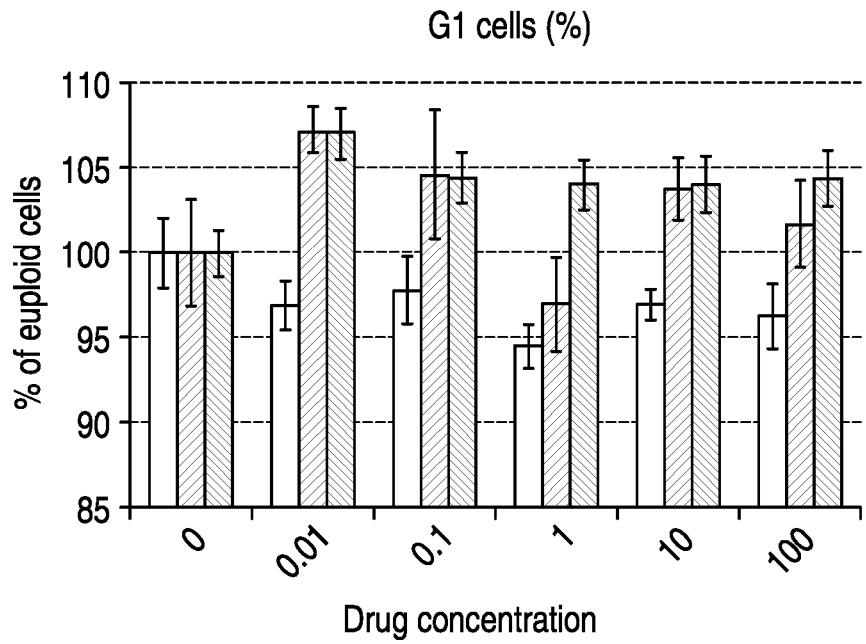
Figure 8B:
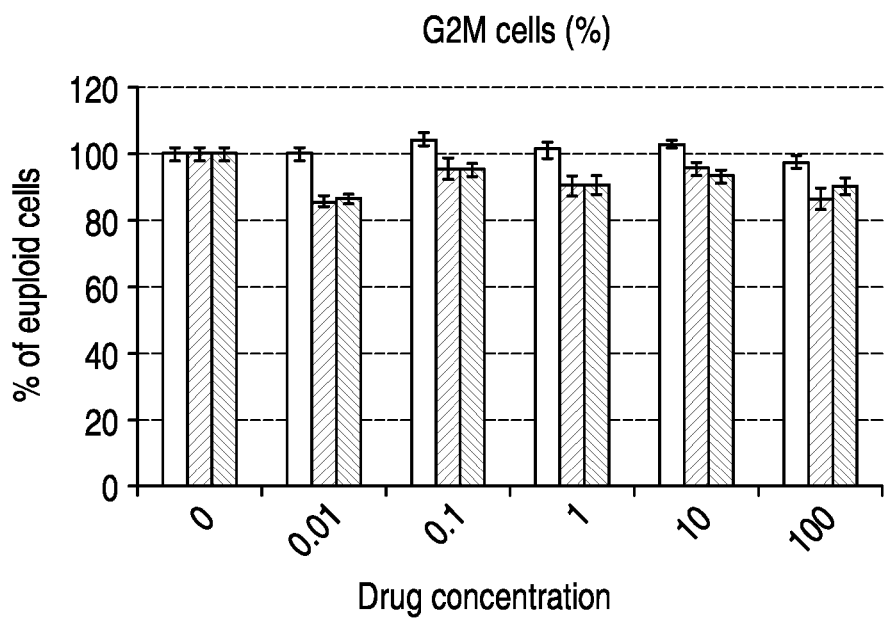

FIGS. 8A and 8B: The cell cycle effects of SV. Cell cycle kinetics alterations induced by SV in our cell lines. It is apparent that SV induces a slight G1 inhibitor effect in both the KD2 (grey bars) and KD3 (Black bars) cell line. This effect is not seen in the C7 (neuroblastoma) cell line (white bars).

Figure 8C:
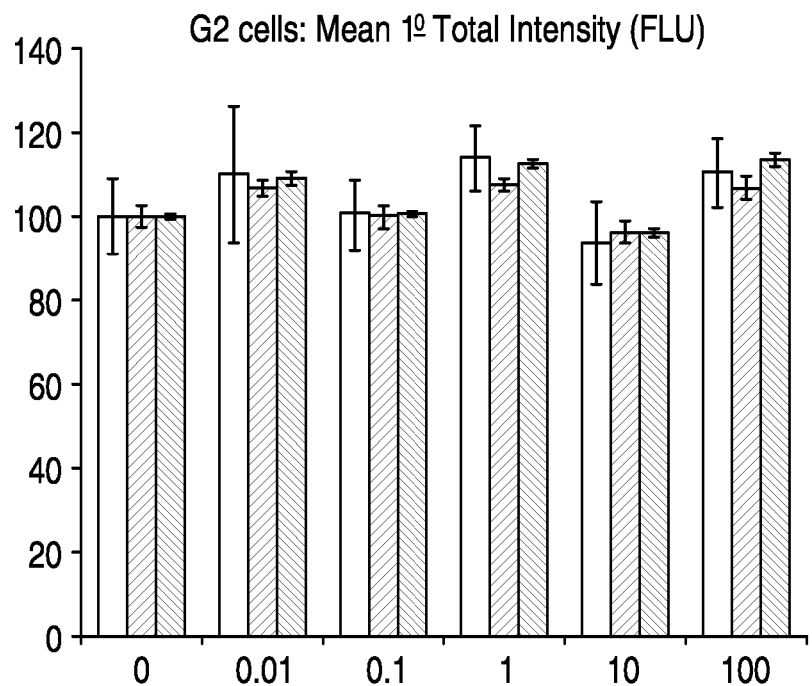

FIG. 8C: The effects of SV on $p21^{cip1}$ expression. In the G2 sub-population of cells there is a significant upregulation of p21 protein at 1 μM SV. C7 cell line: white bars; KD2 cell line: Grey bars; and KD3 cell line: black bars. Y axis represents the % change in protein expression relative to control cultures.

Figure 8D:
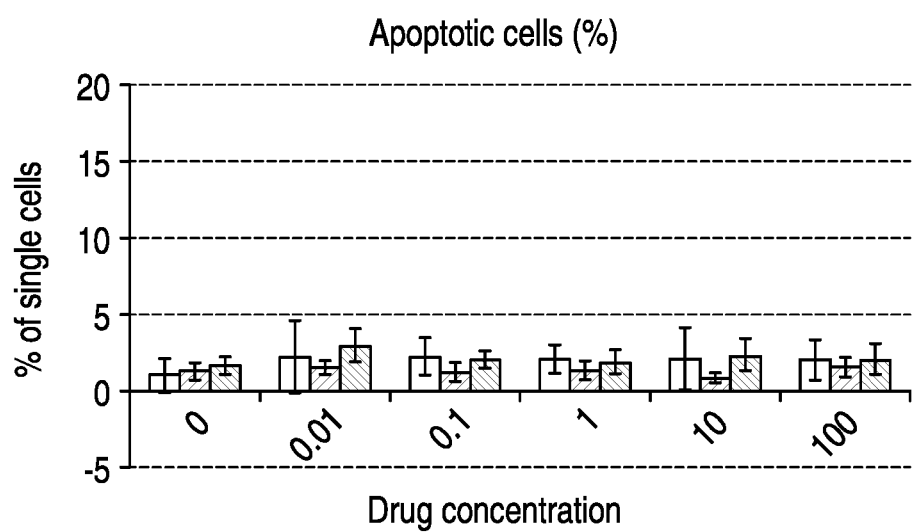

FIG. 8D: The effects of $p21^{cip1}$ expression in SV-treated cells on apoptosis. p21 expression is associated with a significant reduction of apoptotic fraction (% apoptotic in positive cells relative to p21 negative cells). C7 cell line: white bars; KD2 cell line: Grey bars; and KD3 cell line: black bars.

FIG. 9. The effect of Chloroquine diphosphate

Figure 9A:
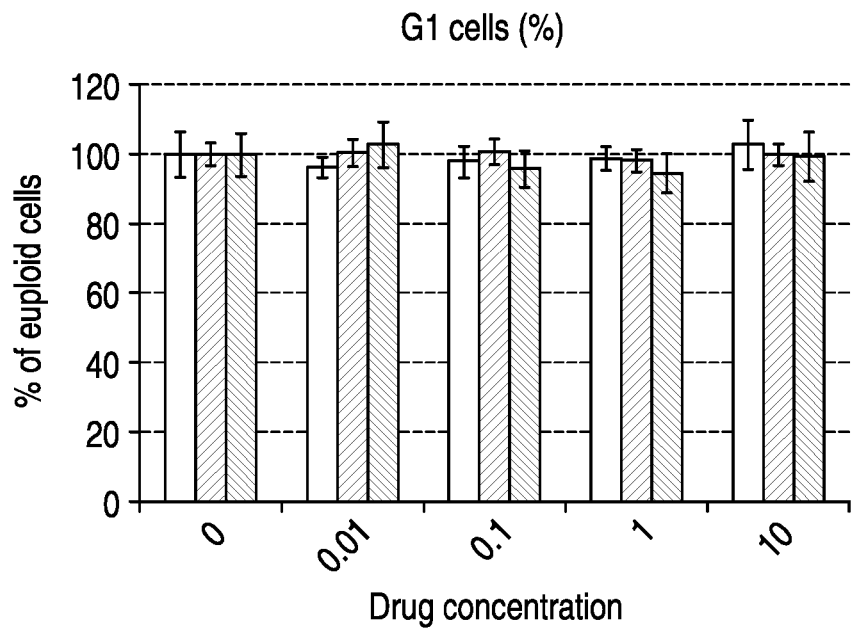
Figure 9B:
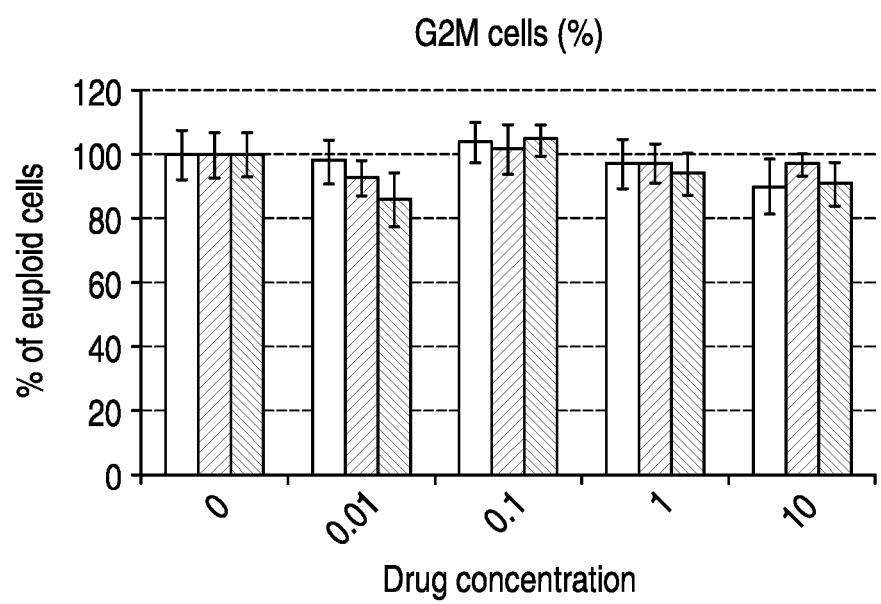

FIGS. 9A and 9B: The cell cycle effects of Chloroquine diphosphate. Chloroquine diphosphate has no significant effect on cell cycle kinetics in any of the three cell lines. C7 cell line: white bars; KD2 cell line: Grey bars; and KD3 cell line: black bars.

FIG. 9C-9F: The effects of Chloroquine diphosphate on $p21^{cip1}$ expression.

Figure 9C:
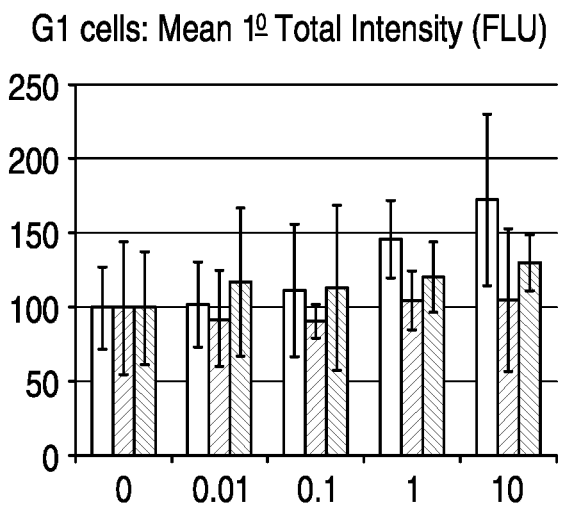
Figure 9D:
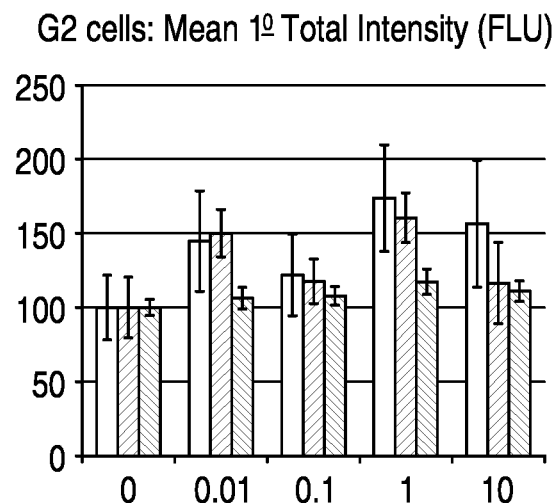
Figure 9E:
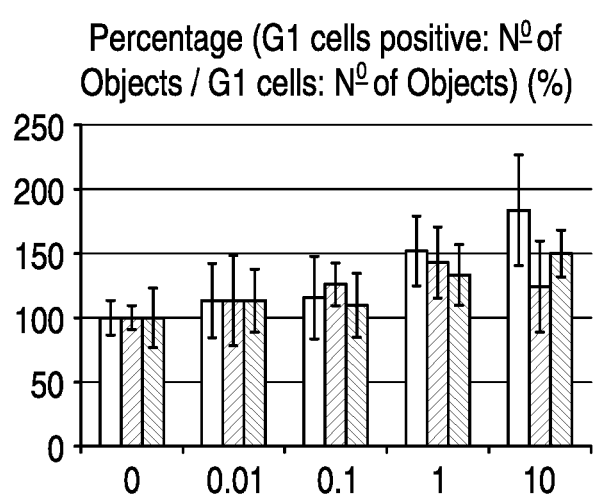
Figure 9F:
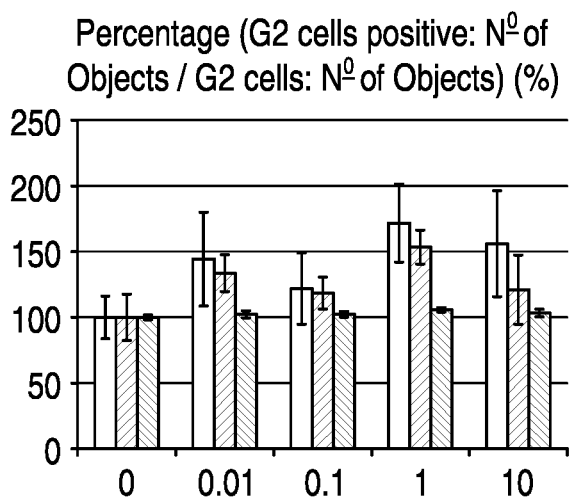

In the C7 cells p21 expression is significantly increased in both G1 and G2M (FIGS. 9C and 9D white bars) and is associated with increased proportion of protein positive cells (FIGS. 9E and 9F, white bars).

In KD2 cells the P21 is up-regulated in the G2M phase (FIG. 9D, grey bars). In the KD3 cell line the upregulation of p21 occurs in G1 (FIG. 9C, black bars). Both are associated with increased in the proportion of protein positive cells (FIGS. 9E and 9F). C7 cell line: white bars; KD2 cell line: Grey bars; and KD3 cell line: black bars. Y axis represents the % change in protein expression relative to control cultures.

Figure 9G:
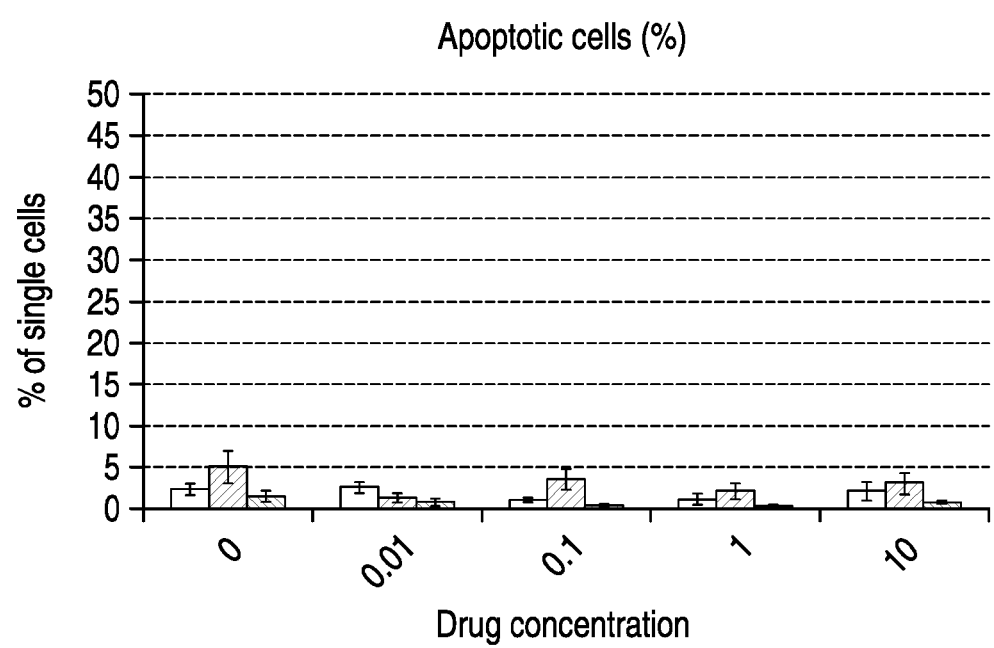

FIG. 9G: The effects of $p21^{cip1}$ expression in Chloroquine diphosphate-treated cells on apoptosis. The cells expressing p21 are significantly less likely to be apoptotic than the p21 negative cells. C7 cell line: white bars; KD2 cell line: Grey bars; and KD3 cell line: black bars.

FIG. 10. The effect of Pioglitazone

Figure 10A:
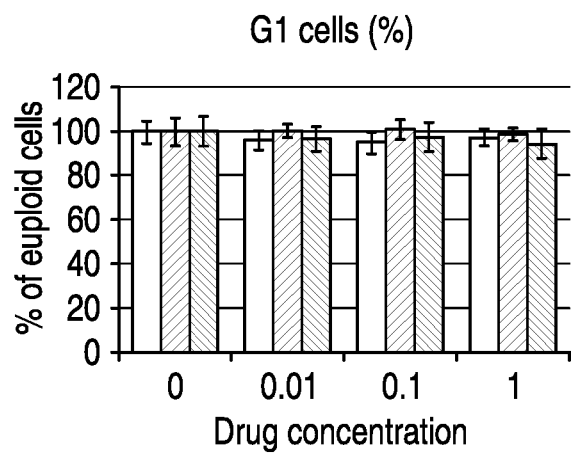
Figure 10B:
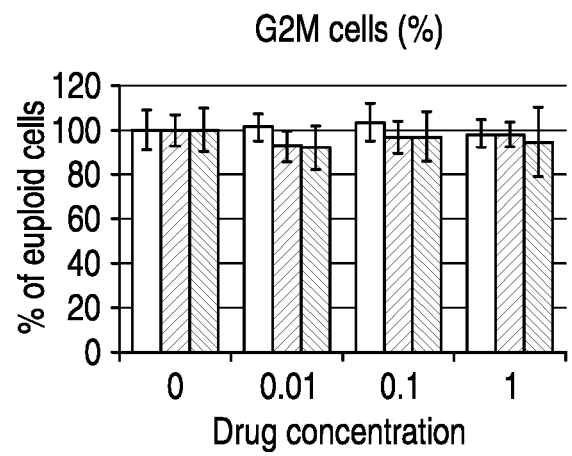

FIGS. 10A and 10B: The cell cycle effects of Pioglitazone. Pioglitazone did not have any significant cell cycle effects on all cell lines. C7 cell line: white bars; KD2 cell line: Grey bars; and KD3 cell line: black bars.

Figure 10C:
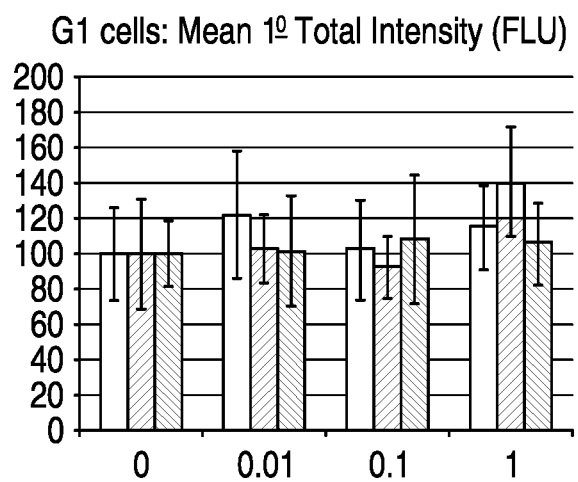
Figure 10D:
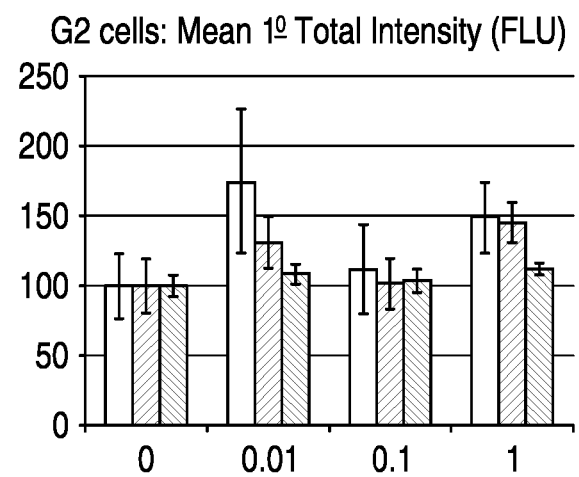

FIGS. 10C and 10D: The effects of Pioglitazone on $p21^{cip1}$ expression. p21 expression was increased by the drug in both the G1 and G2 subpopulations, albeit this induction is cell type dependent and are most modest in the KD3 cell line. C7 cell line: white bars; KD2 cell line: Grey bars; and KD3 cell line: black bars. Y axis represents the % change in protein expression relative to control cultures.

Figure 10E:
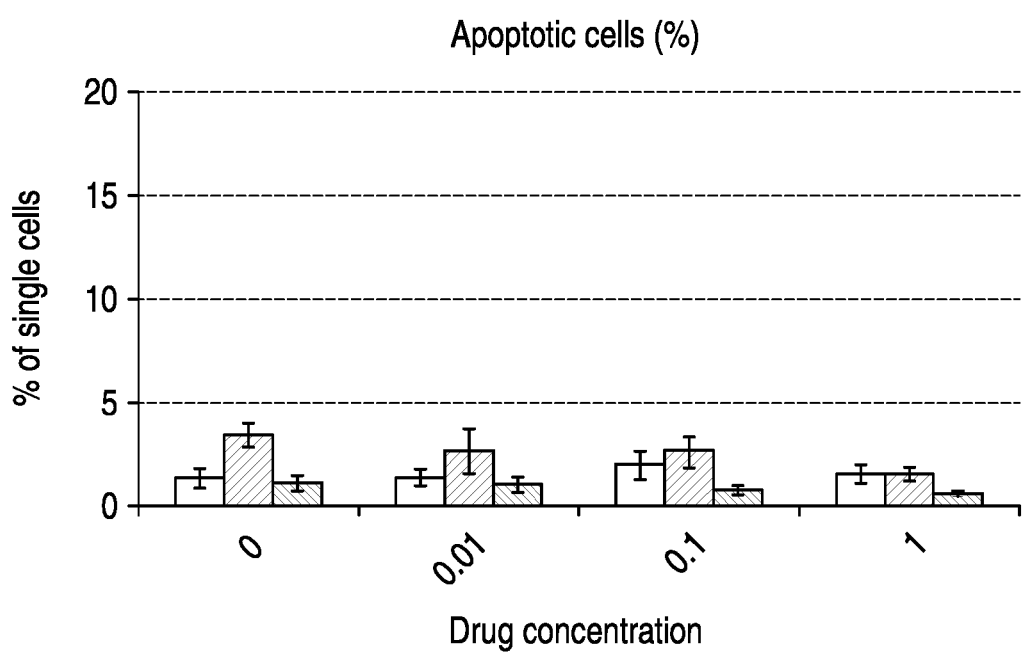

FIG. 10E: The effects of $p21^{cip1}$ expression in Pioglitazone-treated cells on apoptosis. Apoptosis was significantly reduced in protein positive cells relative to negative cells in all three cell lines. C7 cell line: white bars; KD2 cell line: Grey bars; and KD3 cell line: black bars.

FIG. 11. The effect of Sodium 4-phenylbutyrate (4-PBA)

Figure 11A:
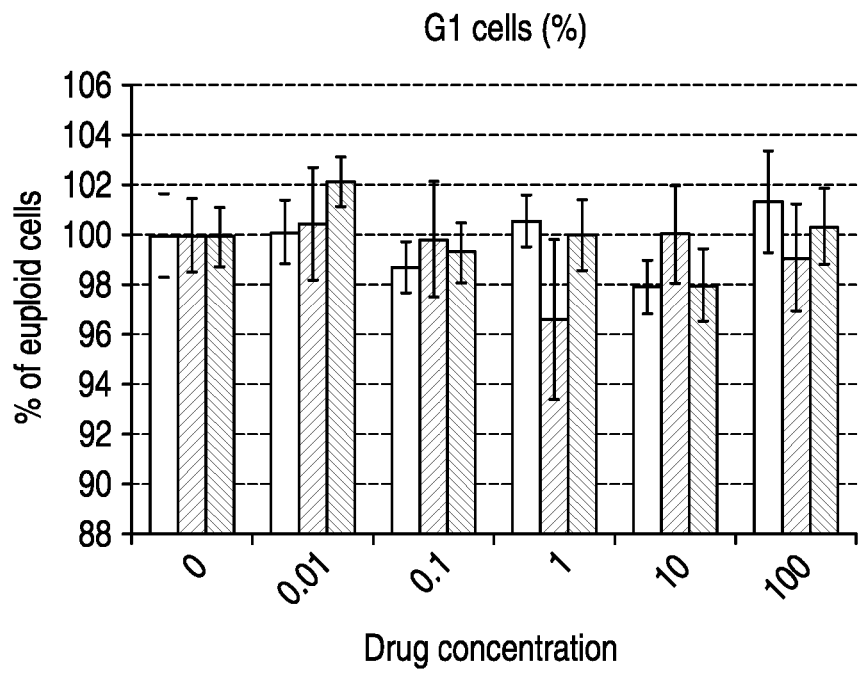
Figure 11B:
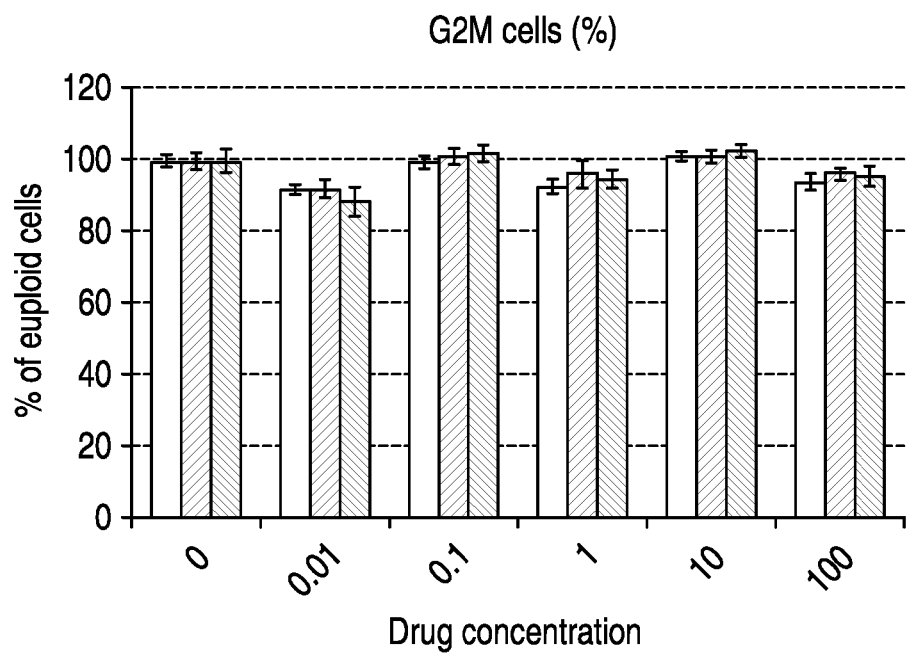

FIGS. 11A and 11B: The cell cycle effects of Sodium 4-phenylbutyrate. 4-PBA has no effects on cell cycle in all three cell lines. C7 cell line: white bars; KD2 cell line: Grey bars; and KD3 cell line: black bars.

Figure 11C:
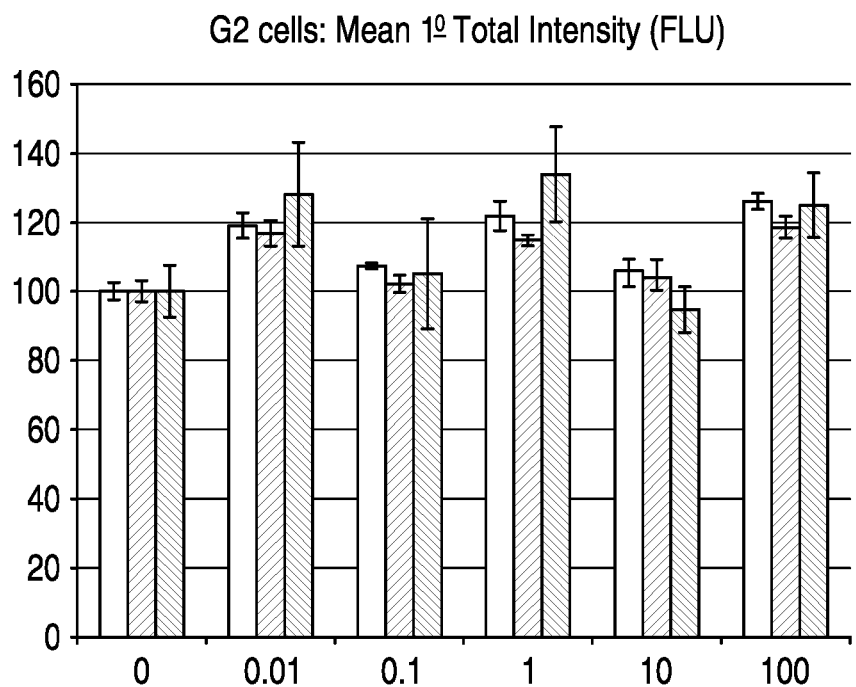

FIG. 11C: The effects of Sodium 4-phenylbutyrate on $p21^{cip1}$ expression. The drug induces p21 expression in the G2 cell population in all three cell lines. C7 cell line: white bars; KD2 cell line: Grey bars; and KD3 cell line: black bars. Y axis represents the % change in protein expression relative to control cultures.

Figure 11D:
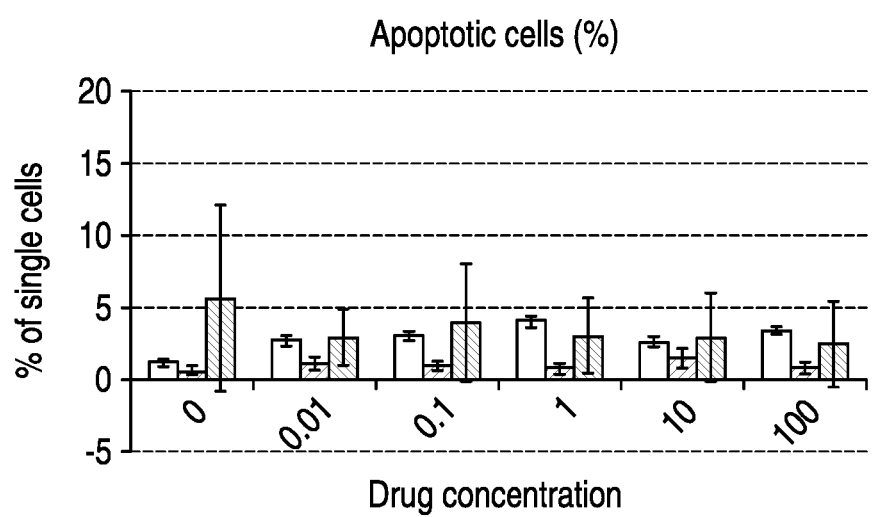

FIG. 11D: The effects of $p21^{cip1}$ expression in Sodium 4-phenylbutyrate-treated cells on apoptosis. P21 expression is associated with significantly reduced apoptosis in all three cell lines. C7 cell line: white bars; KD2 cell line: Grey bars; and KD3 cell line: black bars.

FIG. 12. The effect of Fusidic acid

Figure 12A:
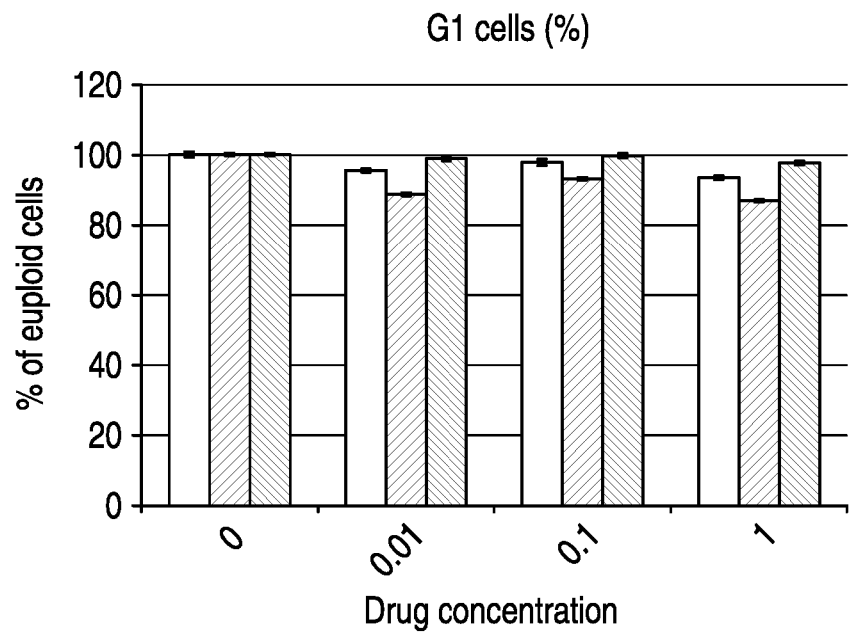
Figure 12B:
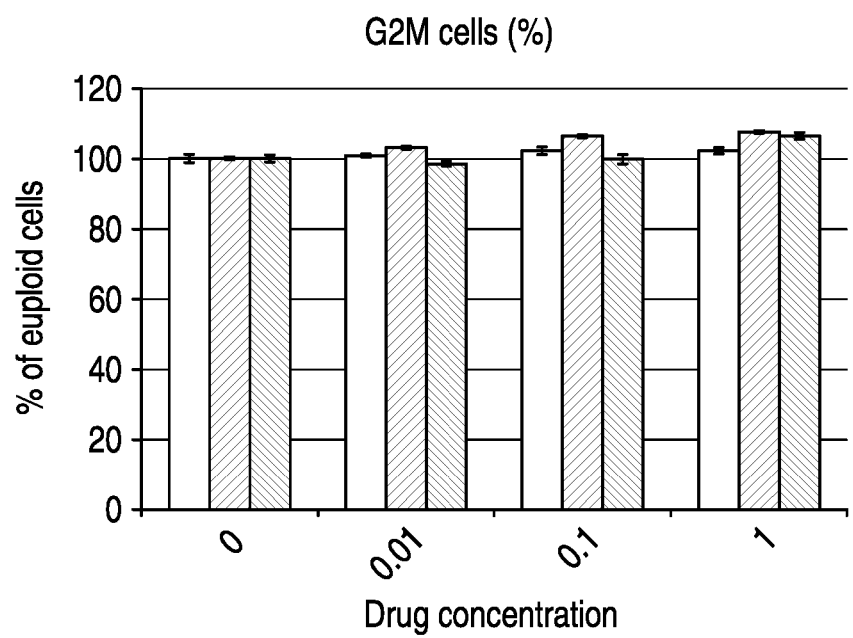

FIGS. 12A and 12B: The cell cycle effects of Fusidic acid. We found that fusidic acid is a weak G2 inhibitor in all three cell lines. C7 cell line: white bars; KD2 cell line: Grey bars; and KD3 cell line: black bars.

Figure 12C:
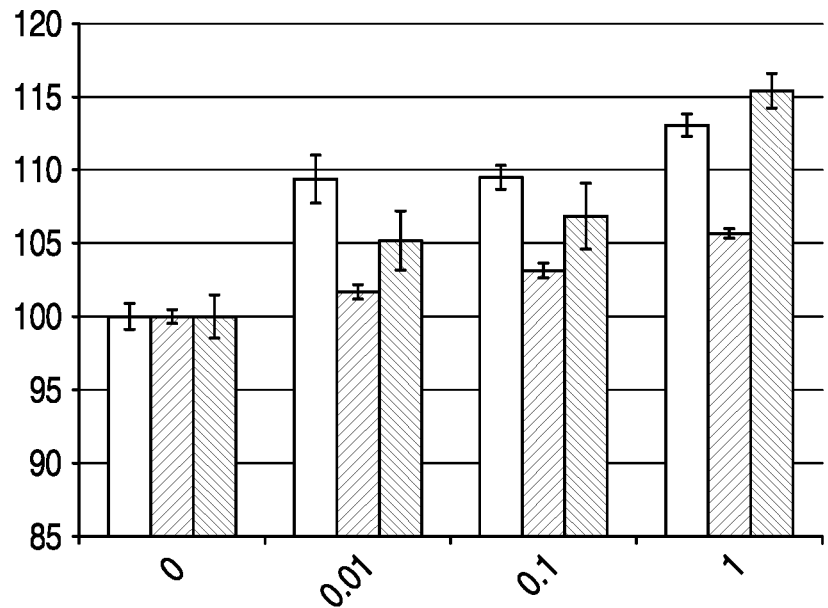

FIG. 12C: The effects of Fusidic acid on p21$^{cip1}$ expression. The drug leads to a significant increase in p21 expression in all cell lines. C7 cell line: white bars; KD2 cell line: Grey bars; and KD3 cell line: black bars. Y axis represents the % change in protein expression relative to control cultures.

Figure 12D:
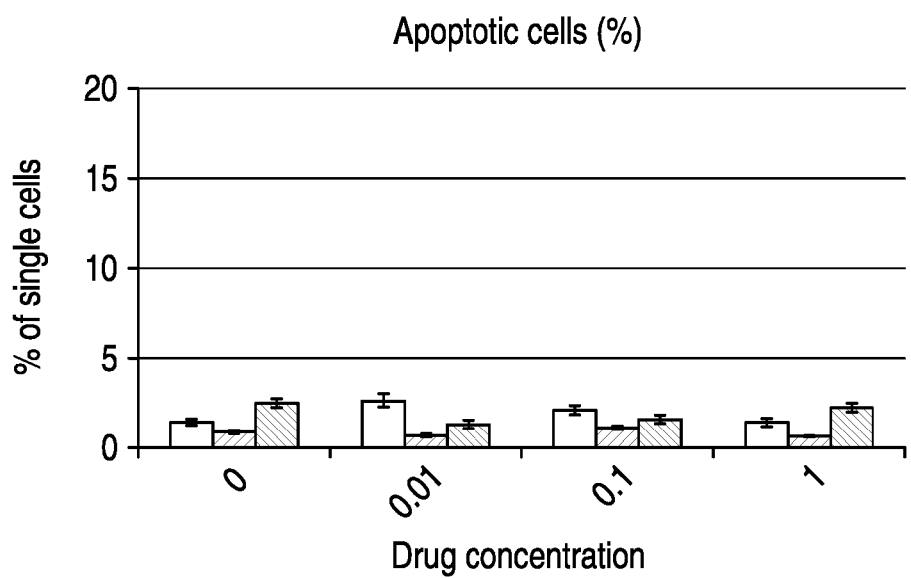

FIG. 12D: The effects of p21$^{cip1}$ expression in Fusidic acid-treated cells on apoptosis. P21 expression is associated with the reduction of apoptosis in the positive cells. C7 cell line: white bars; KD2 cell line: Grey bars; and KD3 cell line: black bars.

FIG. 13. The effect of Ciclopirox Olamine (CPX)

Figure 13A:
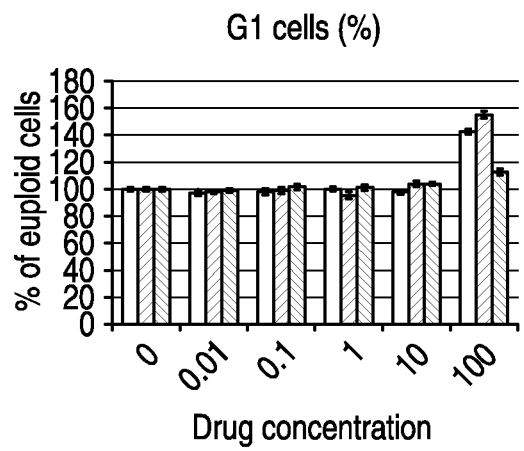
Figure 13B:
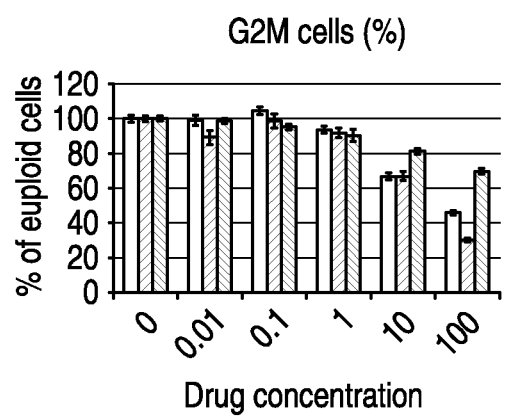

FIGS. 13A and 13B: The cell cycle effects of CPX. In all cell lines CPX was found to induce a slight G1 cell cycle arrest in the expense of G2M phase. C7 cell line: white bars; KD2 cell line: Grey bars; and KD3 cell line: black bars.

Figure 13C:
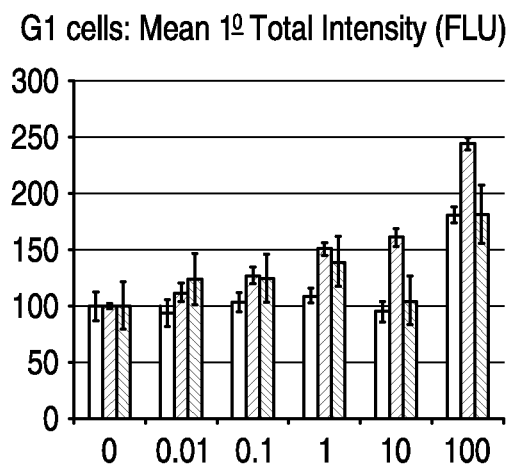
Figure 13D:
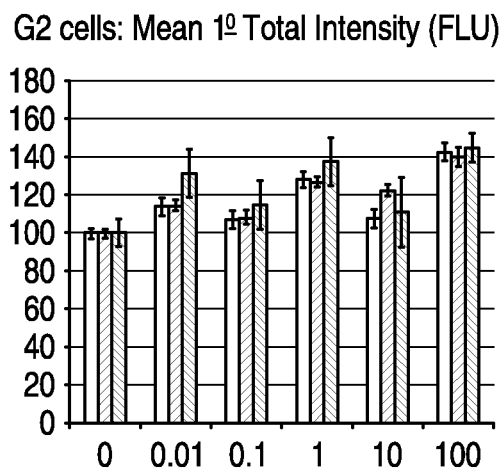

FIGS. 13C and 13D: The effects of CPX on p21$^{cip1}$ expression. In all cell lines CPX induces significant p21 expression in both the G1 and G2 phase populations. C7 cell line: white bars; KD2 cell line: Grey bars; and KD3 cell line: black bars. Y axis represents the % change in protein expression relative to control cultures.

Figure 13E:
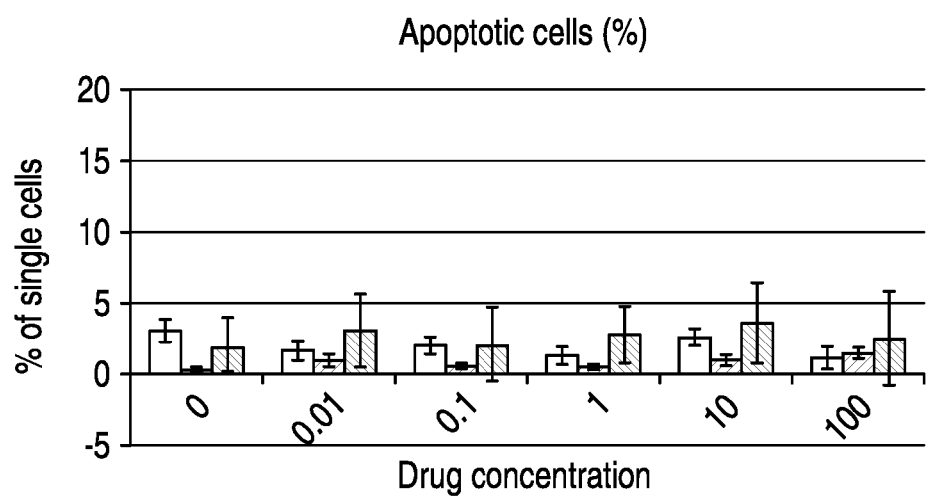

FIG. 13E: The effects of p21$^{cip1}$ expression in CPX-treated cells on apoptosis. P21 expression is associated with a significant reduction of apoptotic cells. C7 cell line: white bars; KD2 cell line: Grey bars; and KD3 cell line: black bars.

FIG. 14. The effect of Dapsone

Figure 14A:
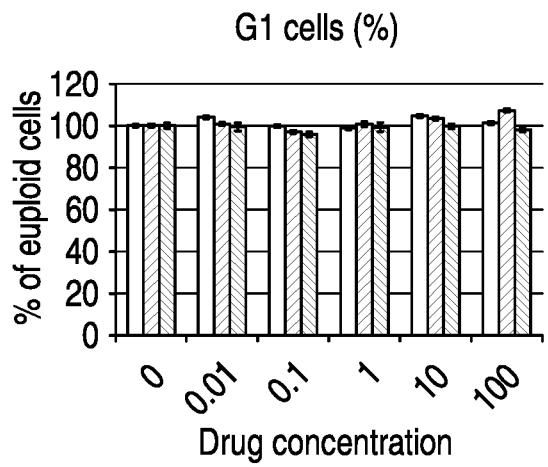
Figure 14B:
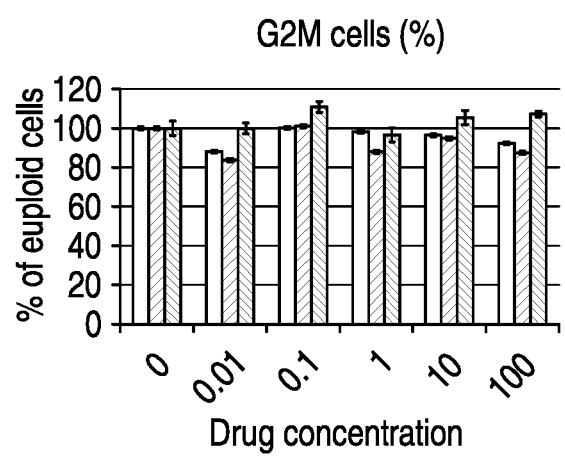

FIGS. 14A and 14B: The cell cycle effects of Dapsone. No cell cycle effects were observed following Dapsone treatment. C7 cell line: white bars; KD2 cell line: Grey bars; and KD3 cell line: black bars.

Figure 14C:
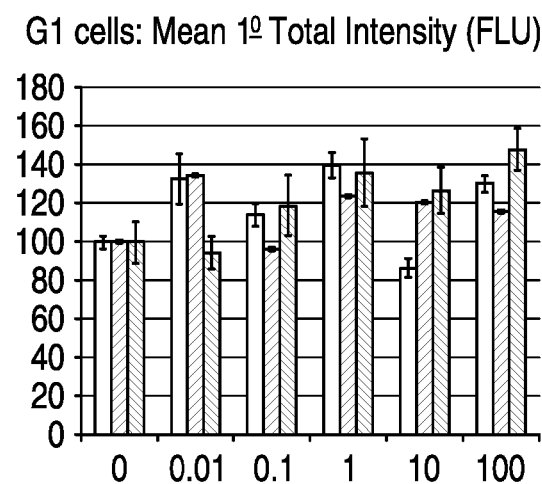
Figure 14D:
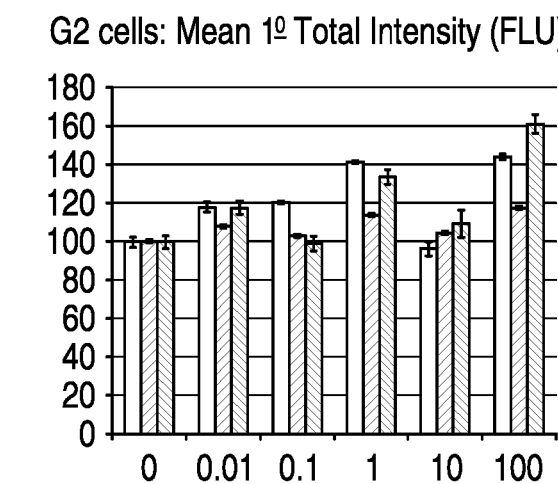

FIGS. 14C and 14D: The effects of Dapsone on p21$^{cip1}$ expression. Dapsone significantly up-regulates p21 expression in all three cell lines. C7 cell line: white bars; KD2 cell line: Grey bars; and KD3 cell line: black bars. Y axis represents the % change in protein expression relative to control cultures.

Figure 14E:
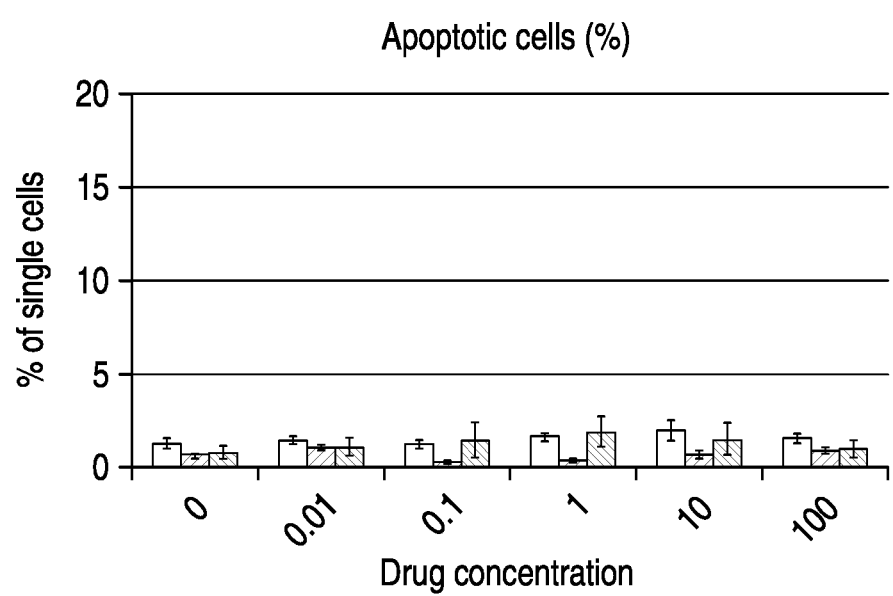

FIG. 14E: The effects of p21$^{cip1}$ expression in Dapsone-treated cells on apoptosis. P21 expression is associated with a significant reduction of apoptotic cells. C7 cell line: white bars; KD2 cell line: Grey bars; and KD3 cell line: black bars.

FIG. 15. The effect of Rifampicin

Figure 15A:
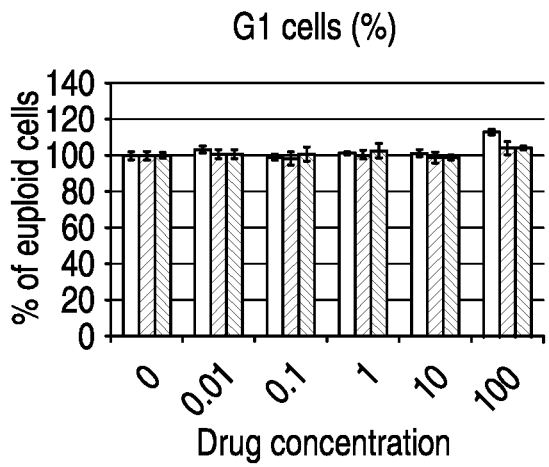
Figure 15B:
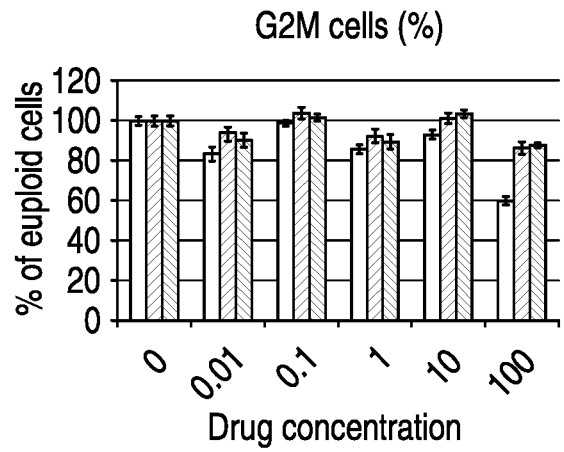

FIGS. 15A and 15B: The cell cycle effects of Rifampicin. Rifampicin did not exert cell cycle effects in all cell lines. C7 cell line: white bars; KD2 cell line: Grey bars; and KD3 cell line: black bars.

Figure 15C:
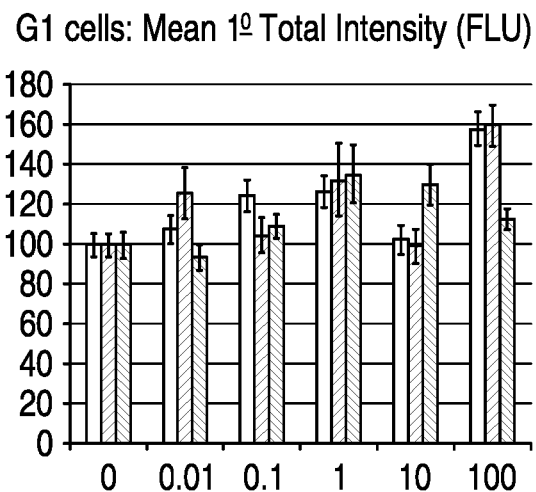
Figure 15D:
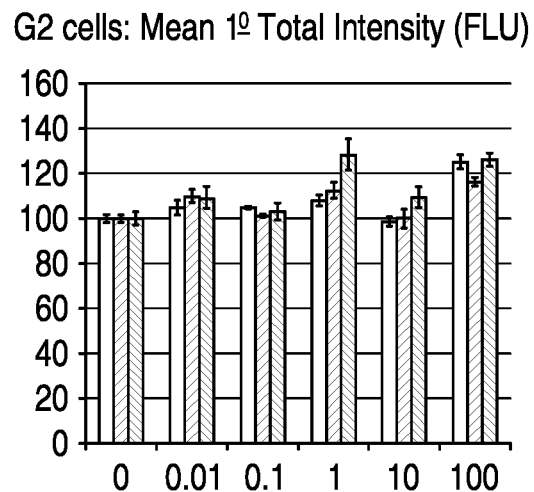

FIGS. 15C and 15D: The effects of Rifampicin on p21$^{cip1}$ expression. Rifampicin up-regulates p21 expression in both the control (C7) and WFS1 deficient cell lines. C7 cell line: white bars; KD2 cell line: Grey bars; and KD3 cell line: black bars. Y axis represents the % change in protein expression relative to control cultures.

Figure 15E:
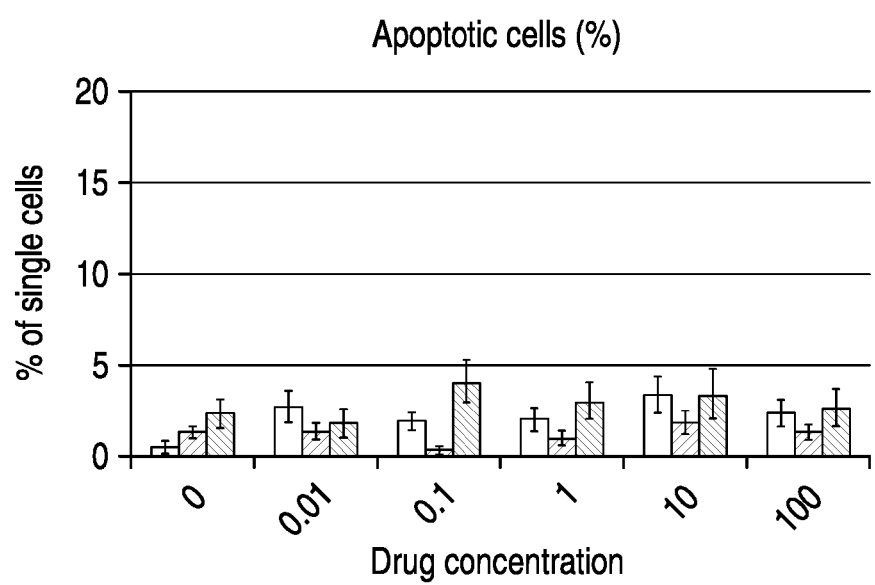

FIG. 15E: The effects of p21$^{cip1}$ expression in Rifampicin-treated cells on apoptosis. In all cultures the p21 expression is associated with a significant reduction of apoptosis. C7 cell line: white bars; KD2 cell line: Grey bars; and KD3 cell line: black bars.

FIG. 16. The effect of Loperamide hydrochloride

Figure 16A:
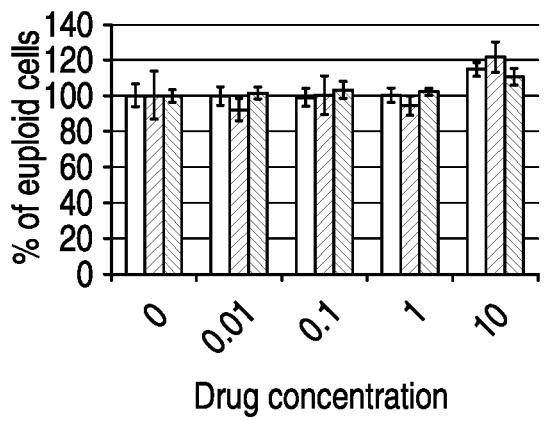
Figure 16B:
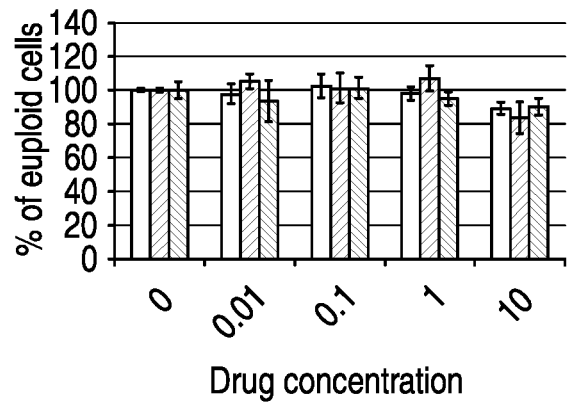

FIGS. 16A and 16B: The cell cycle effects of Loperamide hydrochloride. Loperamide was found to be a weak G1 inhibitor in all cell lines. C7 cell line: white bars; KD2 cell line: Grey bars; and KD3 cell line: black bars.

Figure 16C:
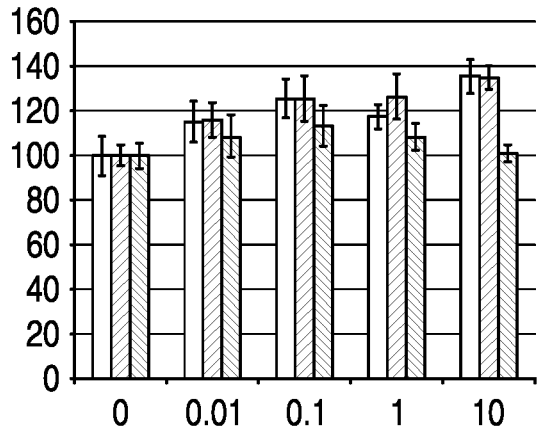
Figure 16D:
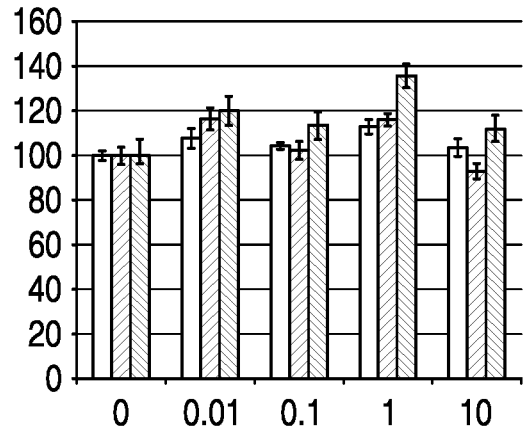

FIGS. 16C and 16D: The effects of Loperamide hydrochloride on p21$^{cip1}$ expression. Loperamide induce p21 expression in all three cell lines in both the G1 and G2 cell populations. C7 cell line: white bars; KD2 cell line: Grey bars; and KD3 cell line: black bars. Y axis represents the % change in protein expression relative to control cultures.

Figure 16E:
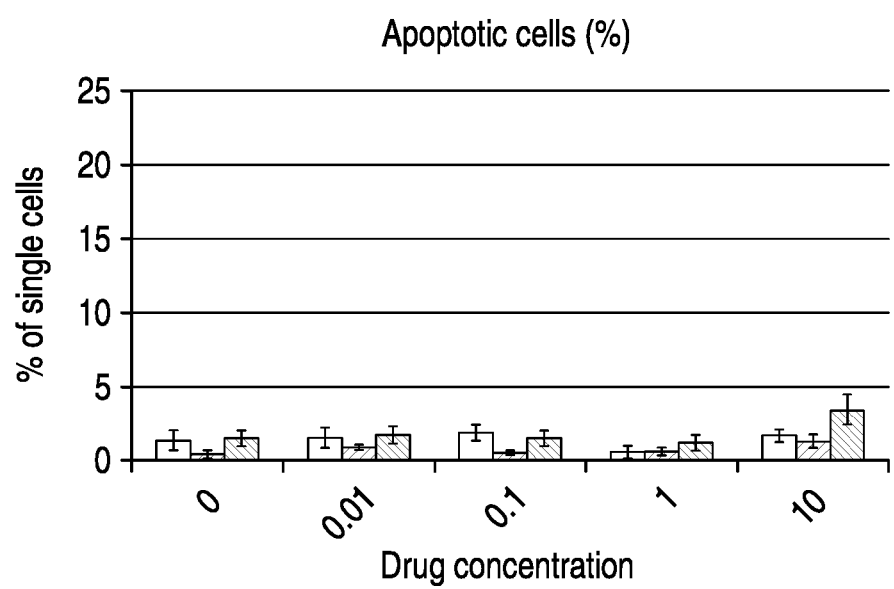

FIG. 16E: The effects of p21$^{cip1}$ expression in Loperamide hydrochloride-treated cells on apoptosis. P21 expression is associated with a significant reduction of apoptosis. C7 cell line: white bars; KD2 cell line: Grey bars; and KD3 cell line: black bars.

DETAILED DESCRIPTION OF THE INVENTION

Neurodegeneration is a heterogeneous disorder characterised by the progressive loss of structure, function, and death of neurons, and is estimated to affect 1800 per 100,000 of the US population (1). Common contributing factors include genetic mutations, disorders of protein folding or protein degradation, and disrupted apoptotic pathways.

Wolfram syndrome (WS) is a single gene neurodegenerative disorder mediated via ER stress, and characterised by childhood onset diabetes mellitus, optic atrophy, and motor, sensory and autonomic nervous system disruption (2). Many patients die prematurely with severe neurological disabilities such as central sleep apneas and organic brain syndrome (2). Imaging and post mortem studies have shown diffuse neurodegenerative changes in the brain (3). The causative gene, WFS1, was cloned in 1998 (4,5) and encodes an ER membrane protein, WFS1 protein or Wolframin (6), which contains 9 transmembrane domains. Mice with disrupted WFS1 exhibit progressive pancreatic beta cell loss, resulting from activation of ER stress pathways, delayed cell cycle progression and apoptosis (7-9). Wolframin expression is high in mouse and rat brain in the hippocampus CA1, amygdaloid areas, olfactory tubercles, cerebellum and superficial layer of the allocortex (10,11). This expression pattern correlates with the cerebellar ataxia, psychiatric, and behavioural abnormalities seen in both humans and mouse models of Wolfram syndrome (12-14).

Recently it was shown that WFS1 plays a key role in the negative regulation of a feedback loop of the ER stress network through the ubiquitin proteasome pathway (15). We have previously shown that the Na$^+$/K$^+$ ATPase beta1 subunit (ATP1B1) is a molecular partner of Wolframin, and WFS1 deficiency resulted in reduced expression of ATP1B1 (16). The mature sodium pump is located in the plasma membrane; however during maturation it is transiently present in the ER. Recently it was shown that WFS1 is additionally located in the secretory granules of pancreatic beta cells and plays a role in granule acidification (17). Secretory granules are acidified through a proton gradient established and maintained by H$^+$ vacuolar type ATPase (V-ATPase).

In this study, WFS1-depleted human neuroblastoma cells (KD1, KD2 and KD3) demonstrated increased ER stress response proteins and apoptosis relative to control (FIG. 1). We also demonstrate that BiP overexpression in the WFS1 depleted cell lines rescue the cells from ER stress and cell death (FIGS. 1, and 2). These data indicate that our WFS1-depleted neuronal cell lines represent the known phenomena that occur in WS and are responsible (via unknown mechanisms) for the neuronal death associated with the disease. Thus these cell lines represent an in vitro model for WS-related neurodegeneration.

Accordingly, we show herein that an increased p21 expression and/or functional activity leads to a reduced neuronal apoptosis (i.e. reduced neuron cell death) and correction of the cell cycle deficiency in WFS1 depleted cell lines.

It is noted that the terms p21 and p21"cip1" are used interchangeably herein. There are number of 21 amino acid peptides denoted p21, but it will be appreciated that reference herein is to p21 in respect of CDK-INTERACTING PROTEIN 1, Other names for the same gene include: CYCLIN-DEPENDENT KINASE INHIBITOR 1A; CDKN1A; CDK-INTERACTING PROTEIN 1; CIP1; WILDTYPE p53-ACTIVATED FRAGMENT 1; and WAF1. The HGNC Approved Gene Symbol is: CDKN1A. A full description is provided at: http://omim.org/entry/116899?search=p21cip1&highlight=p21cip1

The primary clinical effect of the use of the present compounds will be 'prevention' of further neuronal death in a patient. Although the present compounds and will not be able to reverse what neuronal death that has already occurred, treatment of the condition is till possible as it is not necessarily restricted to the reversal of a pathological phenomenon. The neurones that are rescued from (otherwise certain) death are then able to function normally. One advantage of this is that they are able to continue to establish new connections (as they would do normally in the nervous system) and, thus, they can slowly start compensating for functions that were previously lost as they were fulfilled by the dead neurones.

In other words, use of compounds that are capable of increasing the expression and/or functional activity of p21 leads to relief of the symptoms of neuronal death over time. In other words, such symptoms will be alleviated. This scenario is especially the case with the induction or activation of p21, since the molecule, besides preventing neuronal death, is also known to promote the establishment of new connections between neurones (synaptogenesis) and the survival of new neurons generated in the nervous system (neurogenesis). Thus the use of use of compounds that are capable of increasing the expression and/or functional activity of p21 preferably induces or promotes synaptogenesis and/or neurogenesis.

Preferred compounds for use in the invention are provided herein: Table 4: Compounds able to affect p21 expression and activation.

We tested a number of known compounds showing an increase in the expression and/or functional activity of p21 for their effects on cell death in neuronal cells. Suitable in vitro doses are provided in Example 2 and in vivo doses may be extrapolated therefrom. Accordingly, it is preferred that an effective therapeutic dose is provided to the patient. A preferred minimum is the minimum therapeutically effective amount, which be easily determined by starting off with doses several orders of magnitude lower than the maximum and gradually increasing the dose until a therapeutic effect is seen. Preferred maximum dosages already approved for these compounds are provided below:

Flurbiprofen dose: up to a maximum of 1 mg/kg, preferably delivered orally;

Rapamycin (Sirolimus) dose: up to a maximum of 1 mg per square meter of body surface area via known methods of delivery;

Dexrazoxane: up to a maximum of 300 mg per square meter of body surface area via known methods of delivery.

We have also found that the following compounds are effective: Valproic acid or a salt thereof (in particular Sodium Valproate); Chloroquine diphosphate; Pioglitazone; 4-phenylbutyric acid (4-PBA), or a salt thereof (in particular, Sodium 4-phenylbutyrate); Fusidic acid; Ciclopirox Olamine (CPX); Dapsone (4-Aminophenyl sulfone); Rifampicin; and Loperamide or a derivative thereof, such as Loperamide hydrochloride.

Each of these 12 groups or individual compounds can be used alone. Preferably, one or mare may be used, such that preferred combinations may include 2 of these; 3 of these or 4 of these. As such, it will be appreciated that any of the compounds listed above can be used in combination with one or more of the other compounds.

Variants of the reference compound are preferred. In particular variants (including analogues) having at least 50% and more preferably at least 75%, more preferably at least 85%, more preferably at least 95%, more preferably at least 100%, more preferably at least 110%, more preferably at least 120%, more preferably at least 150%, more preferably at least 170%, more preferably at least 200%, more preferably at least 250%, more preferably at least 300%, of the activity of the reference compound are preferred.

Thus, the present invention relates to increasing the expression and/or functional activity of p21 for treating neurodegenerative disease. In particular, it is useful in treating Wolfram Syndrome (WS)-related neurodegeneration. More particularly, we have identified a number of candidates that have not previously been shown to have any effect in treating this complex disease. This is in contrast to our own intermediate publication (Human Molecular Genetics, 2013, Vol. 22, No. 2 203-217), dated 3 Oct. 2012 only relates to p21 down-regulation in WSF1-depleted cells. This document (by the present inventors) does, however, provide further useful guidance on methods in this field and to that extent is hereby incorporated by reference.

Example 1

Role of p21 in WSF-Depleted Cells

Materials and Methods
Cell Culture and Transfection:

Stably depleted WFS1 clones were prepared in human neuroblastoma cell line SK-NA-S using shRNA (Open Biosystems) and selected in medium containing puromycin at 2.5 µg/ml. SK-N-AS cell line and stably depleted clones were grown in DMEM (4500 mg/l L-glucose, L-glutamine and pyruvate, Invitrogen) supplemented with 10% FCS, penicillin (100 units/mil), streptomycin (100 µg/ml), glutamine and non-essential amino acids. The NT2 cells were grown in DMEM: F12 HAM media (SIGMA) supplemented with 10% FCS, penicillin (100 units/mil), streptomycin (100 µg/ml) and L-glutamine. The HEK293 cells were grown in DMEM (as above) with 10% FCS and penicillin and streptomycin.

Transient gene silencing was performed using small interfering RNA (siRNA, Ambion) with two oligonucleotides (WFS1-57 and WFS1-58; targeting different regions of WFS1), at final concentration 8 nM. The transfection was performed using Interferin transfection reagent (Source Biosciences) according to manufacturer's instructions. Cells were harvested for expression studies 72 hours after transfection. The same procedure was used for SK-N-AS and NT2 cell lines.

Adenovirus Amplification and Purification.

Samples of adenoviruses expressing either Green Fluorescent Protein (ad.GFP) or GRP78/BiP (ad.BIP) (33) were a kind gift from Professor Guy Rutter, Imperial College, London. The adenoviruses were amplified first on a small scale by infecting 60-70% confluent HEK293 cells in 25 cm tissue culture flasks with 1 µl of obtained adenoviral sample.

The cells were grown for several days until signs of infection were visible. At this stage the cells were harvested together with the medium and half of this crude virus (about 3 ml) was used to infect 75 cm flasks with 60-70% confluent HEK293 cells for large scale amplification. The procedure was repeated for several rounds. Adenovirus was harvested by scraping and spinning down the cells at 1000×g, 10 min, at 4° C. and 1/100 volume of N-butanol was added. The samples were incubated on ice for 1 hour before being spun down at 1000 g, for 10 min at 4° C. The supernatant was harvested and loaded onto a CsCl gradient. The virus was purified by CsCl banding. The titre of the virus was established using Adeno-X rapid titer kit (Clontech), as $1.7 \times 10^{10}$ ifu/ml for both ad.GFP and ad.BiP.

Adenoviral Transduction:

Cells were seeded at $4 \times 10^5$ cells/well in a 6 well plate. After 24 hours the cells were infected with either ad.BiP or ad.GFP at multiplicity of infection (MOI)=8.5 Approximately 16 hours after the infection, the cells were washed once with PBS (phosphate buffered saline) and fresh medium was added. The cells were harvested 48 hours after the infection either in TRIzol for RNA measurements or in RIPA buffer for protein measurements.

Western Blotting:

The samples were harvested in either RIPA buffer (50 mM Tris pH8, 150 mM NaCl, 0.1% SDS, 1 mM EDTA, 0.5% deoxycholate, 1% Igepal and protease inhibitors cocktail, Roche), or Laemmli buffer (62.5 mM Tris pH 6.3, 2% SDS, 25% Glycerol, 5%β-mercapto ethanol, and protease inhibitors). Cells were harvested by scraping, sonicated 2×10 seconds, centrifuged at 14 000 rpm for 30 minutes at 4° C. and the supernatant was collected. For detection of ATF6, cells were harvested in ice cold THE buffer (50 mM Tris HCl, pH7.5; 150 mM NaCl; 1 mM EDTA; 1% Igepal and protease inhibitors cocktail) and lysed for 15 minutes on ice. The lysates were cleared by centrifugation at 12 000 g for 20 minutes at 4° C. For detection of ATF6 the antigen retrieval protocol was followed (15). The following primary antibodies were used: anti-WFS1 rabbit polyclonal (Proteintech Group, INC) 1:500; anti-BIP rabbit polyclonal (Abcam) 1:1000; anti-HRD1 rabbit polyclonal (Abcam or Abgent) 1:100; anti-CHOP mouse monoclonal (Abcam and Santa Cruz) 1:100; anti-cleaved caspase-3 rabbit monoclonal (Cell Signalling) 1:500 and anti-beta actin (Sigma) 1:20000. The secondary antibodies used were: anti-rabbit and anti-mouse (Dako) at a concentration of 1:20000. The primary and secondary antibodies were prepared in 5% milk in PBS/Tween. Incubation with primary antibody was performed over night at 4 degrees C. while with secondary antibody for 1 hour at room temperature. Afterwards the membrane was developed using ECL or ECL plus kit (GE Healthcare). Quantitative analysis was performed by measuring integrated optical density using the program GeneTools.

cDNA Cloning and Generation of Expression Constructs

Cloning of full length hWFS1 cDNA (amino acids 1-890), truncated WFS1 N-terminus (amino acids 1-321) and truncated WFS1 C-terminus (amino acids 652-890) in pCMV-Myc (Clontech) have been described in our previous study (16). The complete coding sequence of hATP6VIA Gene Bank accession number: NM_001690.3) was isolated from a neuroblastoma cDNA library by PCR using the following oligonucleotides: 5'-GCCGCGAATTCCATGGATTTTTC-CAAGC-3' (SEQ ID NO: 1) and 5'-CGAGGTACCC-TAATCTTCAAGGCTAC-3' (SEQ ID NO: 2) and was subsequently cloned into the EcoR1/KpnI sites of the pFLAG-CMV-4 vector (Sigma). The sequence was then confirmed by DNA sequencing.

Real Time PCR and RNA Isolation.

RNA was isolated using TRIzol reagent (Invitrogen) according to manufacturer's instructions. RNA was DNase treated for 30 minutes at 37° C. (DNA-Free, Ambion) and converted to cDNA with High-Capacity cDNA Reverse Transcription Kit (Applied Biosystems). The following Taqman expression assays were used (Applied Biosystems): WFS1: Hs00903605_m1; BiP (endogenous, human): Hs99999174_m1; CHOP: Hs99999172_m1; spliced XBP: Hs03929085_g1; GRP94=Hs00427665_g1 and human beta actin: 4352935E). The expression of hamster BiP (expressed from adenovirus) was measured using Power SYBR Green mix (Applied Biosystems) with the following primers: hamster BiP 5'GGCCGCGTGGAGATCATA (SEQ ID NO: 3) and 5'CACATACGACGGCGTGAT (SEQ ID NO: 4) and human beta actin 5'GGACTTCGAGCAAGAGATGG (SEQ ID NO: 5), 5'AGCACTGTGTTGGCGTACAG (SEQ ID NO: 6) (Thermo Scientific). The expression of endogenous (human) BiP was measured using a set of primers specific to human BiP (Taqman expression assay). The plates were read using BIO-RAD IQ5 machine.

High Content Cytometry for Cell Cycle and Apoptosis Assays:

About 5000 cells were seeded per well of a 96 well plate and incubated overnight. The next day, they were fixed with ice cold 85% ethanol and stained with propidium iodide staining solution. The composition of the propidium iodide staining solution was 0.1% Triton-X-100, 10 mg/ml propidium iodide, 100 mg/ml RNase A in PBS. The cells were incubated with the staining solution for 25 minutes at 37° C., and then DNA content based on total fluorescence was measured with a High Content Cytometer (Acumen). This allows rapid analysis of whole 96 well plates with resolution equivalent to a 20× microscope objective.

For P21$^{cip}$ staining, the cultured plate was first fixed with 1× glyofix 100 µl/well for at least 2 hours, followed by fixing with 100 µl/well ice cold 85% ethanol for 30 minutes. The alcohol was aspirated and replaced with 100 µl/well blocking solution (5% BSA in PBST [1:1000 Triton X]) and incubated for 30 minutes at room temperature. After aspirating the blocking solution, 50 µl/well primary antibody solution (monoclonal P21 Abcam, 1:1000 in PBST) was added and incubated over night at 4° C. and PBST was applied as negative control. The next day, the cells were washed by twice aspirating 200 µl/well PBST. Afterwards, 50 µl/well secondary antibody solution (Anti-mouse IgG-FITC, Abcam, 1:200 in PBST) was added, protecting the solutions and plates from light, and incubated overnight at +4° C. The next day, the cells were washed twice with 200 µl/well PBST and stained with propidium iodide solution as described above.

For ad.BiP infection experiments adenoviral treated cells were plated and grown for 24 hours. After fixing, the plate was treated with anti-BiP polyclonal rabbit antibody 1:800 (Abcam) and the secondary antibody anti-rabbit IgG-FITC, (Abcam, 1:200 in PBST) was used in the same way as p21$^{cip}$ staining.

Statistical analysis: The data is presented as mean±SEM. Statistical significance was analyzed by Student's two sample t test. A p-value of p<0.05 was considered statistically significant.

Results

WFS1 Depleted Human Neuronal Cells Demonstrate ER Stress and Apoptosis.

We stably and transiently depleted WFS1 in human neuroblastoma SK-N-AS and transiently depleted human neuronal NT2 cells by shRNA and siRNA. Three WFS1 stably depleted neuroblastoma clones (KD1-3) showed WFS1 expression significantly reduced by 60-80% in comparison to the control (CL) on both protein and RNA levels. WFS1 transiently depleted cells showed 70-80% reduced expression in comparison to control (FIG. 1A, B and Table 1; transiently depleted neuroblastoma and NT2 cell results, FIG. 3 and Table 3).

We measured the expression of ER stress markers in WFS1 depleted neuroblastoma cells by real time PCR and immunoblotting (FIG. 1, Table 1). The levels of the three ER stress markers CHOP, BiP and spliced XBP1 were increased in both WFS1 stably and transiently depleted neuroblastoma and NT2 cells in comparison to the control on RNA level (FIG. 1A. Table 1; FIGS. 3A and C, Table 3) and protein level (FIG. 1B, D. Table 1). The ER stress and apoptosis markers: ATF6a, HRD1, and cleaved caspase-3 were measured on protein level, and their expressions were increased by 47 to 424% (FIG. 1C, D., Table 1)

We also measured the levels of apoptosis in WFS1 depleted neuroblastoma cells by High Content Cytometry. The technique is based on detecting ongoing or early apoptosis by measuring total fluorescence from DNA fragmentation (18). The results are expressed as percentage apoptotic cells in the whole population. We demonstrated increased apoptosis in WFS1 depleted neuroblastoma cells compared to controls (n=5, $p<0.01$, FIG. 1E).

Correction of ER Stress by Adenoviral Over-Expression of BiP/GRP78

Adenoviral over-expression of the master ER stress chaperone BiP/GRP78 has been used in many studies to reduce ER stress: for example BiP over-expression attenuated increased CHOP expression and rescued cardiomyocytes from cell death (22). Similarly, over-expression of BiP/GRP78 resulted in normalisation of the raised levels of PERK phosphorylation in WFS1 deficient MIN6 cells (9). We therefore attempted to rescue ER stress in WFS1 stably depleted neuroblastoma cells by infecting them with adenovirus over-expressing hamster BiP (ad.BiP) or a negative control expressing GFP (ad.GFP). The adenovirus construct was a kind gift from Professor Guy Rutter (Imperial College London) and was amplified and purified using CsCl banding. BiP expression measured by real time PCR was approximately 2 fold higher in ad.BiP infected cells in comparison to ad.GFP infected cells (FIG. 2A) with the fold-changes: 169±20%, 241±8%, 197±20%, 204±30% in: CL, KD1-3 respectively, (n=3, $p<0.05$). Significant increases in BiP protein levels were demonstrated in ad.BiP infected cells: 1569±459, 1292±296, 1430±664 and 960±107 in CL, KD1-3 respectively (n>3, $p<0.05$, FIG. 2B).

Next we measured the levels of ER stress markers in ad.BiP infected cells relative to ad.GFP infected cells (the expression of each of the markers in the ad.GFP infected clones was assigned as 100%). As shown in FIG. 2C, CHOP mRNA was decreased to 87±4%, 71±17%, 89±7% and 83±5% in CL and KD1-3 respectively in ad.BiP infected cells in comparison to ad.GFP infected cells (n=3, $p<0.05$). The expression of spliced XBP1 was decreased to 68±8%, 64±19%, 47±5%, and 70±8% in CL, KD1 and KD3 respectively in ad.BiP infected samples in comparison to the ad.GFP infected cells (n=3, $p<0.05$). GRP94 mRNA levels in ad.BiP treated cells were decreased to 65±17%, 48±15%, 73±2% and 70±15% in CL and KD1-3 respectively (n=3, $p<0.05$). The largest decrease was measured for endogenous BiP with decrease to 19±18%, 10±8%, 35±16% and 26±11% in ad.BiP versus ad.GFP infected CL and KD1-3 respectively (n=3, $p<0.05$).

The expression of GRP94 was also measured by immunoblotting. GRP94 expression was decreased in ad.BiP infected cells to 56±10%, 70±13%, 64±10%, 80±3% in CL and KD1-3 respectively relative to ad.GFP infected (n=3, $p<0.05$; the protein levels in ad.GFP infected cells were assigned as 100%). To evaluate the effect of ad.BiP overexpression on apoptosis, we measured apoptotic cells by High Content Cytometry; the data presented in FIG. 2E and Table 2 shows that, within each cell line, the number of apoptotic cells was significantly reduced in ad.BiP infected cells in comparison to ad.-GFP infection. The apoptosis noted in the control GFP infected cells is likely to be the apoptosis induced by the experimental procedure rather than the 'baseline' rate of apoptosis in these cells. In summary we abolished the enhanced ER stress response and demonstrated a reduction in the levels of ER stress markers and apoptotic cells by adenoviral over-expression of BiP/GRP78.

WFS1 is Involved in Cell Cycle Regulation

Cell cycle kinetics and cell proliferation were investigated using High Content Cytometry in the WFS1 depleted neuroblastoma cells. Measured parameters indicated the percentage of cells in each phase of the cell cycle, population doubling time (PDT) and the length of each phase of the cell cycle. The Cytometry was performed at 24 hour and 48 hour time points, following an initial 24 hour incubation (which allowed the cells to attach) and presented in FIG. 4 and Table 2. KD1 is a tetraploid cell line: the DNA content of the cells is double that seen in the control and the other two cell lines (showing right shift in Cytometry histogram). Cell cycle kinetics data showed that in KD1 there were more cells in G1 and fewer in G2; in KD2 there were fewer cells in G1 and more in G2 in comparison to control cells at 24 and 48 h cell growth (FIG. 4B and Table 2). The percentages of cells in KD3 after 24 hours of cell growth were significantly different from control (fewer cells in G1 and more cells in G2 phase). However at 48 h cell growth this difference was not statistically significant. At 24 h the differences between the control and KD1 in G1 and G2 phase were statistically significant ($p<0.001$), KD2 vs CL; p=NS and KD3 vs CL, ($p<0.001$). At 48 hours of cell growth the differences between control versus KD1 and KD2 were significant ($p<0.001$) but the differences between CL and KD3 were not statistically significant (p=NS).

The cell proliferation data presented in FIG. 4C and Table 2 show the population doubling time (PDT) was lower in KD2 in comparison to the other cell lines. The time spent in G1 phase was longer in KD1 (39 h) and shorter in KD2 (14 h) in comparison to the control (25 h). The differences between control versus KD1 and KD2 were significant ($p<0.001$) but the differences between CL and KD3 were not statistically significant (p=NS). The time spent in G2 was shorter in KD1 (16 h) and longer in KD2 (31 h) in comparison to the control (Table 2). Overall these results show that the KD1 line has a longer G1 phase while the KD2 line has an elongated G2 phase and a shorter population doubling time in comparison to the control but no significant differences were observed between CL and KD3.

Further we evaluated whether adenoviral over expression of GRP78 affected the cell cycle kinetics. The data presented in Table 2 shows that the number of G1 cells are significantly decreased in ad.-BiP infected cells in comparison to ad.-GFP infection. An opposite image was observed in G2 cells to compensate. These data suggest that ad.Bip transfection normalises the cell cycle kinetics by removing the cell cycle arrest from G1 phase caused by ER stress.

We also evaluated whether the cell cycle effects of WFS1 were due to alterations in $p21^{cip}$ levels. We found that significant $p21^{cip}$ downregulation was present in all three WFS1 depleted cell lines (FIG. 4E). The expression of $p2^{cip}$ was associated with the inhibition of progression through the G2 phase of the cell cycle and inhibition of apoptosis in all four cell lines. In the KD3 line (where $p2^{cip}$ expression was significantly lower) the cell cycle effect of the protein (namely inhibition of progression beyond G2) was also significantly less robust than in the other three cell lines (FIG. 4F); (the ratio of % cells in G2 phase that express $p21^{cip}$ vs cells that don't express $p21^{cip}$: (KD3 (2), control (3), KD1 (6), KD2 (13); $p<0.05$ KD1 vs control); while the anti-apoptotic effect of $p21^{cip}$ was similar to that of the control line (FIG. 4G); (the ratio of % cells in apoptosis expressing $p21^{cip}$ vs cells not expressing $p21^{cip}$: (KD3 (0.125), control (0.1), KD1 (0.1), KD2 (0.05)). In the KD1 cell line the cell cycle modulator effect of $p21^{cip}$ was significantly stronger than in CL (KD1 (6), control (3); $p<0.05$); while in the KD2 line both the cell cycle and anti-apoptotic effects of $p21^{cip}$ were significantly stronger than either the control or KD1 cell lines (FIGS. 4F and 4G).

Discussion

The WFS1 protein is thought to be a negative regulator of the ER stress response. The present study provides additional insights into its role in human neuronal cells. We observed the following: (i) WFS1 protein depletion in human neuronal cells results in raised ER stress response proteins, increased apoptosis and alterations in cell cycle kinetics; (ii) all WFS1 protein depleted cells lines showed variable cell cycle abnormalities; these were ameliorated by adenoviral overexpression of GRP78 (BiP), suggesting that cell cycle dysregulation in WFS1 depleted cells are mediated via ER stress. These findings provide new insights into the mechanisms of neurodegeneration in Wolfram syndrome.

We observed enhanced ER stress in both transiently and stably depleted cells, associated with activation of the apoptotic pathway and impaired cell cycle progression, analogous to the ER stress related diabetes previously described (7-10).

Yamada et al reported cell cycle arrest and impaired cell cycle progression in WFS1 deficient islets (9). Our data on cell cycle kinetics showed that all 3 KD cell lines showed variable disturbances in cell cycle regulation. It is known that the cell cycle/apoptosis regulatory pathways are intricately interconnected consisting of different, sometimes opposite, signals (30,31). It is therefore expected that variable WFS1 depletion, followed by different levels of acute ER stress and compensatory mechanisms (e.g. BiP) as well as varying effects of chronic ER stress (CHOP) will elicit very different patterns of expression for the (p53 dependent and p53 independent) cell cycle regulatory machinery. Overexpression of BiP (in the adenoviral infected cells) affects cell cycle regulation in all cell lines (including control) and reduces the difference in cell cycle kinetics seen in the KD cells relative to the control cells. Thus ameliorating ER stress alone has a significant effect on cell cycle regulation.

The KD1 cell line became tetraploid after WFS1 depletion with a marked accumulation of cells in the G1 phase of the cell cycle and elongation of the G1 phase at the expense of the G2 phase. These changes may be an effect of WFS1 depletion and also suggest that the tetraploidy activates a G1 phase arrest associated with the high level of ER stress and apoptosis in these cells. The QPCR results showed that the expression of CHOP was increased by 150% in this depleted cell line, and only 50% in KD2 and KD3; this could influence the cell cycle behaviour in comparison to KD2 and KD3. Adaptation via endopolyploidy can provide protection from stress and thus increase cell survival (32). The development of tetraploidy in KD1 therefore may be a result of the ER stress. In contrast to the KD1 cell line, the KD2 cell line showed an accumulation of cells in G2 and an elongated G2 time (30 hours, Table 2). The population doubling time of the cells in this knockdown was significantly lower than the control. The KD2 line had normal diploid cells. Furthermore, the cell cycle and anti-apoptotic effects of $p21^{cip}$ were significantly stronger in KD2 than either in the control or in KD1 cell lines. Overall, we found significant $p21^{cip}$ downregulation in WFS1 depleted cells in comparison to the controls; these findings are in contrast to the findings by Yamada (9) who reported p53-independent increase of $P21^{cip1}$ in WFS1 depleted cells associated with the inhibition of the G2 phase of the cell cycle. However, our findings are supported by studies (31) showing that chronic or severe UPR results in down regulation of $p21^{cip}$ and increased levels of CHOP.

Example 2

Further Examples of Drugs that Increase p21 Expression or Activity and Consequently Reduce Cell Death in Neuronal Cells We tested a number of known compounds showing an increase in the expression and/or functional activity of p21 for their effects on cell death in neuronal cells. We found that Flurbiprofen, Dexrasoxane and Rapamycin all increased expression and/or the functional activity of p21 and reduce apoptosis in neuroblastoma cells.

Materials and Methods

Cell Culture:

Human SHSY-5Y neuroblastoma cells were grown in DMEM:F12 supplemented with 10% FCS, penicillin (100 units/mil), streptomycin (100 µg/ml) and L-glutamine. The cells were plated for 24 hours into 96 well plates (5000 cells per well) before treatment with drugs. Each drug (doses applied in separate figures) and the control (DMSO) were applied to 8 technical replicate wells. After 24 hours treatment the cells were harvested by fixation in Glyofix and were post-fixed with ice cold 85% ethanol.

High Content Cytometry for Cell Cycle and Apoptosis Assays:

For $P21^{cip}$ staining, the alcohol was aspirated and replaced with 100 µl/well blocking solution (5% BSA in PBST [1:1000 Triton X]) and incubated for 30 minutes at room temperature. After aspirating the blocking solution, 50 µl/well primary antibody solution (monoclonal P21 Abcam, 1:1000 in PBST) was added and incubated over night at 4° C. and PBST was applied as negative control. The next day, the cells were washed by twice aspirating 200 µl/well PBST. Afterwards, 50 µl/well secondary antibody solution (Anti-mouse IgG-FITC, Abcam, 1:200 in PBST) was added, protecting the solutions and plates from light, and incubated overnight at +4° C. The next day, the cells were washed twice with 200 µl/well PBST and stained with propidium iodide solution. and stained with propidium iodide staining solution. The composition of the propidium iodide staining solution was 0.1% Triton-X-100, 10 mg/ml propidium iodide, 100 mg/ml RNase A in PBS. The cells were incubated with the staining solution for 25 minutes at 37° C., and then DNA content based on total fluorescence was measured with a High Content Cytometer (Acumen). This allows rapid analysis of whole 96 well plates with resolution equivalent to a 20× microscope objective. The measurement of p21 content of cells and nuclei was based on the direct measurement of fluorescent intensity.

Results

FIG. 5. The effect of Flurbiprofen on p21 expression and nuclear translocation.

FIG. 5A: P21 expression induced by Flurbiprofen as measured by fluorescent immunocytochemistry, followed by cytometry. The data indicate that even small doses (0.01 and 0.1 microM) of Flurbiprofen applied for 24 hours can significantly increase p21 expression in neuroblastoma cells.

FIG. 5B: The increase in p21 expression (illustrated above) is parallel to the increase of p21 in the nuclear compartment (active site). The data indicate that even small doses (0.01 and 0.1 microM) of Flurbiprofen applied for 24 hours can significantly increase p21 expression in the nuclear compartment in neuroblastoma cells.

FIG. 5C: The increased expression and nuclear translocation of p21 induced by Flurbiprofen is associated with a significant decrease in apoptotic cell death. The data below indicate that even small doses (0.01 and 0.1 microM) of Flurbiprofen applied for 24 hours can significantly reduce apoptotic cell death in neuroblastoma cells.

FIG. 6. The effect of Dexrazoxane on p21 expression and apoptosis.

FIG. 6A: P21 expression induced by Dexrasoxane as measured by fluorescent immunocytochemistry, followed by cytometry. The data indicate that even small doses (up to 200 microM) of Dexrasoxane applied for 24 hours can significantly increase p21 expression in neuroblastoma cells.

FIG. 6B: P21 expression induced by Dexrasoxane is associated with significantly reduced cell death in neuroblastoma cells.

FIG. 6C: Inverse relationship between P21 expression induced by Dexrasoxane and cell death in neuroblastoma cells. The figure shows that the expression of p21 is strongly associated with a decrease in cell death.

FIG. 7. The effect of Rapamycin on p21 expression and apoptosis

FIG. 7A: P21 expression induced by rapamycin as measured by fluorescent immunocytochemistry, followed by cytometry. The data indicate that small doses (up to 33 microM) of rapamycin applied for 24 hours do not affect p21 expression in neuroblastoma cells.

FIG. 7B: P21 expression induced by rapamycin as measured by fluorescent immunocytochemistry, followed by cytometry. The data indicate that although small doses (up to 33 microM) of rapamycin applied for 24 hours do not affect p21 expression in neuroblastoma cells the drug induces the increased translocation of p21 in the nucleus in neuroblastoma cells.

FIG. 7C: The increased nuclear translocation of p21 induced by Rapamycin (as above) is sufficient to induce the reduction of apoptotic cell death even in the absence of increase in P21 expression.

Discussion

The in vitro data above indicate that:

1. Even small doses of Flurbiprofen (0.01 to 0.1 microM) applied for a short period of time can significantly increase p21 expression in the nuclear compartment and reduce apoptotic cell death in neuronal cells.

2. Small doses of Dexrazoxane (up to 200 microM) applied for only 24 hours are sufficient to significantly increase p21 expression and reduce neuronal cells death.

3. Even small doses of Rapamycin (up to 33 microM) only applied for 24 hours, although do not affect p21 expression in neuroblastoma cells, are sufficient to increase the translocation of p21 in the nucleus and thus increase its function in preventing neuronal death.

REFERENCES

1. Prusiner, S. B. (2001) Neurodegenerative Diseases and Prions. *New England Journal of Medicine*, 344, 1516-1526.
2. Barrett, T. G., Bundey, S. E. and Macleod, A. F. (1995) Neurodegeneration and Diabetes—UK Nationwide Study of Wolfram (Didmoad) Syndrome. *Lancet*, 346, 1458-1463.
3. Genis, D., Davalos, A., Molins, A. and Ferrer, I. (1997) Wolfram syndrome: A neuropathological study. *Acta Neuropathologica*, 93, 426-429.
4. Inoue, Y. Tanizawa, J. Wasson and P. Behn. (1998) A gene encoding a transmembrane protein is mutated in patients with diabetes mellitus and optic atrophy (Wolfram syndrome). *Nature America INC*, 20, 143-147.
5. Strom, T. M., Hortnagel, K., Hofmann, S., Gekeler, F., Scharfe, C., Rabl, W., Gerbitz, K. D. and Meitinger, T. (1998) Diabetes insipidus, diabetes mellitus, optic atrophy and deafness (DIDMOAD) caused by mutations in a novel gene (wolframin) coding for a predicted transmembrane protein. *Human Molecular Genetics*, 7, 2021-2028.
6. Takeda, K., Inoue, H., Tanizawa, Y., Matsuzaki, Y., Oba, J., Watanabe, Y., Shinoda, K. and Oka, Y. (2001) WFS1 (Wolfram syndrome 1) gene product: predominant subcellular localization to endoplasmic reticulum in cultured cells and neuronal expression in rat brain. *Human Molecular Genetics*, 10, 477-484. Fonseca, S. G., Fukuma, M., Lipson, K. L., Nguyen, L. X., Allen, J. R., Oka, Y. and Urano, F. (2005) WFS1 is a novel component of the unfolded protein response and maintains homeostasis of the endoplasmic reticulum in pancreatic beta-cells. *Journal of Biological Chemistry*, 280, 39609-39615.
8. Riggs, A. C., Bernal-Mizrachi, E., Ohsugi, M., Wasson, J., Fatrai, S., Welling, C., Murray, J., Schmidt, R. E., Herrera, P. L. and Permutt, M. A. (2005) Mice conditionally lacking the Wolfram gene in pancreatic islet beta cells exhibit diabetes as a result of enhanced endoplasmic reticulum stress and apoptosis. *Diabetologia*, 48, 2313-2321.
9. Yamada, T., Ishihara, H., Tamura, A., Takahashi, R., Yamaguchi, S., Takei, D., Tokita, A., Satake, C., Tashiro, F., Katagiri, H. et al. (2006) WFS1-deficiency increases endoplasmic reticulum stress, impairs cell cycle progression and triggers the apoptotic pathway specifically in pancreatic beta-cells. *Human Molecular Genetics*, 15, 1600-1609.
10. Philbrook, C., Fritz, E. and Weiher, H. (2005) Expressional and functional studies of Wolframin, the gene function deficient in Wolfram syndrome, in mice and patient cells. *Experimental Gerontology*, 40, 671-678.
11. Luuk, H., Koks, S., Plaas, M., Hannibal, J., Rehfeld, J. F. and Vasar, E. (2008) Distribution of Wfs1 protein in the central nervous system of the mouse and its relation to clinical symptoms of the Wolfram syndrome. *Journal of Comparative Neurology*, 509, 642-660.
12. Swift, R. G., Sadler, D. B. and Swift, M. (1990) Psychiatric Findings in Wolfram Syndrome Homozygotes. *Lancet*, 336, 667-669.
13. Kõks, S., Planken, A., Luuk, H. and Vasar, E. (2002) Cat odour exposure increases the expression of wolframin gene in the amygdaloid area of rat. *Neuroscience Letters*, 322, 116-120.

14. Luuk, H., Plaas, M., Raud, S., Innos, J., Sutt, S., Lasner, H., Abramov, U., Kurrikoff, K., Koks, S. and Vasar, E. (2009) Wfs1-deficient mice display impaired behavioural adaptation in stressful environment. *Behavioural Brain Research*, 198, 334-345.
15. Fonseca, S. G., Ishigaki, S., Oslowski, C. M., Lu, S., Lipson, K. L., Ghosh, R., Hayashi, E., Ishihara, H., Oka, Y., Permutt, M. A. et al. (2010) Wolfram syndrome 1 gene negatively regulates ER stress signaling in rodent and human cells. *The Journal of Clinical Investigation*, 120, 744-755.
16. Zatyka, M., Ricketts, C., Xavier, G. D., Minton, J., Fenton, S., Hofmann-Thiel, S., Rutter, G. A. and Barrett, T. G. (2008) Sodium-potassium ATPase beta 1 subunit is a molecular partner of Wolframin, an endoplasmic reticulum protein involved in ER stress. *Human Molecular Genetics*, 17, 190-200.
17. Hatanaka, M., Tanabe, K., Yanai, A., Ohta, Y., Kondo, M., Akiyama, M., Shinoda, K., Oka, Y. and Tanizawa, Y. (2011) Wolfram syndrome 1 gene (WFS1) product localizes to secretory granules and determines granule acidification in pancreatic β-cells. *Human Molecular Genetics*, 20, 1274-1284.
18. Payne, W. P. B. a. S. L. (2005). High-content screening in oncology using fluorescence microplate cytometry. *Nature Methods*, 2, i-ii.
19. Short, B. (2010) The acid test of v-ATPase function. *The Journal of Cell Biology*, 189, 773.
20. Futai, M., Oka, T., Sun-Wada, G., Moriyama, Y., Kanazawa, H. and Wada, Y. (2000) Luminal acidification of diverse organelles by V-ATPase in animal cells. *Journal of Experimental Biology*, 203, 107-116.
21. Ishihara, H., Takeda, S., Tamura, A., Takahashi, R., Yamaguchi, S., Takei, D., Yamada, T., Inoue, H., Soga, H., Katagiri, H. et al. (2004) Disruption of the WFS1 gene in mice causes progressive beta-cell loss and impaired stimulus-secretion coupling in insulin secretion. *Human Molecular Genetics*, 13, 1159-1170.
22. Fu, H. Y., Minamino, T., Tsukamoto, O., Sawada, T., Asai, M., Kato, H., Asano, Y., Fujita, M., Takashima, S., Hori, M. et al. (2008), *Cardiovasc Res*, 79, 600-610.
23. Tabares, L. and Betz, B. (2010) Multiple Functions of the Vesicular Proton Pump in Nerve Terminals. *Neuron*, 68, 1020-1022.
24. Beyenbach, K. W. and Wieczorek, H. (2006) The V-type H+ ATPase: molecular structure and function, physiological roles and regulation. *Journal of Experimental Biology*, 209, 577-589.
25. Wieczorek, H., Beyenbach, K. W., Huss, M. and Vitayska, O. (2009) Vacuolar-type proton pumps in insect epithelia. *Journal of Experimental Biology*, 212, 1611-1619.
26. Thévenod, F., Friedmann, J. M., Katsen, A. D. and Hauser, I. A. (2000) Upregulation of Multidrug Resistance P-glycoprotein via Nuclear Factor-κB Activation Protects Kidney Proximal Tubule Cells from Cadmium- and Reactive Oxygen Species-induced Apoptosis. *Journal of Biological Chemistry*, 275, 1887-1896.
27. Hinton, A., Sennoune, S. R., Bond, S., Fang, M., Reuveni, M., Sahagian, G. G., Jay, D., Martinez-Zaguilan, R. and Forgac, M. (2009) Function of a Subunit Isoforms of the V-ATPase in pH Homeostasis and in Vitro Invasion of MDA-MB231 Human Breast Cancer Cells. *Journal of Biological Chemistry*, 284, 16400-16408.
28. Sun-Wada, G. H., Toyomura, T., Murata, Y., Yamamoto, A., Futai, M. and Wada, Y. (2006) The a3 isoform of V-ATPase regulates insulin secretion from pancreatic β-cells. *Journal of Cell Science*, 119, 4531-4540.
29. Forgac, M. (2007) Vacuolar ATPases: rotary proton pumps in physiology and pathophysiology. *Nat Rev Mol Cell Biol*, 8, 917-929.
30. Tabas, I. and Ron, D. (2011) Integrating the mechanisms of apoptosis induced by endoplasmic reticulum stress. *Nature Cell Biology*, 13, 184-190.
31. Mihailidou, C., Papazian, I., Papavassiliou, A. G. and Kiaris, H. (2010) CHOP-dependent Regulation of p21/waf1 During ER Stress. *Cellular Physiology and Biochemistry*, 25, 761-766.
32. Lee, H. O., Davidson, J. M. and Duronio, R. J. (2009) Endoreplication: polyploidy with purpose. *Genes & Development*, 23, 2461-2477.
33. Fu, Y., Li, J. and Lee, A. S. (2007), *Cancer Research*, 67, 3734-3740.

Tables

TABLE 1

Characterisation of stable SK-N-AS clones with WFS1 depletion

| Genes | KD1 (%) | KD2 (%) | KD3 (%) | method | n | p-value |
|---|---|---|---|---|---|---|
| WFS1-depletion | 71 ± 2 | 61 ± 3 | 60 ± 4 | QPCR | 6 | P < 0.001 |
|  | 76 ± 7 | 78 ± 4 | 63 ± 7 | WB | 6 | P < 0.05 |
| BiP- induction | 70 ± 17 | 83 ± 28 | 59 ± 13 | QPCR | 5 | P < 0.05 |
|  | 407 ± 71 | 255 ± 94 | 129 ± 49 | WB | 6 | P < 0.05 |
| CHOP-induction | 146 ± 7 | 56 ± 9% | 54 ± 14% | QPCR | 3 | P < 0.05 |
|  | 95 ± 15 | 96 ± 62 | 67 ± 17 | WB | 3 | P < 0.05 |
| Sp-XBP1-induction | 107 ± 28%, | 110 ± 27 | 94 ± 33 | QPCR | 7 | P < 0.01 |
| ATF6a-induction | 377 ± 119 | 280 ± 149 | NM | WB | 4 | P < 0.05 |
| HRD1- induction | 375 ± 121 | 424 ± 120 | NM | WB | 4 | P < 0.05 |
| Caspase-3-induction | 73 ± 18 | 100 ± 41 | 47 ± 6 | WB | 5 | P < 0.05 |

QPCR = real-time PCR, WB = Western blotting, NM = Not measured, NS = not significant, n = number of experiments, (%) = fold change in comparison to the control.

TABLE 2

Cell cycle and apoptosis data of WFS1 depleted neuroblastoma cells

| Measured parameters | CL | KD1 | KD2 | KD3 |
|---|---|---|---|---|
| G1 cells (%) at 24 h | 56 ± 0.3 | 77 ± 1.3 | 55 ± 0.4 | 44 ± 0.4 |
| G2 cells (%) at 24 h | 29 ± 0.3 | 12 ± 0.4 | 30 ± 0.5 | 35 ± 0.5 |
| G1 cells (%) at 48 h | 47 ± 0.3 | 68 ± 0.4 | 32 ± 0.5 | 47 ± 0.3 |
| G2 cells (%) at 48 h | 36 ± 0.4 | 18 ± 0.4 | 48 ± 0.8 | 32 ± 0.6 |
| PDT (h) | 65 ± 2 h | 65 ± 3 h | 54 ± 3 h | 65 ± 2 h |
| G1 time (h) | 25 ± 0.8 h | 39 ± 1.5 h | 14 ± 0.7 h | 25 ± 0.8 h |
| G2 time (h) | 29 ± 1 h | 16 ± 1 h | 31 ± 2 h | 26 ± 1 h |
| Ad-BiP-apop-cells (%) | 6 ± 1.7 | 6 ± 1.6 | 3 ± 1 | 3 ± 1 |
| Ad-GFP-apop-cells (%) | 11 ± 1.6 | 19 ± 3.9 | 7 ± 1 | 5 ± 1 |
| Ad-BiP-G1 cells | 16 ± 6.2 | 9 ± 2.6 | 12 ± 4 | 11 ± 3 |
| Ad-GFP-G1-cells | 41 ± 2.6 | 52 ± 3.5 | 25 ± 2 | 22 ± 3 |
| P21-protein per-cell | 303 ± 43 | 226 ± 42 | 243 ± 18 | 89 ± 12 |
| P21-pos-G2 cells (%) | 44 ± 2.6 | 34 ± 3.8 | 67 ± 4.5 | 65 ± 10.7 |
| P21-neg-G2 cells (%) | 13 ± 1.9 | 6 ± 1.2 | 8 ± 2.3 | 29 ± 3.9 |
| P21-pos-apop cells | 1 ± 0.3 | 1 ± 0.4 | 0 ± 0.3 | 1 ± 0.4 |
| P21-neg-apop cells | 19 ± 3 | 20 ± 3 | 23 ± 0.3 | 9 ± 3.1 |

PDT = population doubling time,
apop = apoptosis,
h = hours,
% = cells in cells cycle phase.
Ad-GFP-apop-cells: adenoviral-BiP transfected cells showing apoptosis.
Ad-BiP-G1 cells: adenoviral-BiP transfected cells in G1 phase.
Ad-GFP-apop-cells: adenoviral-GFP transfected cells showing apoptosis.
P21-pos-G2 cells: Cells expressing p21$^{cip}$ in G2 phase.

TABLE 3

Characterisation of transient knockdowns in SK-N-AS and NT2 cell lines

| Genes | KDA (%) | KDB (%) | KDC (%) | KDD (%) | n | p-value | method |
|---|---|---|---|---|---|---|---|
| WFS1-depletion | 79 ± 2 | 61 ± 9 | 83 ± 1 | 83 ± 1 | 6 | P < 0.001 | QPCR |
|  | 76 ± 6 | 72 ± 3 | 63 ± 8 | 61 ± 6 | 5 | P < 0.05 | WB |
| BiP- induction | 133 ± 2 | 25 ± 6 | 23 ± 8 | 49 ± 13 | 3 | P < 0.05 | QPCR |
| CHOP-induction | 70 ± 6 | 38 ± 7 | 52 ± 31 | 52 ± 5 | 3 | P < 0.05 | QPCR |
| XBP1-induction | 89 ± 8 | 53 ± 6 | NM | NM | 3 | p < 0.05 | QPCR |

KDA and KDB: SK-N-AS cell lines, KDC and KDD: NT2 cell lines, QPCR = real-time PCR, WB = Western blotting, NM = Not measured, n = number of experiments, (%) = fold change in comparison to the control.

TABLE 4

List of drugs known to induce p21 production or activation in the literature

1. Expression regulated by:

doxorubicin,
cisplatin,
phorbol myristate acetate,
PD98059,
tretinoin,
mitomycin C,
1-alpha, 25-dihydroxy vitamin D3,
etoposide,
dexamethasone,
beta-estradiol,
butyric acid,
camptothecin,
romidepsin,
sulindac,
actinomycin D,
paclitaxel,
trichostatin A,
decitabine,
LY294002,
troglitazone,
prostaglandin A2,
nutlin-3a,
mir-192,
S-nitroso-N-acetylpenicillamine,
fulvestrant,
mir-17,
nicotine,
silibinin,
U0126,
vorinostat,
apicidin,
benzyloxycarbonyl-Leu-Leu-Leu aldehyde,
eflornithine,
progesterone,
sodium arsenite,
GGTI-298,
beta-phorbol 12,13-dibutyrate,
cycloheximide,
rosiglitazone,
N-Ac-Leu-Leu-norleucinal,
corticosterone,
estrogen, TABLE 4-continued List of drugs known to induce p21 production or activation in the literature lactacystin,
resveratrol,
sirolimus,
1,1-bis(3'-indolyl)-1-(4-trifluoromethyl-phenyl)methane,
deferoxamine,
ethylcholine aziridinium,
tamoxifen,
bortezomib,
entinostat,
hemin,
lovastatin,
rottlerin,
AGN194204,
O-(chloroacetylcarbamoyl)fumagillol,
bisindolylmaleimide I,
cerivastatin,
ciglitazone,
cyclopamine,
dihydrotestosterone,
nutlin-3,
oxaliplatin,
pi3k,
tetrachlorodibenzodioxin,
tetramerization domain,
ORG 31710,
UCN-01,
dacinostat,
diethylstilbestrol,
flavopiridol,
genistein,
methylnitronitrosoguanidine,
perifosine,
prostaglandin A1,
wortmannin,
2[[3-(2,3-dichlorophenoxy)propyl]amino]ethanol,
4-hydroxytamoxifen,
Alpha Conotoxin M2,
L-ornithine,
N(omega)-hydroxyarginine,
N1,N11-diethylnorspermine,
adaphostin,
anti-benzo(a)pyrene-diol-epoxide,
artemisinin,
ascorbic acid,
dihydroartemisinin,
dimethylnitrosamine,
doxifluridine,
epigallocatechin-gallate,
forskolin,
let-7a-5p (and other miRNAs w/seed GAGGUAG),
metribolone,
miR-1227 (miRNAs w/seed GUGCCAC),
miR-1255b-5p (and other miRNAs w/seed GGAUGAG),
miR-1288 (miRNAs w/seed GGACUGC),
miR-1304-5p (miRNAs w/seed UUGAGGC),
miR-132-3p (and other miRNAs w/seed AACAGUC),
miR-146b-3p (and other miRNAs w/seed GCCCUGU),
miR-149-3p (and other miRNAs w/seed GGGAGGG),
miR-17-5p (and other miRNAs w/seed AAAGUGC),
miR-1972 (miRNAs w/seed CAGGCCA),
miR-1982-5p (and other miRNAs w/seed UGGGAGG),
miR-202-3p (and other miRNAs w/seed GAGGUAU),
miR-208b-3p (and other miRNAs w/seed UAAGACG),
miR-22-3p (and other miRNAs w/seed AGCUGCC),
miR-224-5p (and other miRNAs w/seed AAGUCAC),
miR-2277-3p (miRNAs w/seed GACAGCG),
miR-298 (miRNAs w/seed GCAGAAG),
miR-301a-3p (and other miRNAs w/seed AGUGCAA),
miR-3127-3p (miRNAs w/seed CCCCUUC),
miR-3145-5p (miRNAs w/seed ACUCCAA),
miR-3150a-3p (miRNAs w/seed UGGGGAG),
miR-3150b-3p (and other miRNAs w/seed GAGGAGA),
miR-3175 (miRNAs w/seed GGGGAGA),
miR-3180-3p (and other miRNAs w/seed GGGGCGG),
miR-3189-5p (miRNAs w/seed GCCCCAU),
miR-343 (and other miRNAs w/seed CUCCCUC),
miR-345-5p (miRNAs w/seed CUGACUC),
miR-365-3p (and other miRNAs w/seed AAUGCCC),
miR-3657 (miRNAs w/seed GUGUCCC),
miR-3663-3p (and other miRNAs w/seed GAGCACC),
miR-3672 (miRNAs w/seed UGAGACU),
miR-3689d (miRNAs w/seed GGAGGUG),
miR-370 (and other miRNAs w/seed CCUGCUG),
miR-3714 (miRNAs w/seed AAGGCAG),
miR-3914 (miRNAs w/seed AGGAACC),
miR-423-5p (and other miRNAs w/seed GAGGGGC),
miR-4283 (miRNAs w/seed GGGGCUC),
miR-4286 (miRNAs w/seed CCCCACU),
miR-4310 (miRNAs TABLE 4-continued List of drugs known to induce p21 production or activation in the literature w/seed CAGCAUU),
miR-4323 (miRNAs w/seed AGCCCCA),
miR-4329 (miRNAs w/seed CUGAGAC),
miR-4487 (miRNAs w/seed GAGCUGG),
miR-4497 (miRNAs w/seed UCCGGGA),
miR-4527 (miRNAs w/seed GGUCUGC),
miR-4537 (miRNAs w/seed GAGCCGA),
miR-455-3p (and other miRNAs w/seed CAGUCCA),
miR-4648 (miRNAs w/seed GUGGGAC),
miR-4651 (and other miRNAs w/seed GGGGUGG),
miR-4667-3p (miRNAs w/seed CCCUCCU),
miR-4681 (miRNAs w/seed ACGGGAA),
miR-4689 (miRNAs w/seed UGAGGAG),
miR-4697-5p (and other miRNAs w/seed GGGGGCG),
miR-4715-3p (miRNAs w/seed UGCCACC),
miR-4719 (miRNAs w/seed CACAAAU),
miR-4726-5p (and other miRNAs w/seed GGGCCAG),
miR-4731-5p (miRNAs w/seed GCUGGGG),
miR-4732-5p (miRNAs w/seed GUAGAGC),
miR-4747-5p (and other miRNAs w/seed GGGAAGG),
miR-485-5p (and other miRNAs w/seed GAGGCUG),
miR-499a-5p (and other miRNAs w/seed UAAGACU),
miR-515-3p (and other miRNAs w/seed AGUGCCU),
miR-520h (and other miRNAs w/seed CAAAGUG),
miR-558 (miRNAs w/seed GAGCUGC),
miR-572 (miRNAs w/seed UCCGCUC),
miR-602 (miRNAs w/seed ACACGGG),
miR-637 (miRNAs w/seed CUGGGGG),
miR-662 (miRNAs w/seed CCCACGU),
miR-665 (and other miRNAs w/seed CCAGGAG),
miR-708-5p (and other miRNAs w/seed AGGAGCU),
miR-764* (and other miRNAs w/seed AGGAGGC),
miR-765 (and other miRNAs w/seed GGAGGAG),
miR-879-5p (and other miRNAs w/seed GAGGCUU),
miR-939 (miRNAs w/seed GGGGAGC),
mir-25,
mir-34,
simvastatin,
15-deoxy-delta-12,14-PGJ 2,
2-(4-amino-3-methylphenyl)-5-fluorobenzothiazole,
acetaminophen,
aphidicolin,
benzo(a)pyrene,
beta-glycerophosphoric acid,
calphostin C,
celecoxib,
curcumin,
cyclic GMP,
cyclosporin A,
diethylnitrosamine,
epicatechin gallate,
fibroblasts,
hormone binding domain,
imatinib,
keratinocytes,
leptomycin B,
lipopolysaccharide,
lithium,
lithium chloride,
meloxicam,
methylselenic acid,
mevastatin,
mifepristone,
ouabain,
phenoxodiol,
retinoid,
sodium orthovanadate,
sparfosic acid,
tanespimycin,
teniposide,
tipifarnib,
tozasertib,
valproic acid,
zVAD,
zVAD-FMK,
(6)-gingerol,
N-acetyl-L-cysteine,
N-ethyl-N-nitrosourea,
asiatic acid,
aspirin,
berberine,
bleomycin,
bromobenzene,
bucladesine,
budesonide,
busulfan,
butylhydroxybutylnitrosamine,
carbamylcholine,
cerulenin,
chloramphenicol,
daunorubicin,
diclofenac,
docosahexaenoic acid,
etomoxir,
everolimus,
exisulind,
farnesol,
fludarabine,
gemcitabine,
geraniol,
green tea polyphenol, TABLE 4-continued List of drugs known to induce p21 production or activation in the literature indole-3-carbinol,
indomethacin,
isoobtusilactone A,
letrozole,
methoprene acid,
mimosine,
mir-21,
nocodazole,
p-aminobenzoic acid,
panobinostat,
phorbol 12,13-dibutyrate,
pioglitazone,
pirinixic acid,
plicamycin,
porfimer sodium,
quinacrine,
quinoline-Val-Asp(OMe)-CH2-OPH,
racemic flurbiprofen,
roscovitine,
sulforafan,
sunitinib,
tetraethylammonium,
thapsigargin,
thymeleatoxin,
thymoquinone,
tranilast,
trans-4-carboxy-5-octyl-3-methylenebutyrolactone,
trapoxin,
tyrphostin AG 1478,
vinblastine,
vincristine,
zidovudine,
1,10-phenanthroline,
1,25-dihydoxy-16-ene-5-6-trans-vitamin D3,
10-decarbamoylmitomycin C,
13-cis-retinoic acid,
15(R/S)-methyl-lipoxin A4,
16-phenoxy-lipoxin A4,
2,2-dimethylbutyric acid,
2,2-dimethylmethoxyacetic acid,
2,3 butanedione monoxime,
2,4-thiazolidinedione,
2,7-diaminomitosene,
2-(2-mercaptoethanol)-3-methyl-1,4-naphthoquinone,
2-deoxyglucose,
2-hydroxy-9-cis-octadecenoic acid,
2-thio(3-iodobenzyl)-5-(1-pyridyl)-[1,3,4]-oxadiazole,
23,24-dihydrocucurbitacin,
3'-O-L-alanyl-thymidine,
3-deazaadenosine,
4-(9H-fluoren-3-ylamino)-4-oxo-2-butenoic acid,
4-coumaric acid,
4-nitroquinoline-1-oxide,
5-iminodaunorubicin,
7-ethyl-10-hydroxy-camptothecin,
8-chlorophenylthio-adenosine 3',5'-cyclic monophosphate,
A23187,
AVI-4126,
Ahr-aryl hydrocarbon-Arnt,
H-[1,2,4]oxadiazolo[4,3-alpha]quinoxalin-1-one,
N-(4-aminobutyl)-5-chloro-2-naphthalenesulfonamide
PP2/AG1879 tyrosine kinase inhibitor,
Rep68,
Ro 25-6760,
Ro41-5253,
Rta,
S-nitrosoglutathione,
Sb202190,
acyclic retinoid,
amitriptyline,
apigenin,
arbutin,
arotinoid acid,
arsenite,
atosiban,
benidipine,
butyrine,
calyculin A,
chartreusin,
chlamydocin,
cucurbitacin B,
cytarabine,
decursin,
desipramine,
diallyl trisulfide,
dichlororibofuranosylbenzimidazole,
diethyl-bis(pentamethylene-N,N-dimethylcarboxamide)malonate,
diethylmaleate,
discodermolide,
ectodomain,
enalapril,
epinephrine,
epothilone B,
ethyl protocatechuate,
ethylenimine quinone,
fingolimod,
fluvastatin,
ganciclovir,
gitoxigenin,
glutathione,
hexamethylene bisacetamide,
idarubicin,
igmesine,
indirubin-3'-monoxime,
leucovorin,
levamisole,
lipoxin A4,
m-carboxycinnamic acid bishydroxamide,
magnesium,
magnolol,
malondialdehyde,
melatonin,
melphalan,
metformin,
methotrexate,
methylprednisolone,
mezerein,
mir-26,
mitoxantrone,
morphine,
moxonidine,
mycophenolic acid, TABLE 4-continued List of drugs known to induce p21 production or activation in the literature nomilin,
octreotide,
oleanolic acid,
oridonin,
oxamflatin,
pentazocine,
phenobarbital,
phenoxyacetic acid,
prostaglandin E2,
quinidine,
raloxifene,
selumetinib,
spironolactone,
staurosporine,
sulindac sulfide,
suramin,
telomestatin,
testosterone,
tetrandrine,
thyroid hormone,
topotecan,
tosedostat,
trabectedin,
tributyrin,
trovafloxacin,
tyrphostin AG825,
v-abl,
vapreotide,
vinflunine,
vitamin A,
vitamin D,
vitamin E,
zinc protoporphyrin IX,
zinostatin
2. Binding regulated by:

1-alpha,
25-dihydroxy vitamin D3,
ORG 31710,
lovastatin,
prostaglandin A2,
5-fluorouracil,
EB-1089,
fulvestrant,
CP-31398,
actinomycin D,
cisplatin,
decursin,
dexamethasone,
indole-3-carbinol,
romidepsin,
Ampk,
GGTI-298,
benzyloxycarbonyl-Leu-Leu-Leu aldehyde,
beta-estradiol,
butyric acid,
nutlin-3,
perifosine,
plicamycin,
sirolimus,
thymeleatoxin,
tretinoin,
BMS453,
Calcineurin,
O-(chloroacetylcarbamoyl)fumagillol,
beryllium sulfate,
doxorubicin,
eflornithine,
farnesol,
geraniol,
mevalonic acid,
mevastatin,
nitric oxide, TABLE 4-continued List of drugs known to induce p21 production or activation in the literature okadaic acid,
perilla alcohol,
phorbol myristate acetate,
silibinin,
staurosporine,
tamoxifen,
vorinostat
3. Activation regulated by:

perifosine,
phorbol myristate acetate,
cisplatin,
apicidin,
fulvestrant,
mir-192,
5-fluorouracil,
XCT790,
bisindolylmaleimide I,
calphostin C,
epigallocatechin-gallate,
flavopiridol,
methyl methanesulfonate,
mir-17,
phorbol 12,13-dibutyrate,
resveratrol,
romidepsin,
vorinostat
4. Accumulation regulated by dexamethasone,
doxorubicin,
bortezomib,
butyric acid,
lomefloxacin,
1-alpha,
25-dihydroxy vitamin D3,
5-fluorouracil,
N-Ac-Leu-Leu-norleucinal,
N-Ac-leucyl-leucyl-methioninal,
PD98059,
U0126,
UCN-01,
actinomycin D,
alpha-amanitin,
bleomycin,
dichlororibofuranosylbenzimidazole,
hydroxyurea,
mir-192,
oxidative stress,
paclitaxel,
perifosine,
roscovitine
5. Induction regulated by:

doxorubicin,
mitomycin C,
dacinostat,
decitabine,
U0126,
cycloheximide,
ganciclovir,
pifithrin alpha,
raltitrexed, TABLE 4-continued List of drugs known to induce p21 production or activation in the literature sirolimus (rapamycin),
sodium arsenite,
tachypyridine Example 3

Screening of Further Compounds for Identification of WS Therapeutic Agents

Further compounds were tested to determine their effect on the cell cycle, $p21^{cip1}$ expression, and the effects of $p21^{cip1}$ expression in treated cells on the cell cycle and apoptosis.

Materials and Methods

Cell Culture

SK-N-AS human neuroblastoma cell line was purchased from ECACC and grown in DMEM (with 4.5 g/L D-glucose; L-glutamine and pyruvate) supplemented with 10% foetal calf serum (FCS), 100 U penicillin-streptomycin, 2 mM L-glutamine and 1×MEM non-essential amino acids (MEM-NEAA) in a 37° C./5% $CO_2$ humidified atmosphere incubator. Cultures were grown to confluence and passed 1 in 5. Cells were frozen at −80° C. in FCS containing DMSO at a density of 3 million cells/ml.

C7 is SK-N-AS derived cell line stably transfected with a scrambled shRNA. KD2 and KD3 are SK-N-AS derived stably depleted WFS1 cell lines. WFS1 depletion in KD2 is ∞78% and in KD3 is ∞60% (Gharanei et al., Hum Mol Genet 22(2):203-17 (2013)). C7, KD2 and KD3 cell lines are propagated in DMEM (with 4.5 g/L D-glucose; L-glutamine and pyruvate) supplemented with 10% foetal calf serum (FCS), 100 U penicillin-streptomycin, 2 mM L-glutamine, 1×MEM non-essential amino acids (MEM-NEAA) and 2.5 µg/ml puromycin in a 37° C./5% $CO_2$ humidified atmosphere incubator. Cultures were grown to confluence and passaged (C7: 1 in 3; KD2: 1 in 4; KD3: 1 in 5). For storage, cells were frozen at −80° C. in FCS containing 10% DMSO at a density of 3.5-5.5 million/ml (C7: 5.5 million/ml; KD2: 4.5 million/ml; KD3: 3.5 million/ml).

Routine sub-culturing procedures were carried out in a Class 2 Biological Safety Cabinet in WX2.40 Genes, Development and Reproduction Division, Clinical and Experimental Medicine, University of Birmingham using sterile consumables. All cell cultures procedures for drug treatments were carried out in a Category 2 Laminar Flow Cabinet in ES3 and ES4, Neuroscience Division, Clinical and Experimental Medicine, University of Birmingham using sterile consumables.

Setting Up C7, KD2 and KD3 Cultures from Frozen Cells

Wash media and the 2× culture media were warmed in 37° C. water bath for 45 minutes. Laminar flow cabinet was sterilized using barrycidal. Into 50 ml sterile Falcon tube, 45 ml of wash media was dispensed, one for each cell line. Aliquot of frozen cells in cryovial, one from each cell line were removed from −80° C. freezer, sprayed with barrycidal and wiped dry. The cyovials were opened, using 1 ml pipette tip wash media was added, pipette up and down few times and transferred to the wash media in 50 ml Falcon. This was repeated until cryovial was empty. After the 3 cell lines were transferred into wash media in 50 ml Falcon, the tubes were capped and mixed by inversion. The cell suspensions were then centrifuged at 400 rcf at room temperature for 5 minutes. The supernatant were then discarded by pouring off the wash media from the Falcon with one slow move. The cell pellets were then re-suspended in 3 ml of wash media using a fine tip pastette (12 aspirations). The tubes were then recapped and vortexed briefly. The number of cells in the 3 ml of cell suspension were then counted using the Cellometer.

Using the cc calculator programme, the necessary dilutions were calculated for each cell line. Wash media was then added to obtain 80.000 cells/ml suspension.

Plating Cells for Culture

Cells were plated onto 96-well flat bottom, tissue culture treated plates (BD Falcon 353072) at a density of 4000 cells/well. Four sterile reagent reservoirs (Corning 4872, 100 ml) were labelled, one for each cell line and one with 2× culture media ready to add to the plated cells. The C7 cell suspension were poured into sterile reagent reservoir labelled C7 and using multichannel pipette, 50 µl of cell suspension were dispense into each well. Then 50 µl of 2× culture media was added into each well. Plating was repeated for KD2 and KD3 cell lines. One plate of 'zero day control' was also prepared per experiment. On 'zero day control' plate, C7 cell line were plated into columns 1, 2, 7 and 8; KD2 cell line were plated into columns 3, 4, 9 and 10; KD3 cell line were plated into columns 5, 6, 11 and 12. Cells were plated at the same density for both 'zero day control' and experiment plates. The 'zero day control' plate remains untreated and is to be harvested just before the drugs were added into the treatment plates. Cells are then allowed to settle for 24 hours at 37° C. in a humidified incubator containing 95% air/5% $CO_2$.

Drug Treatments

Drugs are prepared as 10 mM stock solutions either in filter-sterilized $H_2O$ or in molecular biology grade DMSO (Sigma D8418/Lot SHBC2107V) and stored in −80° C. freezer.

| Drug name | Supplier/Product code | Lot No. | Solvent |
| --- | --- | --- | --- |
| Sodium valproate | Sigma/P4543 | SLBC9758V | $H_2O$ |
| Chloroquine diphosphate | Sigma/C6628 | BCBJ1498V | $H_2O$ |
| Pioglitazone hydrochloride | Sigma/E6910 | 022M4747V | DMSO |
| Sodium 4-phenylbutyrate | Calbiochem/567616 | D00129710 | $H_2O$ |
| Fusidic acid | VWR/A6560 | 3X000362 | DMSO |
| Ciclopirox olamine | Cambridge Biosci/C3208 | 2592503 | DMSO |
| 4-Aminophenyl sulfone (Dapsone) | Sigma/A74807 | MKBG7137V | DMSO |
| Rifampicin (NOT in Table 4) | VWR/A2220 | 2Q005529 | DMSO |
| Loperamide hydrochloride | Sigma/L4762 | P500162 | DMSO |

For each drug, 2× working solutions are prepared in culture medium and added to the cultures. The highest drug concentration is 100 µM and final solvent ($H_2O$/DMSO) concentration in the cultures is 1%.

Preparation of 100× drug final concentrations: In 96-well sterile plate with 200 µl capacity (Star Lab E1403), 45 µl of solvent ($H_2O$ or DMSO) were dispensed to columns 1-5 and 7-11. Then 50 µl of drug stock solutions (10 mM) were transferred to column 6 (drug 1) and to column 12 (drug 2). Drugs were then diluted 1 in 10 by taking 5 µl drug solutions out of column 6 (using an 8-channel 0.5-10 µl pipetor) to column 5 and mix by pipetting (10× aspirations). Then 5 µl from column 5 were transferred to column 4, mixed as before and this was repeated until reaching column 2. When reaching column 2, 5 µl of drug solution was discarded, leaving column 1 with solvent only. Columns 12-7 were treated as columns 6-1.

Preparation of 20× final drug concentrations: 20 µl of drug solutions from the 100× drug plate were transferred into a new, sterile 96 well plate with 200 µl capacity using an 8-multichannel pipetor. 80 µl of culture media were then added and mixed (10 aspirations).

Preparation of 2× final drug concentrations: 40 µl of 20× drug concentrations were transferred into a sterile deep well plate with 2 ml capacity (Fisher BMX-100-040J) using an 8-multichannel pipetor. To this plate 360 µl of culture media were then added to each well and mixed (10 aspirations) to obtain 2× final drug concentrations.

Using an 8-multichannel pipetor, 100 µl of 2× final drug concentrations were gently dispensed into the culture plates of C7, KD2 and KD3 cells. The time of the treatment was noted and cells were transferred back into 37° C./5% $CO_2$ humidified incubator and were incubated for 24 hours.

After treating the C7, KD2 and KD3 cells, the 'zero day control' plate was removed from the incubator, culture media were removed from the plate and 200 µl of 1× Glyo-fixx (Thermofisher 6764265, prepared from 5× concentrate according to manufacturer's instructions) was added to each well. 'Zero day control' plate was then wrap in cling-film and stored at +4° C.

Collection of Cells

After 24 hours incubation, plates were removed from the incubator. Culture medium containing drug were removed and 200 µl of Glyo-fixx was added to each well. Plates are then incubated at room temperature for 2 hours. The 'zero day control' plate was also removed from the +4° C. and incubated at room temperature together with the treatment plates.

After 2 hours incubation, Glyo-fixx was removed from all plates and 100 µl of ice-cold 85% ethanol was added to each well. The plates were then incubated at +4° C. for 30 minutes.

Immunocytochemistry

Ethanol was removed from the plates and 100 µl of 5% BSA solution (Sigma A7906, in PBST) was added to each well. Plates were then incubated at room temperature for 30 minutes.

BSA was removed from the plates after 30 minutes incubation. To C7, KD2 and KD3 plates, 50 µl of primary antibody (p21; Abcam ab7903; 1/1000 in PBST) solution was added to each well. On 'zero day control' plate, 50 µl of the primary antibody was added to columns 1-6 while columns 7-12 received only 50 µl PBST on each well. These (columns 7-12) serve as a negative controls and will received secondary antibody only. Plates were then wrapped in cling film and were incubated at +4° C. overnight.

The following day, p21 primary antibody solution was removed from the plates and cells were washed by adding 200 µl of PBST. This was repeated once (total of 2 washes) and all plates were then subjected to secondary antibody treatment. Secondary antibody solution was made using am IgG-FITC (Abcam ab6785; 1/200 in PBST) and 50 µl was added to each well. Plates were then wrapped in aluminium foil to protect from light and were incubated at +4° C. for 2 hours.

After 2 hours incubation, secondary antibody was removed from the plates and cells were washed by adding 200 µl of PBST to each well and removing PBST. This was repeated once more (total of 2 washes). PI (Life Technologies P3566) solution (100 µl) was then added to each well.

Plates were wrapped in aluminium foil, incubated at 37° C. for 20 minutes and stored at +4° C. until analysis.

Cytometry and Data Analysis

Cytometry was performed using the Acumen Explorer TTP Lab Tech, Ltd. (Software version 3.1.12).

The propidium iodide staining was used to determine the cell cycle phase of the cells based on DNA content. It was measured using a 488 nm excitation laser triggering the 3° channel (bandpass filter 585-620 nm).

The immunostaining was used to measure the content of $p21^{cip1}$ in the cells. Measurement was carried out using a laser triggering the 1° channel (bandpass filter 500-530 nm).

Cell Cycle Analysis

To determine cut-offs for cells in different phases of the cell cycle, gate setting was performed based on the G1 and G2 peaks on the DNA content histogram. To determine the G1 and G2 peaks, the 3° total intensity in 20% histograms was analysed for each plate. Gates calculated were manually entered into the Acumen software.

The data exported and quantified included separately all cells and single cells. Single cells were further subcategorised into euploid, apoptotic and polyploid cells. Euploid cells were additionally classified into cells in G1 S and G2M phases of the cell cycle.

Cellular Protein Measurement

The total fluorescence intensity from the 1° channel was used to compare total protein levels in the different cell populations defined above. Mean fluorescence intensity per cell (for the whole of the population) and mean fluorescence intensity per cell (for positive cells only) were analysed separately. Additionally the proportion of positive cells in each population was calculated.

Media and Solutions

| Culture medium for SK-N-AS neuroblastoma cell line | |
|---|---|
| DMEM (Life Technologies 41966) | 435 ml |
| L-Glutamine 200 mM (Life Technologies 25030) | 5 ml |
| Penicillin/Streptomycin (Life Technologies 15070) | 5 ml |
| MEM-NEAA 100x (Life Technologies 11140) | 5 ml |
| Foetal Calf Serum Gold (PAA A15-151) | 50 ml |
| Total: | 500 ml |

| Culture medium for C7, KD2 and KD3 cell lines | |
|---|---|
| DMEM (Life Technologies 41966) | 435 ml |
| L-Glutamine 200 mM (Life Technologies 25030) | 5 ml |
| Penicillin/Streptomycin (Life Technologies 15070) | 5 ml |
| MEM-NEAA 100x (Life Technologies 11140) | 5 ml |
| Puromycin 10 mg/ml in $dH_2O$ (Sigma P8833) | 125 µl |
| Foetal Calf Serum Gold (PAA A15-151) | 50 ml |
| Total: | 500.125 ml |

| The 2x culture medium (contains double concentration of supplements) | |
|---|---|
| DMEM (Life Technologies 41966) | 370 ml |
| L-Glutamine 200 mM (Life Technologies 25030) | 10 ml |
| Penicillin/Streptomycin (Life Technologies 15070) | 10 ml |
| MEM-NEAA 100x (Life Technologies 11140) | 10 ml |
| Puromycin 10 mg/ml in $dH_2O$ (Sigma P8833) | 250 µl |
| Foetal Calf Serum Gold (PAA A15-151) | 100 ml |
| Total: | 500.250 ml |

Wash Medium

The wash medium used in cultures for drug treatments is DMEM (Life Technologies 41966) without supplements.

All cell culture media were made aseptically in the laminar flow cabinet and then stored at +4° C. The new media were evaluated for contaminations by transferring 6 ml of media into sterile 25 cm² tissue culture flasks and incubating the flasks at 37° C. humidified 5% $CO_2$ incubator for 48 hours. The flasks containing culture media were then examined under a phase contrast microscope and only media showing no sign of contaminations were used in subsequent experiments.

| Fixative (Glyo-fixx) Glyo-fixx solution (1 L) was made from 5x concentrate and stored at room temperature. | |
|---|---|
| Glyo-fixx 5x (Thermo Fisher 6764265/Lot 223925) | 201 ml |
| Distilled water | 614 ml |
| Ethanol (absolute) | 185 ml |
| Total: | 1000 ml |

| Phosphate buffered saline with 0.1% Triton X-100 (PBST) PBST were made fresh and stored at room temperature. | |
|---|---|
| PBS tablets (Sigma P4417/Lot SLBF4504V) | 3 |
| Distilled water | 599.4 ml |
| Triton X-100 (Fisher T3751/Lot 1277165) | 0.6 ml |
| Total: | 600 ml |

| Blocking solution (5% BSA in PBST) BSA solution was made fresh prior to use. | |
|---|---|
| BSA (Sigma A7906/Lot SLBB9570V) | 2 gr |
| PBST | 40 ml |
| 85% Ethanol solution (stored in −20° C.). | |
| Ethanol (absolute) | 170 ml |
| Distilled water | 30 ml |
| Total: | 200 ml |

| Primary Antibody solution Primary (p21) antibody solution was made (1/1000 in PBST) fresh prior to use. | |
|---|---|
| Anti-p21 antibody (mouse monoclonal; Abcam ab7903/Lot GR49981) | 22 µl |
| PBST | 22 ml |

| Secondary antibody solution Secondary antibody solution at dilution 1/200 in PBST was made fresh prior to use. | |
|---|---|
| Anti-mouse IgG-FITC (Abcam ab6785/Lot GR6891) | 110 µl |
| PBST | 22 ml |

Antibodies solution was mixed by inverting tubes 5 times. FITC-labelled antibody and its solutions were protected from light by wrapping the tubes in aluminium foil.

| Ribonuclease (RNaseA) solution | |
|---|---|
| RNaseA stock solution (10 mg/ml) was made in PBS containing 0.2% sodium azide and stored in +4° C. | |
| Sodium azide (Sigma S2002/Lot 98H0169) | 0.2 gr |
| D-PBS w/o $Ca^{2+}$ and $Mg^{2+}$ (Life Technologies 14190/Lot 1250143A) | 100 ml |
| Sodium azide was dissolved in D-PBS and the resulting solution was stored in +4° C. | |
| RNAs from bovine pancreas (Sigma R4875/Lot 061M15701V) | 100 mg |
| PBS containing 0.2% sodium azide | 10 ml |

| Propidium iodide (PI) staining solution PI staining solution was prepared fresh prior to use and was protected from light by wrapping the tube in aluminium foil. | |
|---|---|
| PBST | 42 ml |
| RNaseA A (10 mg/ml in PBS containing 0.2% sodium azide) | 420 µl |
| Propidium iodide (Life Technologies P3566/Lot 1090432) | 420 µl |

Solution was mixed by inverting tube 5 times.

Results and Conclusions

Sodium Valproate (SV)

We found that in C7 cells, the SV induces a slight G2 arrest leading to the accumulation of cells in G2 at the expense of G1 phase of the cell cycle (FIGS. 8A and 8B; white bars). As opposed to the response in C7, the KD2 (grey bars) and KD3 (black bars) cell lines respond to SV with a G1 inhibition (FIGS. 8A and 8B).

In the G2 sub-population of cells there is a significant upregulation of p21 protein at 1 µM SV (FIG. 8C). We also found that p21 expression is associated with a significant reduction of apoptotic fraction (% apoptotic in positive cells relative to p21 negative cells. FIG. 8D).

Although the p21 upregulation by SV is modest, the effects on reducing apoptosis are significant. The cell cycle modulator effects of SV are slightly different in the WS-deficient cells relative to the control cell line (C7), but this does not affect the anti-apoptotic effect of the protein.

Chloroquine Diphosphate

We found that chloroquine diphosphate has no significant cell cycle regulatory effects at the doses studied (FIGS. 9A and 9B).

In the C7 cells p21 expression is significantly increased in both G1 and G2M (FIGS. 9C and 9D white bars) and is associated with increased proportion of protein positive cells (FIGS. 9E and 9F, white bars).

The upregulation of p21 by Chloroquine diphosphate is different in WS-deficient cells KD2 and KD3. In KD2 cells the P21 is up-regulated in the G2M phase (FIG. 9D, grey bars) while in the KD3 cell line the upregulation of p21 occurs in G1 (FIG. 9C, black bars). Both are associated with increased in the proportion of protein positive cells (FIGS. 9E and 9F) The cells expressing p21 are significantly less likely to be apoptotic than the p21 negative cells (FIG. 9G).

In conclusion, Chloroquine diphosphate up-regulates p21 expression in all cell lines and increases the population of positive cells. P21 expression in Chloroquine diphosphate-treated cultures is associated with significantly reduced cell death.

Pioglizatone

We found that treatment with Pioglitazone did not have any significant cell cycle effects on all cell lines (FIG. 10A and FIG. 10B).

The drug was found to induce p21 expression in both the G1 and G2 subpopulations, albeit this induction is cell type dependent and are most modest in the KD3 cell line (FIGS. 10C and 10D). Apoptosis was significantly reduced in protein positive cells (FIG. 10E) relative to negative cells in all three cell lines.

In conclusion, upregulation of p21 protein following pioglitazone treatment was detected in all cell lines and p21 expression was associated with significantly reduced apoptosis.

Sodium 4-phenylbutyrate (4-PBA)

We found that 4-PBA has no effects on cell cycle in all three cell lines (FIGS. 11A and 11B).

The drug induces p21 expression in the G2 cell population in all three cell lines (FIG. 11C).

P21 expression is associated with significantly reduced apoptosis in all three cell lines (FIG. 11D Thus, although the induction of p21 is relatively small, the protective effect of the protein against apoptosis is significant in all three cell lines.

Fusidic Acid

We found that fusidic acid is a weak G2 inhibitor in all three cell lines (FIGS. 12A and 12B).

The drug leads to a significant increase in p21 expression in all cell lines (FIG. 12C) in all cell populations. The size of the effect is different in the two WFS1 cell lines (KD2 and KD3).

P21 expression is associated with the reduction of apoptosis in the positive cells (FIG. 12D).

We therefore conclude that Fusidic acid induces significant p21 expression in control C7 and WS-deficient KD2 and KD3 cells. The anti-apoptotic effect of the protein is significant in ensuring cell survival in the culture.

Ciclopirox Olamine (CPX)

In all cell lines CPX was found to induce a slight G1 cell cycle arrest in the expense of G2M phase (FIGS. 13A and 13B).

In all cell lines CPX induces significant p21 expression in both the G1 and G2 phase populations (FIGS. 13C and 13D).

P21 expression is associated with a significant reduction of apoptotic cells in the p21 positive cells (FIG. 13E).

In conclusion, CPX induced G1 cell cycle arrest and up-regulates p21 expression in all cell lines. P21 expression is associated with reduced cell death in all cell lines.

Dapsone

No cell cycle effects were observed following Dapsone treatment (FIGS. 14A and 14B).

Dapsone significantly up-regulates p21 expression in all three cell lines (FIGS. 14C and 14D).

P21 expression is associated with a significant reduction of apoptotic cells (FIG. 14E).

Overall Dapsone up-regulates p21 expression in both the control C7 and WS-deficient cells. The effects of protein in reducing apoptosis are significant.

Rifampicin

Rifampicin did not exert cell cycle effects in all cell lines (FIGS. 15A and 15B).

Rifampicin up-regulates p21 expression in both the control (C7) and WFS1 deficient cell lines (FIGS. 15C and 15D).

In all cultures the p21 expression is associated with a significant reduction of apoptosis (FIG. 15E).

Rifampicin treatment leads to p21 upregulation is all cell lines and the expression of the protein is associated with significant reduction in apoptosis.

Loperamide Hydrochloride

Loperamide was found to be a weak G1 inhibitor in all cell lines (FIGS. 16A and 16B).

Loperamide induce p21 expression in all three cell lines in both the G1 and G2 cell populations (FIGS. 16C and 216D.

P21 expression is associated with a significant reduction of apoptosis in the positive cells (FIG. 16E).

In conclusion, Loperamide induces a weak G1 cell cycle arrest in control and WS-deficient cell lines and up-regulates p21 expression in these cells. The p21 reduces apoptosis significantly.

List of abbreviations

ATF6a, Activating transcription factor 6 alpha
BiP, Immunoglobulin binding protein,
Glucose-regulated protein 78 (GRP78),
BSA, Bovine serum albumin
CA1, cornu ammonis 1
CHOP growth arrest and DNA-damage-inducible protein (C/EBP transcription factor)
CsCL, Caesium Chloride
CX, Cycloheximide
DMEM, Dulbecco's Modified Eagle Medium
DMSO, Dimethyl Sulfoxide
DTT, Dithiothreitol
ECL, Electrochemiluminescence
ER, Endoplasmic Reticulum
FBS, Fetal bovine serum
FCS, Fetal Calf Serum
FITC, Fluorescein isothiocyanate
GFP, Green Fluorescent Protein
GRP94, Glucose regulating protein 94
HCC, High Content Cytometry
HEK293 cells, Human Embryonic Kidney cells
HRD1, E3 ubiquitin-protein ligase synoviolin
IP, Immunoprecipitation
IRE-1, Inositol-requiring enzyme 1alpha
KD, Knockdown
MIN6, Mouse insulinoma pancreatic beta cell line
MOI, multiplicity of infection
NT2, Human Neuron-committed Teratocarcinoma
NS, Not significant
$OsO_4$, Osmium tetroxide
$p21^{cip}$, cell-cycle regulatory protein
PB, Phosphate Buffer
PBS: phosphate buffered saline
PBST: PBS with 1% Triton-100x
PCR, Polymerase Chain Reaction
PDI, Protein Disulphide-Isomerase
PDT, Population doubling time
PERK, Protein Kinase RNA-like Endoplasmic Reticulum Kinase
PI, Propidium Iodide
PDT, Population Doubling Time
PMSF, phenylmethanesulfonylfluoride
QPCR, Quantitative Polymerase Chain Reaction (Real time PCR)
RassF1A, RAS association domain family 1A
RIPA, Radio-Immunoprecipitation Assay
SDS-PAGE, PolyAcrylamide Gel Electrophoresis
SEM, Standard Error of the Mean
shRNA, short hairpin RNA
siRNA, small interfering RNA
SK-N-AS, Neuroblastoma cell lines
Tg, Thapsigargin
TBS, Tris-buffered saline
UPR, Unfolded protein response
WB, Western Blotting
WFS1, Wolfram syndrome 1, the gene encoding Wolfram protein
WFS1, Wolfram protein
Wt, wild type
XBP-1, X-Box binding protein 1

The invention claimed is:

1. A method of treating Wolfram Syndrome (WS)-related neurodegeneration, comprising administering to a patient in need thereof a compound selected from one or more of the group consisting of valproic acid and a salt thereof, wherein the (WS)-related neurodegeneration is caused by or linked to loss of function mutations in WFS1 genes, and wherein the compound is adminstered at an amount effective to increase the expression, increase the binding, increase the activation, increase the accumulation and/or increase the induction of p21.

2. A method according to claim 1, wherein the increased expression of p21 encompass one or both of:
   (i) increased transcription of p21; and/or
   (ii) reduced degradation of p21 RNA and/or peptide and/or protein.

3. A method according to claim 1, wherein the compound is capable of one or both of:
   (i) enhanced activation of p21;
   (ii) enhanced nuclear translocation of p21.

4. A method according to claim 1, wherein the compound acts to either increase the amount of p21 protein available and/or acts to maximize that any p21 protein is activated and has been delivered to the nucleus.

5. A method according to claim 1, wherein the compound acts to increase expression of p21.

6. A method according to claim 1, wherein the compound acts to increase p21 activation (without an increase in p21 expression).

7. A method according to claim 1, wherein the compound relieves symptoms, or halts the progression, of the disease, or results in an improvement in overall CNS function.

* * * * *